United States Patent
Stewart et al.

(12) 
(10) Patent No.: US 6,326,482 B1
(45) Date of Patent: *Dec. 4, 2001

(54) SH2 DOMAIN-CONTAINING PEPTIDES

(75) Inventors: Timothy A. Stewart, San Francisco; Yanmei Lu, Belmont, both of CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/367,206

(22) PCT Filed: Apr. 23, 1999

(86) PCT No.: PCT/US99/08847

§ 371 Date: Aug. 9, 1999

§ 102(e) Date: Aug. 9, 1999

(87) PCT Pub. No.: WO99/54467

PCT Pub. Date: Oct. 28, 1999

(51) Int. Cl.[7] .............................. C12P 21/06; C12N 5/06; C12N 5/10; C12N 1/20
(52) U.S. Cl. ............................................. 536/23.5
(58) Field of Search ............................. 514/44; 536/23.1, 536/24.1, 23.5; 424/130.1; 435/325, 252.1, 254.2, 69.1, 320.1, 348, 358, 252.33; 530/350, 387.1, 388.1, 388.15, 388.2, 388.22

(56) References Cited

U.S. PATENT DOCUMENTS 6,051,403 * 4/2000 Stewart et al. ...................... 435/69.1
6,051,690 * 4/2000 Stewart et al. ...................... 530/350

* cited by examiner

Primary Examiner—Robert A. Schwartzman
Assistant Examiner—Katharine F Davis
(74) Attorney, Agent, or Firm—Elizabeth M. Barnes

(57) ABSTRACT

The present invention relates to nucleotide sequences, including expressed sequence tags (ESTs), oligonucleotide probes, polypeptides, antagonists and agonists vectors and host cells expressing, and immunoadhesions and antibodies to PRO201, PRO308 or PRO309 polypeptides. The invention further relates to compositions and method for the diagnosis and treatment of neoplasfic cell growth and proliferation in mammals, including humans. The invention is based in part on the identification of genes that are amplified in the genome of tumor cells. Such gene amplification is expected to be associated with the overexpression of the gene product and contribute to tumorigenesis. Accordingly, the proteins encoded by the amplified genes are believed to be useful targets for the diagnosis and/or treatment (including prevention) of certain tumors (e.g. cancer) and may act as predictors of the prognosis of tumor treatment.

21 Claims, 29 Drawing Sheets

FIG. 1A

```
901  CCCAGAGCCA GAGGCCCCAT GGTGGGAGGC CGAGGAGGAT GAGGAGGAAG AGAATAGATG CCACAGGCTG AGATCTCTTT CTGCCCCCAT
     GGGTCTCGGT CTCCGGGGTA CCACCCTCCG GCTCCTCCTA CTCCTCCTTC TCTTATCTAC GGTGTCCGAC TCTAGAGAAA GACGGGGTA
251   P  E  P    E  A  P  W    W  E  A    E  E  D    E  E  E  E    N  R  C    F  T  R    P  Q  A  E    I  S  F    C  P  H

1001 GATGCCCCCT CCTGCTGCT GGGCCCCCAG AATCGGCCCC TGGAACCCCA AGTCCTGCAT ACCCTCCGTG GCCTGTTCCT GGAGCACCAT CCTGGAGCA
     CTACGGGGGA GGACGGACGA CCCGGGGGTC TTAGCCGGGG ACCTTGGGGT TCAGGACGTA TGGGAGGCAC CGGACAAGGA CCTCGTGGTA GGACCCTCGT
284   D  A  P  S    C  L  L    G  P  Q    N  R  P  L    E  P  Q    V  L  H    T  L  R  G    L  F  L    E  H  H    P  G  S  T

1101 CCGCCCTTCA CCTGCTATTG GTAGACTGCC AGGCCACAGG CCTCCTGGGA GTGACCAGAG ATCAGGGGG CAACATGGGA GTCTCATCTG GCCTGAGCT
     GGCGGGAAGT GGACGATAAC CATCTGACGG TCCGGTGTCC GGAGGACCCT CACTGGTCTC TAGTCGCCCC GTTGTACCCT CAGAGTAGAC CGGACTCGA
318   A  L  H    L  L  L    V  D  C  Q    A  T  G    L  L  G    V  T  R  D    Q  R  G    N  M  G    V  S  S  G    L  E  L

1201 GCTCACTCTT CCCCATGGAC GTTGGAACTG CTGGAGAGGC ATCAGACACT GGCGCTGCC CCAGGGGCGG GGGCGCTGG CGGTGCTGGG CTGCCGTGGG
     CGAGTGAGAA GGGGTACCTG CAACCTTGAC GACCTCTCCG TAGTCTGTGA CCGCGACCCG GGTCCCCGCC CCCGCGACGG GCCACGACCC GACGAGCCC
351   L  T  L    P  H  G  H    L  E  L    L  E  R  H    Q  T  L    A  L  A    G  A  L  A    V  L  G    C  S  G

1301 CCGCTGGAGG AGCGCGCAGC CGCACTGAGG GGACTGGTAG AGCTGGCGCT GCGCTGCGC CCAGGGGACT GCCGGGCTG GCTGCAGTCA
     GGCGACCTCC TCGCGCGTCG GCGTGACTCC CCTGACCATC TCGACCGCGA CGCGACGCG GGTCCCCTGA CGGGCCCGAC CGACGTCAGT
384   P  L  E  E    R  A  A    A  L  R    G  L  V  E    L  A  L    A  L  R    P  G  A  A    G  D  L  P    P  G  L    A  A  V  M

1401 TGGGCGCCCT GCTCATGCCC CAGGTGTCCC GGTTGGAGCA CACGTGGCGG CAGCTCCGAA GGAGGCTGCG CTGGCCTTTG AGCAGGAGCT
     ACCCGCGGGA CGAGTACGGG GTCCACAGGG CCAACCTCGT GTGCACCGCC GTCGAGGCTT CCTCCGACGC GACCGGAAAC TCGTCCTCGA
418   G  A  L    L  M  P    Q  V  S  R    L  E  H    T  W  R    Q  L  R  R    S  H  T    E  A  A    L  A  F  E    Q  E  L

1501 GAAGCCGCTG ATGCGGGCTC TGGATGAGGG CGCTGAGACC ACCTACTCCC GCGACGCTGG CGAGGTGGCC GTGGCACCCA TGGTTCGCCT ACTGGAGGGC
     CTTCGGCGAC TACGCCCGAG ACCTACTCCC GCGACTCTGG TGGATGAGGG GCGCTGCAC GCCGCCTGG CCACCGTGGT ACCAAGGCGA TGACCTCCCG
451   K  P  L    M  R  A  L    D  E  G    A  G  P    C  D  P  G    E  V  A    L  P  H    V  A  P  M    V  R  L    L  E  G

1601 GAGGAAGTCG CGGGGCCGCT GGACAGAGAG TGTGAGCGGC CTGCTCTCG ACAACGCGTG GCCGTCACA TGGTCCGGGA CGCACCCAAA TTCCGCAAGG
     CTCCTTCAGC GCCCCGGCGA CCTGTCTCTG ACACTCGCCG GACGAGAGC CGGCAGTGT GGCGCAGCT ACCAGGCCCT GCGTGGSTTT AAGGCGTTCC
484   E  E  V  A    G  P  L    D  E  S    C  E  R  L    L  R  T    L  H  G    A  R  H  M    V  R  D    A  P  K    F  R  K  V

1701 TGGCAGCCCA GCGCCTGCGA GGATTCCGGC CTAACCCGGA GCTGAGGGAG GCCCTGACCA CCGGCTTCGT GGGGAGGCTG CTCTGGGGTA GCCGGGGGCG
     ACCGTCGGGT CGCGGACGCT CCTAAGGCCG GATTGGGCCT CGACTCCCTC CGGGACTGGT GGCCGAAGCA CGCTCCGAGC GAGACCCCAT CGGCCCCCG
518   A  A  Q    R  L  R    G  F  R  P    N  P  E    L  R  E    A  L  T  T    G  F  V    R  R  L    L  W  G  S    R  G  A
```

FIG. 1B

```
1801 GGGAGCTCCG CGCGCTGAAC GCTTTGAGAA GTTCCAGCGC GTCCTCGGCG TCCTGTGCA GCGCCTGGAG CCTGACCGCT GAGAGCGCAG ACACCCTTCT
     CCCTCGAGGC GCGCGACTTG CGAAACTCTT CAAGGTCGCG CAGGAGCCGC AGGACAGCGT CGGCGACCTC GGACTGGCGA CTCTCGGGTC TGTGGAAGA
 551  G  A  P    R  A  E  R    F  E  K  F    Q  R  V  L    G  V  L  S    Q  R  L  E    P  D  D  R    Q

1901 TCACACCCGG GACCCCCAGG TTTTTGCGAA CCCCAGAAGA GTCGTCCCAG GCTCCTCGCG CCTCAGGTGG AATCCTGCCC TGTGCCTCAC
     AGTGTGGGCC CTGGGGGTCC AAAAACGCTT GGGGTCTTCT CAGCAGGGTC CGAGGAGCGC GGAGTCCACC TTAGGACGGG ACACGGAGTG

2001 AGAAGAGGTG GGGACCGCAG TCAGGGTCAC CTGGACCATG GTGAACATGT GACCTGCAGA TCTGGCATCA GAGGCCAGAG TTCAAATGTG ACTCCACCTC
     TCTTCTCCAC CCCTGGCGTC AGTCCCAGTG GACCTGGTAC CACTTGTACA CTGGACGTCT AGACCGTAGT CTCCGGTCTC AAGTTTACAC TGAGGTGGAG

2101 TTAAAGCCCG TGATTTCTAG CAGTTGACTT CACCTCTGTG TCGGCCTTTA ACAAAATCAT AGCCATACAG CAGTCAGGC CTGTAATCTC AGCACTTTGG
     AATTTTCGGC ACTAAAGATC GTCAACTGAA GTGGAGACAC AGCCGGAAAT TGTTTTAGTA TCGGTATGTC GTCAGTCCG GACATTAGAG TCGTGAAACC

2201 GAGGCCGAGG CGGAAGGAAG GCTTGAGGGC AGGAGTTCAA GACCAGCCAG GGCAACATGG TGAGACCTCA TCTCTACAAA AACTGAAAAA TAAAAAACTT
     CTCCGGCTCC GCCTTCCTTC CGAACTCCCG TCCTCAAGTT CCGTTGTCGTC CCGTTGTACC ACTCTGGAGT AGAGATGTTT TTGACTTTTT ATTTTTTGAA

2301 TTAAAAAAATG TAAAAAAAAA AAAAAAAGGG CGGCCCGGAC TCTAGAGTCG ACCTGCAGAA GCTTGGCCGC CATGGCCCAA CTTGTTTATT GCAGCTTATA
     AATTTTTTAC ATTTTTTTTT TTTTTTTCCC GCCGGGCCTG AGATCTCAGC TGGACGTCTT CGAACCGGCG GTACCGGGTT GAACAAATAA CGTCGAATAT

2401 ATGGTTACAA ATA
     TACCAATGTT TAT
```

```
901  CCAGCACGTA CTGAGCATGG ACTGCAGGGT TGCTAGGATA CTTGGAGTCT CTGAAGAGAT GAGGAGGAAC ATGGGGGTGA GCTCAGGGCT GGAACTCATT
     GGTCGTGCAT GACTCGTACC TGACGTCCCA ACGATCCTAT GAACCTCAGA GACTTCTCTA CTCCTCCTTG TACCCCCACT CGAGTCCGGA CCTTGAGTAA
230  Q  H  V   L  S  M  D   C  R  V   A  R  I    L  G  V  S   E  E  M    R  R  N   M  G  V  S   S  G  L    E  L  I

1001 ACCTTGCCTC ACGGACACCA GCTGCGCCTG GACATAATTG AAAGACACAA GTTCTGTGTT CACAATGGCC ATCGGCATTG CAGTGGACAT TCTGGGATGC ACGGGCACTT
     TGGAACGGAG TGCCTGTGGT CGACGCGGAC CTGTATTAAC TTTCTGTGTT CAAGACACAA GTCACCTGTA GTAGCCGTAAC GTCACCTGTA AGACCCTACG TGCCCGTGAA
263  T  L  P   H  G  H  Q   L  R  L   D  I  I  E   R  H  N    T  M  A   I  G  I  A   V  D  I    L  G  C    T  G  T  L

1101 TGGAGGACCG AGCGGCCACT CTGAGTAAGA TCATCCAGGT GGCGGTGGAA CTGAAGGATT CCATGGGGGA CTTGTATTCC TTCTCAGCTC TCATGAAAGC
     ACCTCCTGGC TCGCCGGTGA GACTCATTCT AGTAGGTCCA CCGCCACCTT GACTTCCTAA GGTACCCCCT GGAGATAAGG AAGAGTCGAG AGTACTTTCG
297  E  D  R   A  A  T   L  S  K  I    I  Q  V   A  V  E    L  K  D  S   M  G  D   L  Y  S    F  S  A  L   M  K  A

1201 CCTGGAAATG CCACAGATCA CAAGGTTAGA AAAGACGTGG ACTGCTCTGC GGCACCAGTA CACCCAAACT GCCATTCTCT ATGAGAAACA GCTGAAGCCC
     GGACCTTTAC GGTGTCTAGT GTTCCAATCT TTTCTGCACC TGACGAGACG CCGTGGTCAT GTGGGTTTGA CGGTAAGAGA TACTCTTTGT CGACTTCGGG
330  L  E  M   P  Q  I  T   R  L  E    K  T  W   T  A  L  R   H  Q  Y    T  Q  T   A  I  L  Y   E  K  Q    L  K  P

1301 TTCAGCAAAC TCCTGCATGA AGGCAGAGAG TCCACACATG TTCCCCCCAAA CAATGTATCA GTCCCACTGC TGATGCCGCT TGTGACGTTA ATGGAGCGCC
     AAGTCGTTTG AGGACGTACT TCCGTCTCTC AGGTGTGTAC AAGGGGGGTTT GTTACATAGT CAGGGTGACG ACTACGGCGA ACACTGCAAT TACCTCGCGG
363  F  S  K   L  L  H  E   G  R  E    S  T  C   V  P  P  N   N  V  S    V  P  L  L   M  P  L    V  T  L   M  E  R  Q

1401 AGGCTGTGAC TTTTGAAGGA AAAACTTCCT TGGCTGTACA CCCTTTTTT GGGAAAAAAA CGACCAGAGC TGTGAAATCA TGCTGAACCA TTTGGCAACA GCGCGATTCA TGGCCGAGGC
     TCCGACACTG AAAACTTCCT AAAACTTCCT ACCGACATGT GGGAAAAAAA GCTGGTCTCG ACACTTTAGT ACGACTTGGT AAACCGTTGT CGCGCTAAGT ACCGGCTCCG
397  A  V  T   F  E  G    T  D  M  W   E  K  N   D  Q  S    C  E  I  M   L  N  H   L  A  T    A  R  F  M   A  E  A

1501 TGCAGACAGC TACCGGATGA ATGCTGAGAG GATCCTGGCA GGTTTTCAAC CAGATGAAGA AATGAATGAA ATCTGCAAGA CTGAATTTCA AATGCGATTG
     ACGTCTGTCG ATGGCCTACT TACGACTCTC CTAGGACCGT CCAAAAGTTG GTCTACTTCT TTACTTACTT TAGACGTTCT GACTTAAAGT TTACGCTAAC
430  A  D  S   Y  R  M  N   A  E  R    I  L  A   G  F  Q  P   D  E  E    M  N  E   I  C  K  T   E  F  Q    M  R  L

1601 CTATGGGGCA GCAAAGGTGC ACAAGTCAAT CAGACAGAGA GATATGAGAA ATTCAACCAG CCCTCTCGCG TAAATTGGAA CCCTCCTCCTG
     GATACCCCGT CGTTTCCACG TGTTCAGTTA GTCTGTCTCT CTATACTCTT TAAGTTGGTC GGGAGAGCGC ATTTAACCTT GGGAGGAGAC
463  L  W  G   S  K  G  A   Q  V  N    Q  T  E  R   Y  E  K    F  N  Q   I  L  T  A   L  S  R    K  L  E   P  P  P  V

1701 TAAAGCAGGC AGAGCTTTGA TAACTCTCCA GAGAACCTTT AGAATATCTT TTCAAGTTTC CCCAGCTTCA TCTTTGGAA AGCTTACTGT TTTTGATAAA
     ATTTCGTCCG TCTCGAAACT ATTGAGAGGT CTCTTGGAAA TCTTATAGAA AAGTTCAAAG GGGTCGAAGT AGAAACCCTT TCGAATGACA AAAACTATTT
497  K  Q  A   E  L  O
```

FIG. 2B

```
1801  GTAATAATGT GCAAATCTGA CAATATACAA GCTTTTAGTA TCCACAGGAT ATTAAACGTG TAAATTGCAC AGAGCACACT TATTTATGAA TTGTCTAAAG
      CATTATTACA CGTTTAGACT GTTATATGTT CGAAAATCAT AGGTGTCCTA TAATTTGCAC ATTAACGTG TCTCGTGTGA ATAAATACTT AACAGATTTC

1901  TTACTACTGA TTTTAAAATG AATAATTTAT TATTAAGGTA ACTACTGCTA ATGTTGATCA GCAAATTTAA GAGAAGACCT AGCTATGTTG GCTGGTTGCT
      AATGATGACT AAAATTTTAC TTATTAAATA ATAATTCCAT TGATGACGAT TACAACTAGT CGTTTAAATT CTCTTCTGGA TCGATACAAC CGACCAACGA

2001  TTCTATTATC ATGGTATTTG ACCATTTTAG ATGTCAGATA AGTGTAAATA GAAGAGTTTA AAAGCATGAA ACATTTCAGA AGGTATCAGT
      AAGATAATAG TACCATAAAC TGGTAAAATC TACAGTCTAT TCACATTTAT CTTCTCAAAT TTTCGTACTT TGTAAAGTCT TCCATAGTCA

2101  TATATGATAT TCTTTAAACA AATATGAAAA ATGTAAATAC TCATGAATGA AAATACATCT TTTTGTGAAA CAGT
      ATATACTATA AGAAATTTGT TTATACTTTT TACATTTATG AGTACTTACT TTTATGTAGA AAAACACTTT GTCA
```

FIG. 2C

```
                                                                                                    (SEQ ID
                                                                                                    NO: 6)
  1 TAGGAGGTCC CCGGGTTGCC GGCGGCGACA GCGGGGGAAG CATGACTGCT GTGGGCCCGA AGGTGCCCCGC CGAGGGGGTCC CTGGAGAGCC  (SEQ ID
    ATCCTCCAGG GGCCCAACGG CCGCCGCTGT CGCCCCCTTC GTACTGACGA CACCCGGCTT CCACGGGGCG CGACCCCAGG GACCTCTCCG   NO: 5)
  1                                              M  T  A   V  G  R  R   C  P  A    L  G  S  R   G  A  A    G  E  P

101 AGAGGCTGGC AGCGACTATG TGAAGTTCTC CAAGGAGAAG ACTCATCGCC AGAGAAACTC CACAAGGAAT TGGAGAGAGA GCTCAAACTC
    TCTCCGACCG TCGCTGATAC ACTTCAAGAG GTTCCTCTTC TGAGTAGCGG TCTCTTTGAG GTGTTCCTTA ACCTCTCCT CGAGTTGAG
 21  E  A  G   S  D  Y  V   K  F  S   K  E  K    Y  I  L  D    S  S  P   E  K  L    H  K  E  L   E  E  E   L  K  L

201 AGCAGACAGG ATCTCCGCAG CCATATGGCC TACCCCCCG AGAGTCTCG GAGACCTTGG TACAACGCAA CGGCGACTTC CTCATCCGGG
    TCGTCTGTCC TAGAGGCGTC GGTACCGG ATGGTACCGG CTCTGGAACC CTCTGGAACC ATGTTGCGTT GCCGCTGAAG GAGTAGGCCC
 54  S  S  T   D  L  R  S   H  A  W   Y  H  G    R  I  P  R    E  V  S   E  T  L   V  Q  R  N    G  D  F    L  I  R  D

301 ACTCGCTCAC CAGCCTGGGC GACTATGTGC TCACGTGCCG CTGGCCAAC ACTTCAAGAT CAACAAGTG GTGGTGAAGG CAGGAGAG
    TGAGCGAGTG GTCGGACCCG CTGATACACG AGTGCACGGC GACCGGCTG GTCGGAACG TGAAGTTCTA GTTGTTCCAC CACCACTTCC GTCCGTCTC
 88    S  L  T    S  L  G   D  Y  V  L   T  C  R    W  R  N    Q  A  L  H    F  K  I    N  K  V    V  V  K  A    G  E  S

401 CTACACACAC ATCCAGTACC TGTTTGAGCA GGAGAGCTTT CCCGGTGAAC CGGCCACTTCC GACCACGTGC GGCTATCAT GTGGGCAGCC GCAAGGCTGT GTCAGAGCAG
    GATGTGTGTG TAGGTCATGG ACAAACTCGT CCTCTCGAAA GGGCCACTTG GCCGGTGAAGG CTGGTGCACG CCGATAGTA CACCCGTCGG CGTTCCGACA CAGTCTCGTC
121  Y  T  H    I  Q  Y  L    F  E  Q   E  S  F    P  V  N    R  T  F  P    L  R  Y    D  H  V  P    A  L  V    R  Y  H    V  G  S  R   K  A  V   S  E  Q

501 AGTGTGCCA TCATCTACTG CCCGGTGAAC CGGCCACCTTCC CGGACCTTCC CACTGCGCTA CCTCAGGGCC CTCGAGGCC CACCATGGCC ACCCTGTCCC CCTGTAGCC
    TCACCACGGT AGTAGATGAC GGGCCACTTG CTCTCGAAA GGGCCACTTG GGGCCACTTG GTGACGCGAT GGAGCTCCGG TGATACCGG TGGTACTGG TACCGAGTG GGACGATCGG
154  S  G  A   I  I  Y  C    P  V  N    R  T  F  P    L  R  Y    L  E  A    S  Y  G  L    E  A    S  Y  G  L    G  Q  G    S  S  K    P  A  S  P

601 CCGTCAGCCC CTCAGGCCCC AAGGGCCAGC TTCCCGTTCG TGTACTTCGC ACATGAAGCG GGCAGCGTC CGCGTCTCGG ACCATGACCG ATGGGCTCAC TGCTGACAAG GTCACCCGCA GCGATGGCTG
    GGCAGTCGGG GAGTCCGGGG TTCCCGGTCG AAGGGCAAGC ACATGAAGCG CCGTCGCAG GCGCAGCGCG GCGGCAGAGCG TGGTACTGGG TACCGAGTG ACGACTGTTC CAGTGGGCGT CGTACCGAC
188   V  S  P    S  G  P   K  G  S  H    M  K  R    R  S  V    T  M  T  D    G  L  T    A  D  K    V  T  R  S    D  G  C

701 CCCACCAGT ACGTCGCTGC CCCGCCCTCG GGACTCCCAT CGCAGTCCATC GGACCAGATC CCTGGTCTG GGTCTGACG ACTCACCCAT GTCGCCCAT CAGGGGGTAG
    GGGTGGTCA TGCAGCGACG GGGCGGGAGC CCTGAGGTAG CCGTCTAGG CCTGGTCTAG GGACCAGATC CCAGACTGC TGAGTGGGTA CAGCGGGTAG
221   P  T  S    T  S  L  P    R  P  R    D  S  I    R  S  C  A    L  S  M    D  Q  I  P    D  L  H    S  P  M    S  P  I
```

FIG. 3A

```
 801 TCCGAGAGCC CTAGCTCCCC TGCCTACAGC ACTGTAACCC GTGTCCATGC CGCCCTTCTG CCACAGCATT GCCTGCCTCC CCTGTCGCCC
     AGGCTCTCGG GATCGAGGGG ACGGATGTCG TGACATTGGG CACAGGTACG GCGGGAACGT CGGGGAAGAC GGTGTCGTAA CGGACGGAGG GGACAGCGGG
 254  S  E  S  P  S  S  P  A  Y  S  T  V  T  R  V  H  A  A  P  A  A  P  S  A  T  A  L  P  A  S  P  V  A  R

901 GCTGTTCCAG TGAGCCCCAG CTGTGTCCCG GAAGTGCCCC AAAGACCCAT GGGGAGTCAG ACAAGGGCCC CCACACCAGC CCCTCCCACA CCCTTGGCAA
     CGACAAGGTC ACTCGGGGTC GACACAGGGC CTTCACGGGG TTTCACGGGTA CCCCTCAGTC TGTTCCCGGG GGTGTGGTGT GGGAGGGTGT GGGAACCGTT
 288  C  S  S  E  P  Q  L  C  P  G  S  A  P  K  T  H  G  E  S  D  K  G  P  H  T  S  P  S  H  T  L  G  K

1001 GGCCTCCCCG TCACCATCAC TCAGCAGCTA CAGTGACCCG GACTCTGGCC ACTACTGCCA GCTCCAGCCT CCCGTGCGTG GCAGCCGAGA GTGGGCAGCG
     CCGAGGGGC AGTGGTAGTG AGTCGTCGAT GTCACTGGGC CTGAGACCGG TGATGACGGT CGAGGTCGGA GGGCACGCAC CGTCGGCTCT CACCCGTCGC
 321  A  S  P  S  P  S  L  S  S  Y  S  D  P  D  S  G  H  Y  C  Q  L  Q  P  P  V  R  G  S  R  E  W  A  A

1101 ACTGAGACCT CCAGCCAGCA GGCCAGGAGC TATGGGGAGA GGCTAAAGGA ACTGTCAGAA CTTCCAGTCA CTACTGATCC CAGGGATAA CCGGCCACTG
     TGACTCTGGA GGTCGGTCGT CCGGTCCTCG ATACCCCTCT CCGATTTCCT TGACAGTCTT GAAGGTCAGT GATGACTAGG GGTCCCTATT TGGCCGGTGAC
 354  T  E  T  S  S  Q  Q  A  R  S  Y  G  E  R  L  K  E  L  S  E  N  G  A  P  E  G  D  W  G  K  T  F  T  V

1201 TCCCATCGT GGAAGTCACT TCTTCCTTCA ACCCGGCCAC CTTCCAGTCA CTACTGATCC CTACTGATCC GAAGGTCAGT TGGCCGGTGAC CTCCACCCGG AAGACGCGTT
     AGGGTAGCA CCTTCAGTGA AGAAGGAAGT TGGGCCGGTG GAAGGTCAGT
 388  P  I  V  E  V  T  S  S  F  N  P  A  T  F  Q  S  L  L  I  P  R  D  N  R  P  L  E  V  G  L  L  R  K

1301 GGTCAAGGAG CTGCTGGCAG AAGTGGATGC CCGGACGCTG TCACCAAGGT GGACTGCCTG GTTGCTAGGA TACTGGGCGT TACCAAGGAG
     CCAGTTCCTC GACGACCGTC TTCACCTACG GGCCTGCGAC AGTGGTTCCA CCTGACGGAC CAACGATCCT ATGACCCGCA ATGGTTCCTC
 421  V  K  E  L  L  A  E  V  D  A  R  T  L  A  R  H  V  T  K  V  D  C  L  V  A  R  I  L  G  V  T  K  E

1401 ATGCAGACCC TAATGGGAGT CCGCTGGGGC ATGGAACTGC TCACCCTCCC CAGCTACGCC TAGACCTGCT GGAAAGGTTC CACACCATGT
     TACGTCTGGG ATTACCCTCA GGCGACCCCG TACCTTGACG AGTGGGAGGG GTCGATGCGG ATCTGGACGA CCTTTCCAAG GTGTGGTACA
 454  M  Q  T  L  M  G  V  R  W  G  M  E  L  L  T  L  P  H  G  R  Q  L  R  L  D  L  L  E  R  F  H  T  M  S

1501 CCATCATGCT GGCCGTGGAT ATCCTGGGCT GCACCGGCTC TGCGGAGGAG CGGGCAGCGC TGCTGCACAA GACCATTCAG CTGGCGGCCG AGCTACGGGG
     GGTAGTACGA CCGGCACCTA TAGGACCCGA CGTGGCCGAG ACGCCTCCTC GCCCGTCGCG ACGACGTGTT CTGGTAAGTC GACCGCCGGC TCGATGCCCC
 488  I  M  L  A  V  D  I  L  G  C  T  G  S  A  E  E  R  A  A  L  L  H  K  T  I  Q  L  A  A  E  L  R  G

1601 GACTATGGGC AACATGTTCA GCTTCGCGGC GGTCATGGGT GCCCTGGACA TGGCTCAGAT TTCTCGGCTG GAGCAGACAT GGTGACCCT GCGGCAGCGA
     CTGATACCCG TTGTACAAGT CGAAGCGCCG CCAGTACCCA CGGGACCTGT ACCGAGTCTA AAGAGCCGAC CTCGTCTGTA CCACTGGGA CGCCGTCGCT
 521  T  M  G  N  M  F  S  F  A  A  V  M  G  A  L  D  M  A  Q  I  S  R  L  E  Q  T  W  V  T  L  R  Q  R
```

FIG. 3B

```
1701 CACACAGAGG GTGCCATCCT GTACGAGAAG AAGCTCAAGC CTTTTCTCAA GAGCCTCAAC GAGCCTCAAC GAGGGCAAAG AAGGCCCGCC GCTGAGCAAC ACCACGTTTC
     GTGTGTCTCC CACGGTAGGA CATGCTCTTC TTCGAGTTCG GAAAAGAGTT CTCGGAGTTG CTCCCGTTTC TTCCGGGCGG CGACTCGTTG TGGTGCAAAG
554   H  T  E  G   A  I  L    Y  E  K   K  L  K  P    F  L  K    S  L  N    E  G  K  E    G  P  P    L  S  N    T  T  F  P

1801 CTCATGTGCT GCCCCTCATC ACCCTGCTGG AGTGTGACTC GGCCCCACCA GAGGGCCCTG AGCCCTGGGG CAGCACGGAG CACGGCGTGG AGGTGGTGCT
     GAGTACACGA CGGGGAGTAG TGGGACGACC TCACACTGAG CCGGGGTGGT CTCCCGGGAC TCGGGACCCC GTCGTGCCTC GTGCCGCACC TCCACCACGA
588   H  V  L   P  L  I    T  L  L  E    C  D  S    A  P  P    E  G  P  E    P  W  G    S  T  E    H  G  V  E    V  V  L

1901 GGCTCACCTG GAGGCCGCCC GCACAGTGGC ACACCACGGA GGCCTGTACC CGGACATGG TGTGGTTACG ACTTCAGTTC GACGTCCCCA AGTCCGGGC CGGCCTCGAG
     CCGAGTGGAC CTCCGGCGGG CGTGTCACCG TGTGGTGCCT CCGGACATGG ACACCAATGC TGAAGTCAAG CTGCAGGGGT TCCAGGCCCG GCCGGAGCTC
621   A  H  L    E  A  A  R    T  V  A    H  H  G    G  L  Y  H    T  N  A    E  V  K    L  Q  G  F    Q  A  R    P  E  L

2001 CTGGAGGTGT TCAGCACGGA GTTCCAGATG CGCCTTCTCT GGGGCAGTCA GGGTGCCAGC AGCAGCCAGG CCCGGCGCTA TGAGAAGTTC GACAAGGTCC
     GACCTCCACA AGTCGTGCCT CAAGGTCTAC GCGGAAGAGA CCCCGTCAGT CCCACGGTCG TCGTCGGTCC GGGCCGCGAT ACTCTTCAAG CTGTTCCAGG
654   L  E  V  F    S  T  E    F  Q  M    R  L  L  W    G  S  Q    G  A  S    S  S  Q  A    R  R  Y    E  K  F    D  K  V  L

2101 TCACTGCCCT GTCCCACAAG CTGGAACCTG CTGTCCGCTC CAGCGAGCTG TGA
     AGTGACGGGA CAGGGTGTTC GACCTTGGAC GACAGGCGAG GTCGCTCGAC ACT
688   T  A  L    S  H  K    L  E  P  A    V  R  S    S  E  L    O
```

FIG. 3C (SEQ ID NO: 13)

GTGGAGGGCGGGGGTGACAGCAGCCCGGAGCCGCGGAGCCTCAGCTTCCGCCTGGACCCA
GCCTCGTGGGAGCCCCGCGGGTCCTGCCCAGATGTGGAAGACTGAGGCCTGTTGAAAGTG
CAGAGCTCAGCCCTGGCACCCTCTGTTCCCAAGAGCTCCATGCAGGTGCCACAGGATGGA
GAAGACCTTGCTGGCCAACCTTGGTACCACGGCCTCCTGTCCCGCCAGAAGGCTGAAGCT
CTTCTTCAGCAAAA

FIG. 4A (SEQ ID NO: 14)

CATCGCCCAGCACGTACTGAGCATGGACTGCAGGGTTGCTAGGATACTTGGAGTCTCTNA
AGAGATGAGGAGGAACATGGGGGTGAGCTCAGGCCTGGAACTCATTACCTTGCCTCACGG
ACACCAGCTGCGCCTGGACATAATTGAAAGACACAACACAATGGCCATCGGCATTCGCGT
GGACATTCTGGGATGCACGGGCACTTTGGAGG

FIG. 4B (SEQ ID NO: 15)

GCTGGCAGAAGTGGATGCCCGGACGCTGGCCCGGCATGTCACCAAGGTGGACTGCCTGGT
TGCTAGGATACTGGGCGTTACCAAGGAGATGCAGACCCTAATGGGAGTCCGCTGGGGCAT
GGAACTGCTCACCCTCCCCCATGGCCGGCAGCTACGCCTAGACCTGCTGGAAAGGTTCCA
CACCATGTCCATCATGCTGGCCGNGGACATCCTGGGCTGCACCGGCTCTGCGGAGGAGCG
GG

FIG. 4C (SEQ ID NO: 7)
Probe for Cloning NSP1:        ACTGAGGCCTGTTGAAAGTGCAGAGCTCAG (SEQ ID NO: 8)
Enrichment Primer for NSP1:    GCTGAAGAAGAGCTTCAG

FIG. 5A (SEQ ID NO: 9)
Probe for Cloning NSP2:

CAATGCCGATGGCCATTGTGTTGTGTCTTTCAATTATGTCCAGGCGCA (SEQ ID NO: 10)
Enrichment Primer for NSP2:ATCCCAGAATGTCCACTG

FIG. 5B (SEQ ID NO: 11)
Probe for cloning nsp3:

GGCCAGCATGATGGACATGGTGTGGAACCTTTCCAGCAGGTCTAGGCGTA (SEQ ID NO: 12)
enrichment primer for nsp3: GGTGCAGCCCAGGATGTC

FIG. 5C

```
nsp1    1  - - - - - - - - - - - - - - - - - - - - - - - - - - - - - - - - - - - - - - - - - M Q ⎤
nsp3    1  M T A V G R R C P A L G S R G A A G E P E A G S D Y V K F S K E K Y I L D S S P E K L H K E L E E E │ nsp1    3  V P Q D G E D L A G Q P W Y H G L L S R Q K A E A L L Q Q D G D F L V R A S G S R G G N P V I S C R │
nsp3   51  L K L S S T D L R S H A W Y H G R I P R E V S E T L V Q R N G D F L I R D S L T S L G D Y V L T C R │ SH2 domain nsp1   53  W R G S A L H F E V F R V A L R P R P G R P T A L F Q L E D E Q F P S I P A L V H S Y M T G R R P L │
nsp3  101  W R N Q A L H F K I N K V V V K A G E S Y T H I Q Y L F E Q E S F D H V P A L V R Y H V G S R K A V │
nsp2    1  - - - - - - - - - - - - - - - - - - - - - - - - - - - - - - - - - - M Q D R R A L S ⎦ nsp1  103  S Q A T G A V V S R P V T W Q G P L R R S F S E D T L M D G P A R I E P L R A R K W S N S Q P A D L ⎤
nsp3  151  S E Q S G A I I Y C P V N R T F P L R Y L E A S Y G L G Q G S S K P A S P V S P S G P K G S H M K R │
nsp2    9  L K A H Q S E S Y L P I G C K L P P Q S S G V D T S P C P N S - - P V F R T G S E P A L S P A V V R │ nsp1  153  A H M G R S R E D P A G M E A S T M P I S A L P R T S S - - - - - - - - - - - - - - - - - - - - - - │
nsp3  201  R S V T M T D G L T A D K V T R S D G C P T S T S L P R P R D S I R S C A L S M D Q I P D L H S P M │
nsp2   57  R V S S D A R A G E A L R G S D S Q L C P K P P P K P - - - - - - - - - - - - - C K V P F L K V P S │ nsp1  181  - - - - - - - - - - - - D P V L L K A P A P L G T V A D S L R A S D G Q L Q A K A P T K P P R T P S │
nsp3  251  S P I S E S P S S P A Y S T V T R V H A A P A A P S A T A L P A S P V A R C S S E P Q L C P G S A P │
nsp2   94  S P S - - - - - - - - - - A W L N S E A N Y C E L N P A F A T G C G R G A K L P S C A Q G S H T E │ nsp1  219  F E L P D A S E - - - - - - - - - - - - - - - - - - - - - - - - - - - - R P P T Y C E L │ PS domain
nsp3  301  K T H G E S D K G P H T S P S H T L G K A S P S P S L S S Y S D P D S G H Y C Q L Q P P V R G S R E │
nsp2  133  L L T A K Q N E - - - - - - - - - - - - - - - - - - - - - - - - - - - - A P G P R N S G V │ nsp1  235  V P R V P S V Q G T S P S Q S C P E P E A P W W E A E D E E E E N R C F T R P Q A E I S F C P H D │
nsp3  351  W A A T E T S S Q Q A R S Y G E R L K E L S E N G A P E G D W G K T F T V P I V E V T S S F N P A T │
nsp2  150  N Y L I L D D D D R E R P W E P A A A Q M E K G Q W D K G - - - - E F V T P L L E T V S S F R P N E │ nsp1  285  A P S C L L G P Q N R P L E P Q V L H T L R G L F L E H H P G S T A L H L L V D C Q A T G L L G V │
nsp3  401  F Q S L L I P R D N R P L E V G L L R K V K E L L A E V D A R T L A R H V T K V D C L V A R I L G V │
nsp2  196  F E S K F L P P E N K P L E T A M L K R A K E L F T N N D P K V I A Q H V L S M D C R V A R I L G V ⎦ nsp1  335  T R D Q R G N M G V S S G L E L L T L P H G H H L R L E L L E R H Q T L A L A G A L A V L G C S G P
nsp3  451  T K E M Q T L M G V R W G M E L L T L P H G R Q L R L D L L E R F H T M S I M L A V D I L G C T G S
nsp2  246  S E E M R R N M G V S S G L E L I T L P H G H Q L R L D I I E R H N T M A I G I A V D I L G C T G T nsp1  385  L E E R A A A L R G L V E L A L A L R P G A A G D L P G L A A V M G A L L M P Q V S R L E H T W R Q
nsp3  501  A E E R A A L L H K T I Q L A A E L R G T M G - N M F S F A A V M G A L D M A Q I S R L E Q T W V T
nsp2  296  L E D R A A T L S K I I Q V A V E L K D S M G - D L Y S F S A L M K A L E M P Q I T R L E K T W T A nsp1  435  L R R S H T E A A L A F E Q E L K P L M R A L D E G A G - - P C D P G E V A L P H V A P M V R L L E
nsp3  550  L R Q R H T E G A I L Y E K K L K P F L K S L N E G K E - - G P P L S N T T F P H V L P L I T L L E
nsp2  345  L R H Q Y T Q T A I L Y E K Q L K P F S K L L H E G R E S T C V P P N N V S V P L L M P L V T L M E nsp1  483  G E E V A G - - - - - - - P L D E S C E R L L R T L H G A R H M V R D A P K F R K V A A Q R L R G F
nsp3  598  C D S A P P E G P E P W G S T E H G V E V V L A H L E A A R T V A H H G G L Y H T N A E V K L Q G F
nsp2  395  R Q A V T F E G T D M W E K N D Q S C E I M L N H L A T A R F M A E A A D S Y R M N A E R I L A G F nsp1  526  R P N P E L R E A L T T G F V R R L L W G S R G A G A P R A E R F E K F Q R V L G V L S Q R L E P D
nsp3  648  Q A R P E L L E V F S T E F Q M R L L W G S Q G A S S S Q A R R Y E K F D K V L T A L S H K L E P A
nsp2  445  Q P D E E M N E I C K T E F Q M R L L W G S K G A Q V N Q T E R Y E K F N Q I L T A L S R K L E P P nsp1  576  R - - - - - -
nsp3  698  V R S S E L -
nsp2  495  P V K Q A E L
```

FIG. 6B

MQVPQDGEDLAGQPWYHGLLSRQKAEALLQQDGDFLVRASGSRGGNPVISCRWRGSALHF
EVFRVALRPRPGRPTALFQLEDEQFPSIPALVHSYMTGRRPLSQATGAVVSRPVTWQGPL
RRSFSEDTLMDGPARIEPLRARKWSNSQPADLAHMGRSREDPAGMEASTMPISALPRTSS
DPVLLKAPAPLGTVADSLRASDGQLQAKAPTKPPRTPSFELPDASERPPTYCELVPRVPS
VQGTSPSQSCPEPEAPWWEAEEDEEEENRCFTRPQAEISFCPHDAPSCLLGPQNRPLEPQ
VLHTLRGLFLEHHPGSTALHLLLVDCQATGLLGVTRDQRGNMGVSSGLELLTLPHGHHLR
LELLERHQTLALAGALAVLGCSGPLEERAAALRGLVELALALRPGAAGDLPGLAAVMGAL
LMPQVSRLEHTWRQLRRSHTEAALAFEQELKPLMRALDEGAGPCDPGEVALPHVAPMVRL
LEGEEVAGPLDESCERLLRTLHGARHMVRDAPKFRKVAAQRLRGFRPNPELREALTTGFV
RRLLWGSRGAGAPRAERFEKFQRVLGVLSQRLEPDR

FIG. 7

```
nsp1.SH2    1  MQVPQDGEDLAGQPWYHGLLSRQKAEALLQQDGDFLVRASGSRGGNPV
HuShc.SH2   1  ----------EQLRGEPWFHGKLSRREAEALLQLNGDFLVRESTTTPGQYV
HuSCK.SH2   1  ----------EQLRQEPWYHGRMSRRAAERMLRADGDFLVRDSVTNPGQYV
HuFes.SH2   1  ---------KPLHEQLWYHGAIPRAEVAELLVHSGDFLVRESQGKQ-EYV nsp1.SH2   51  CRWRGSALHFEVFRVALRPRPGRPTALFQLEDEQFPSIPALVHSYMTG
HuShc.SH2  44  GLQSGQPKHLLLVDPEG------VVRTKDHRFESVSHLTSYHMDN
HuSCK.SH2  44  GMHAGQPKHLLLVDPEG------VVRTKDVLFESTSHLIDHHLQN
HuFes.SH2  43  VLWDGLPRHFIIQSLDN------LYRLEGEGFPSIPLLIDHLLST nsp1.SH2  101  PLSQATGAVVSRPVTWQG--------
HuShc.SH2  85  PIISAGSELCLQQPVERKL--------
HuSCK.SH2  85  PIVAAESELHLRGVSREP---------
HuFes.SH2  84  PLTKKSGVLHRAVPKDKWVLNHEDLVLGEQIGRGN
```

FIG. 8

```
Ala Ala Gly Glu Pro Glu Ala Gly Ser Asp Tyr Val Lys Phe Ser
  1           5                  10                  15

Lys Glu Lys Tyr Ile Leu Asp Ser Ser Pro Glu Lys Leu His Lys
           20                  25                  30

Glu Leu Glu Glu Glu Leu Lys Leu Ser Ser Thr Asp Leu Arg Ser
               35                  40                  45

His Ala Trp Tyr His Gly Arg Ile Pro Arg Glu Val Ser Glu Thr
                50                  55                  60

Leu Val Gln Arg Asn Gly Asp Phe Leu Ile Arg Asp Ser Leu Thr
                65                  70                  75

Ser Leu Gly Asp Tyr Val Leu Thr Cys Arg Trp Arg Asn Gln Ala
                80                  85                  90

Leu His Phe Lys Ile Asn Lys Val Val Val Lys Ala Gly Glu Ser
                95                  100                 105

Tyr Thr His Ile Gln Tyr Leu Phe Glu Gln Glu Ser Phe Asp His
                110                 115                 120

Val Pro Ala Leu Val Arg Tyr His Val Gly Ser Arg Lys Ala Val
                125                 130                 135

Ser Glu Gln Ser Gly Ala Ile Ile Tyr Cys Pro Val Asn Arg Thr
                140                 145                 150

Phe Pro Leu Arg Tyr Leu Glu Ala Ser Tyr Gly Leu Gly Gln Gly
                155                 160                 165

Ser Ser Lys Pro Ala Ser Pro Val Ser Pro Ser Gly Pro Lys Gly
                170                 175                 180

Ser His Met Lys Arg Arg Ser Val Thr Met Thr Asp Gly Leu Thr
                185                 190                 195

Ala Asp Lys Val Thr Arg Ser Asp Gly Cys Pro Thr Ser Thr Ser
                200                 205                 210

Leu Pro Arg Pro Arg Asp Ser Ile Arg Ser Cys Ala Leu Ser Met
                215                 220                 225

Asp Gln Ile Pro Asp Leu His Ser Pro Met Ser Pro Ile Ser Glu
                230                 235                 240

Ser Pro Ser Ser Pro Ala Tyr Ser Thr Val Thr Arg Val His Ala
                245                 250                 255

Ala Pro Ala Ala Pro Ser Ala Thr Ala Leu Pro Ala Ser Pro Val
                260                 265                 270
```

FIG. 19A

Ala Arg Arg Ser Ser Glu Pro Gln Leu Cys Pro Gly Ser Ala Pro
            275                 280                 285

Lys Thr His Gly Glu Ser Asp Lys Gly Pro His Thr Ser Pro Ser
            290                 295                 300

His Thr Leu Gly Lys Ala Ser Pro Ser Pro Ser Leu Ser Ser Tyr
            305                 310                 315

Ser Asp Pro Asp Ser Gly His Tyr Cys Gln Leu Gln Pro Pro Val
            320                 325                 330

Arg Gly Ser Arg Glu Trp Ala Ala Thr Glu Thr Ser Ser Gln Gln
            335                 340                 345

Ala Arg Ser Tyr Gly Glu Arg Leu Lys Glu Leu Ser Glu Asn Gly
            350                 355                 360

Ala Pro Glu Gly Asp Trp Gly Lys Thr Phe Thr Val Pro Ile Val
            365                 370                 375

Glu Val Thr Ser Ser Phe Asn Pro Ala Thr Phe Gln Ser Leu Leu
            380                 385                 390

Ile Pro Arg Asp Asn Arg Pro Leu Glu Val Gly Leu Leu Arg Lys
            395                 400                 405

Val Lys Glu Leu Leu Ala Glu Val Asp Ala Arg Thr Leu Ala Arg
            410                 415                 420

His Val Thr Lys Val Asp Cys Leu Val Ala Arg Ile Leu Gly Val
            425                 430                 435

Thr Lys Glu Met Gln Thr Leu Met Gly Val Arg Trp Gly Met Glu
            440                 445                 450

Leu Leu Thr Leu Pro His Gly Arg Gln Leu Arg Leu Asp Leu Leu
            455                 460                 465

Glu Arg Phe His Thr Met Ser Ile Met Leu Ala Val Asp Ile Leu
            470                 475                 480

Gly Cys Thr Gly Ser Ala Glu Glu Arg Ala Ala Leu Leu His Lys
            485                 490                 495

Thr Ile Gln Leu Ala Ala Glu Leu Arg Gly Thr Met Gly Asn Met
            500                 505                 510

Phe Ser Phe Ala Ala Val Met Gly Ala Leu Asp Met Ala Gln Ile
            515                 520                 525

Ser Arg Leu Glu Gln Thr Trp Val Thr Leu Arg Gln Arg His Thr
            530                 535                 540

FIG. 19B

```
Glu Gly Ala Ile Leu Tyr Glu Lys Lys Leu Lys Pro Phe Leu Lys
                545             550             555

Ser Leu Asn Glu Gly Lys Glu Gly Pro Pro Leu Ser Asn Thr Thr
                560             565             570

Phe Pro His Val Leu Pro Leu Ile Thr Leu Leu Glu Cys Asp Ser
                575             580             585

Ala Pro Pro Glu Gly Pro Glu Pro Trp Gly Ser Thr Glu His Gly
                590             595             600

Val Glu Val Val Leu Ala His Leu Glu Ala Ala Arg Thr Val Ala
                605             610             615

His His Gly Gly Leu Tyr His Thr Asn Ala Glu Val Lys Leu Gln
                620             625             630

Gly Phe Gln Ala Arg Pro Glu Leu Leu Glu Val Phe Ser Thr Glu
                635             640             645

Phe Gln Met Arg Leu Leu Trp Gly Ser Gln Gly Ala Ser Ser Ser
                650             655             660

Gln Ala Arg Arg Tyr Glu Lys Phe Asp Lys Val Leu Thr Ala Leu
                665             670             675

Ser His Lys Leu Glu Pro Ala Val Arg Ser Ser Glu Leu
                680             685             688
```

FIG. 19C

| | | |
|---|---|---|
| 201 | 1 | ------------------------------------------------MQ |
| 309 | 1 | MTAVGRRCPALGSRGAAGEPEAGSDYVKFSKEKYILDSSPEKLHKELEEE |
| DNA40556 | 1 | ---------------AAGEPEAGSDYVKFSKEKYILDSSPEKLHKELEEE |
| | | |
| 201 | 3 | VPQDGEDLAGQPWYHGLLSRQKAEALLQQDGDFLVRASGSRGGNPVISCR |
| 309 | 51 | LKLSSTDLRSHAWYHGRIPREVSETLVQRNGDFLIRDSLTSLGDYVLTCR |
| DNA40556 | 36 | LKLSSTDLRSHAWYHGRIPREVSETLVQRNGDFLIRDSLTSLGDYVLTCR |
| | | |
| 201 | 53 | WRGSALHFEVFRVALRPRPGRPTALFQLEDEQFPSIPALVHSYMTGRRPL |
| 309 | 101 | WRNQALHFKINKVVVKAGESYTHIQYLFEQESFDHVPALVRYHVGSRKAV |
| DNA40556 | 86 | WRNQALHFKINKVVVKAGESYTHIQYLFEQESFDHVPALVRYHVGSRKAV |
| | | |
| 201 | 103 | SQATGAVVSRPVTWQGPLRRSFSEDTLMDGPARIEPLRARKWSNS----- |
| 309 | 151 | SEQSGAIIYCPVNRTFPLRYLEASYGLGQGSSKPASPVSPSGPKGSHMKR |
| DNA40556 | 136 | SEQSGAIIYCPVNRTFPLRYLEASYGLGQGSSKPASPVSPSGPKGSHMKR |
| | | |
| 201 | 148 | ------------------------------------------QP----- |
| 309 | 201 | RSVTMTDGLTADKVTRSDGCPTSTSLPRPRDSIRSCALSMDQIPDLHSPM |
| DNA40556 | 186 | RSVTMTDGLTADKVTRSDGCPTSTSLPRPRDSIRSCALSMDQIPDLHSPM |
| | | |
| 201 | 150 | --------ADLAHMGRSREDPAGMEASTMPISALPRTSSDPVLLKAPAP |
| 309 | 251 | SPISESPSSPAYSTVTRVHAAPAAPSATALPASPVARCSSEPQLCPGSAP |
| DNA40556 | 236 | SPISESPSSPAYSTVTRVHAAPAAPSATALPASPVARRSSEPQLCPGSAP |
| | | |
| 201 | 191 | LGTVADSLRASDGQLQAKAPTKP-PRTPSFELPDASERPPTYCELVPRVP |
| 309 | 301 | KTHGESDKGPHTSPSHTLGKASPSPSLSSYSDPDSG----HYCQLPPVR |
| DNA40556 | 286 | KTHGESDKGPHTSPSHTLGKASPSPSLSSYSDPDSG----HYCQLPPVR |
| | | |
| 201 | 240 | SVQGTSPSQSCPEPEAPWWEAEEDEEE---------ENRCFTRPQAEISF |
| 309 | 347 | GSREWAATETSSQQARSYGERLKELSENGAPEGDWGKTFTVPIVEVTSSF |
| DNA40556 | 332 | GSREWAATETSSQQARSYGERLKELSENGAPEGDWGKTFTVPIVEVTSSF |
| | | |
| 201 | 281 | CPHDAPSCLLGPQNRPLEPQVLHTLRGLFLEHHPGSTALHLLLVDCQATG |
| 309 | 397 | NPATFQSLLIPRDNRPLEVGLLRKVKELLAEVDARTLARHVTKVDCLVAR |
| DNA40556 | 382 | NPATFQSLLIPRDNRPLEVGLLRKVKELLAEVDARTLARHVTKVDCLVAR |
| | | |
| 201 | 331 | LLGVTRDQRGNMGVSSGLELLTLPHGHHLRLELLERHQTLALAGALAVLG |
| 309 | 447 | ILGVTKEMQTLMGVRWGMELLTLPHGRQLRLDLLERFHTMSIMLAVDILG |
| DNA40556 | 432 | ILGVTKEMQTLMGVRWGMELLTLPHGRQLRLDLLERFHTMSIMLAVDILG |
| | | |
| 201 | 381 | CSGPLEERAAALRGLVELALALRPGAAGDLPGLAAVMGALLMPQVSRLEH |
| 309 | 497 | CTGSAEERAALLHKTIQLAAELRG-TMGNMFSFAAVMGALDMAQISRLEQ |
| DNA40556 | 482 | CTGSAEERAALLHKTIQLAAELRG-TMGNMFSFAAVMGALDMAQISRLEQ |
| | | |
| 201 | 431 | TWRQLRRSHTEAALAFEQELKPLMRALDEGAGPCDPGEVALPHVAPMVRL |
| 309 | 546 | TWVTLRQRHTEGAILYEKKLKPFLKSLNEGKEGPPLSNTTFPHVLPLITL |
| DNA40556 | 531 | TWVTLRQRHTEGAILYEKKLKPFLKSLNEGKEGPPLSNTTFPHVLPLITL |
| | | |
| 201 | 481 | LEGE-------EVAGPLDESCERLLRTLHGARHMVRDAPKFRKVAAQRLR |
| 309 | 596 | LECDSAPPEGPEPWGSTEHGVEVVLAHLEAARTVAHHGGLYHTNAEVKLQ |
| DNA40556 | 581 | LECDSAPPEGPEPWGSTEHGVEVVLAHLEAARTVAHHGGLYHTNAEVKLQ |
| | | |
| 201 | 524 | GFRPNPELREALTTGFVRRLLWGSRGAGAPRAERFEKFQRVLGVLSQRLE |
| 309 | 646 | GFQARPELLEVFSTEFQMRLLWGSQGASSSQARRYEKFDKVLTALSHKLE |
| DNA40556 | 631 | GFQARPELLEVFSTEFQMRLLWGSQGASSSQARRYEKFDKVLTALSHKLE |
| | | |
| 201 | 574 | PDR----- |
| 309 | 696 | PAVRSSEL |
| DNA40556 | 681 | PAVRSSEL |

FIG. 20

SEQUENCE LISTING

```
<160> NUMBER OF SEQ ID NOS:  35

<210> SEQ ID NO 1
<211> LENGTH: 576
<212> TYPE: PRT
<213> ORGANISM: Homo sapiens

<400> SEQUENCE: 1

Met Gln Val Pro Gln Asp Gly Glu Asp Leu Ala Gly Gln Pro Trp
  1               5                  10                  15

Tyr His Gly Leu Leu Ser Arg Gln Lys Ala Glu Ala Leu Leu Gln
                 20                  25                  30

Gln Asp Gly Asp Phe Leu Val Arg Ala Ser Gly Ser Arg Gly Gly
                 35                  40                  45

Asn Pro Val Ile Ser Cys Arg Trp Arg Gly Ser Ala Leu His Phe
                 50                  55                  60

Glu Val Phe Arg Val Ala Leu Arg Pro Arg Pro Gly Arg Pro Thr
                 65                  70                  75

Ala Leu Phe Gln Leu Glu Asp Glu Gln Phe Pro Ser Ile Pro Ala
                 80                  85                  90

Leu Val His Ser Tyr Met Thr Gly Arg Arg Pro Leu Ser Gln Ala
                 95                 100                 105

Thr Gly Ala Val Val Ser Arg Pro Val Thr Trp Gln Gly Pro Leu
                110                 115                 120

Arg Arg Ser Phe Ser Glu Asp Thr Leu Met Asp Gly Pro Ala Arg
                125                 130                 135

Ile Glu Pro Leu Arg Ala Arg Lys Trp Ser Asn Ser Gln Pro Ala
                140                 145                 150

Asp Leu Ala His Met Gly Arg Ser Arg Glu Asp Pro Ala Gly Met
                155                 160                 165
```

-continued

```
Glu Ala Ser Thr Met Pro Ile Ser Ala Leu Pro Arg Thr Ser Ser
                170                 175                 180

Asp Pro Val Leu Leu Lys Ala Pro Ala Pro Leu Gly Thr Val Ala
            185                 190                 195

Asp Ser Leu Arg Ala Ser Asp Gly Gln Leu Gln Ala Lys Ala Pro
            200                 205                 210

Thr Lys Pro Pro Arg Thr Pro Ser Phe Glu Leu Pro Asp Ala Ser
            215                 220                 225

Glu Arg Pro Pro Thr Tyr Cys Glu Leu Val Pro Arg Val Pro Ser
            230                 235                 240

Val Gln Gly Thr Ser Pro Ser Gln Ser Cys Pro Glu Pro Glu Ala
            245                 250                 255

Pro Trp Trp Glu Ala Glu Asp Glu Glu Glu Asn Arg Cys
            260                 265                 270

Phe Thr Arg Pro Gln Ala Glu Ile Ser Phe Cys Pro His Asp Ala
            275                 280                 285

Pro Ser Cys Leu Leu Gly Pro Gln Asn Arg Pro Leu Glu Pro Gln
            290                 295                 300

Val Leu His Thr Leu Arg Gly Leu Phe Leu Glu His His Pro Gly
            305                 310                 315

Ser Thr Ala Leu His Leu Leu Val Asp Cys Gln Ala Thr Gly
            320                 325                 330

Leu Leu Gly Val Thr Arg Asp Gln Arg Gly Asn Met Gly Val Ser
            335                 340                 345

Ser Gly Leu Glu Leu Leu Thr Leu Pro His Gly His His Leu Arg
            350                 355                 360

Leu Glu Leu Leu Glu Arg His Gln Thr Leu Ala Leu Ala Gly Ala
            365                 370                 375

Leu Ala Val Leu Gly Cys Ser Gly Pro Leu Glu Glu Arg Ala Ala
            380                 385                 390

Ala Leu Arg Gly Leu Val Glu Leu Ala Leu Ala Leu Arg Pro Gly
            395                 400                 405

Ala Ala Gly Asp Leu Pro Gly Leu Ala Ala Val Met Gly Ala Leu
            410                 415                 420

Leu Met Pro Gln Val Ser Arg Leu Glu His Thr Trp Arg Gln Leu
            425                 430                 435

Arg Arg Ser His Thr Glu Ala Ala Leu Ala Phe Glu Gln Glu Leu
            440                 445                 450

Lys Pro Leu Met Arg Ala Leu Asp Glu Gly Ala Gly Pro Cys Asp
            455                 460                 465

Pro Gly Glu Val Ala Leu Pro His Val Ala Pro Met Val Arg Leu
            470                 475                 480

Leu Glu Gly Glu Glu Val Ala Gly Pro Leu Asp Glu Ser Cys Glu
            485                 490                 495

Arg Leu Leu Arg Thr Leu His Gly Ala Arg His Met Val Arg Asp
            500                 505                 510

Ala Pro Lys Phe Arg Lys Val Ala Ala Gln Arg Leu Arg Gly Phe
            515                 520                 525

Arg Pro Asn Pro Glu Leu Arg Glu Ala Leu Thr Thr Gly Phe Val
            530                 535                 540

Arg Arg Leu Leu Trp Gly Ser Arg Gly Ala Gly Ala Pro Arg Ala
            545                 550                 555

Glu Arg Phe Glu Lys Phe Gln Arg Val Leu Gly Val Leu Ser Gln
```

```
                560               565               570
Arg Leu Glu Pro Asp Arg
            575

<210> SEQ ID NO 2
<211> LENGTH: 2413
<212> TYPE: DNA
<213> ORGANISM: Homo sapiens

<400> SEQUENCE: 2
cgggggtgac agcagcccgg agccgcggag cctcagcttc cgcctggacc           50
cagcctcgtg ggagccccgc gggtcctgcc cagatgtgga agactgaggc          100
ctgttgaaag tgcagagctc agccctggca ccctctgttc ccaagagctc          150 c   atg cag gtg cca cag gat gga gaa gac ctt gct ggc             187
    Met Gln Val Pro Gln Asp Gly Glu Asp Leu Ala Gly
    1               5                   10 caa ccc tgg tac cac ggc ctc ctg tcc cgc cag aag gct             226
Gln Pro Trp Tyr His Gly Leu Leu Ser Arg Gln Lys Ala
            15                  20                  25 gaa gct ctt ctt cag caa gat ggc gac ttc ctg gtt cgc             265
Glu Ala Leu Leu Gln Gln Asp Gly Asp Phe Leu Val Arg
                30                  35 gcc tct ggg tcc cgt ggg ggc aac ccc gtg atc tcc tgc             304
Ala Ser Gly Ser Arg Gly Gly Asn Pro Val Ile Ser Cys
    40                  45                  50 cgc tgg cgg ggc tca gcc ctc cat ttt gag gtg ttc cgt             343
Arg Trp Arg Gly Ser Ala Leu His Phe Glu Val Phe Arg
                55                  60 gtg gcc ctg cgt ccc cgg cca ggc cga ccc aca gcc ctc             382
Val Ala Leu Arg Pro Arg Pro Gly Arg Pro Thr Ala Leu
65                  70                  75 ttt caa ctg gag gat gag caa ttc ccc agc ata ccg gct             421
Phe Gln Leu Glu Asp Glu Gln Phe Pro Ser Ile Pro Ala
            80                  85                  90 ctg gtt cac agt tat atg aca ggc agg cgc cca ctg tcc             460
Leu Val His Ser Tyr Met Thr Gly Arg Arg Pro Leu Ser
                95                  100 cag gcc aca ggg gct gtg gtc tcc agg cct gtg act tgg             499
Gln Ala Thr Gly Ala Val Val Ser Arg Pro Val Thr Trp
    105                 110                 115 cag ggg cct ctg cga cgc agc ttt agc gag gac acc ctg             538
Gln Gly Pro Leu Arg Arg Ser Phe Ser Glu Asp Thr Leu
                120                 125 atg gat ggc cca gct cgg ata gag cct ctc agg gca agg             577
Met Asp Gly Pro Ala Arg Ile Glu Pro Leu Arg Ala Arg
130                 135                 140 aag tgg agc aac agt cag cct gca gat ttg gca cat atg             616
Lys Trp Ser Asn Ser Gln Pro Ala Asp Leu Ala His Met
            145                 150                 155 ggg cgg tca aga gaa gac ccc gct ggg atg gaa gcc tcc             655
Gly Arg Ser Arg Glu Asp Pro Ala Gly Met Glu Ala Ser
                160                 165 acc atg ccc ata tct gcc ttg ccc cga acg agc agt gac             694
Thr Met Pro Ile Ser Ala Leu Pro Arg Thr Ser Ser Asp
    170                 175                 180 ccg gtg ttg ctg aag gcc cct gct ccc ctg gga act gtt             733
Pro Val Leu Leu Lys Ala Pro Ala Pro Leu Gly Thr Val
                185                 190
```

-continued

| | |
|---|---|
| gcc gac agt ctc agg gcc tcc gat ggg cag ctt caa gcc<br>Ala Asp Ser Leu Arg Ala Ser Asp Gly Gln Leu Gln Ala<br>195    200     205 | 772 |
| aag gca cca acg aag ccc ccc cgg aca ccc tcc ttc gaa<br>Lys Ala Pro Thr Lys Pro Pro Arg Thr Pro Ser Phe Glu<br>210    215     220 | 811 |
| ctg cct gat gcc tct gaa cgt ccc ccg acg tac tgc gag<br>Leu Pro Asp Ala Ser Glu Arg Pro Pro Thr Tyr Cys Glu<br>225     230 | 850 |
| ctg gtg ccc cga gtg ccc agt gtc cag gga aca tcc ccg<br>Leu Val Pro Arg Val Pro Ser Val Gln Gly Thr Ser Pro<br>235    240     245 | 889 |
| agc caa agc tgc cca gag cca gag gcc cca tgg tgg gag<br>Ser Gln Ser Cys Pro Glu Pro Glu Ala Pro Trp Trp Glu<br>250    255 | 928 |
| gcc gag gag gat gag gag gaa gag aat aga tgt ttt aca<br>Ala Glu Glu Asp Glu Glu Glu Glu Asn Arg Cys Phe Thr<br>260    265     270 | 967 |
| aga cca cag gct gag atc tct ttc tgc ccc cat gat gcc<br>Arg Pro Gln Ala Glu Ile Ser Phe Cys Pro His Asp Ala<br>275    280     285 | 1006 |
| ccc tcc tgc ctg ctg ggc ccc cag aat cgg ccc ctg gaa<br>Pro Ser Cys Leu Leu Gly Pro Gln Asn Arg Pro Leu Glu<br>290    295 | 1045 |
| ccc caa gtc ctg cat acc ctc cgt ggc ctg ttc ctg gag<br>Pro Gln Val Leu His Thr Leu Arg Gly Leu Phe Leu Glu<br>300    305     310 | 1084 |
| cac cat cct ggg agc acc gcc ctt cac ctg cta ttg gta<br>His His Pro Gly Ser Thr Ala Leu His Leu Leu Leu Val<br>315    320 | 1123 |
| gac tgc cag gcc aca ggc ctc ctg gga gtg acc aga gat<br>Asp Cys Gln Ala Thr Gly Leu Leu Gly Val Thr Arg Asp<br>325    330     335 | 1162 |
| cag cgg ggc aac atg gga gtc tca tct ggc ctg gag ctg<br>Gln Arg Gly Asn Met Gly Val Ser Ser Gly Leu Glu Leu<br>340    345     350 | 1201 |
| ctc act ctt ccc cat gga cac cac ttg agg ttg gaa ctg<br>Leu Thr Leu Pro His Gly His His Leu Arg Leu Glu Leu<br>355    360 | 1240 |
| ctg gag agg cat cag aca ctg gcg ctg gcc ggg gcg ctg<br>Leu Glu Arg His Gln Thr Leu Ala Leu Ala Gly Ala Leu<br>365    370     375 | 1279 |
| gcg gtg ctg ggc tgc tcg ggg ccg ctg gag gag cgc gca<br>Ala Val Leu Gly Cys Ser Gly Pro Leu Glu Glu Arg Ala<br>380    385 | 1318 |
| gcc gca ctg agg gga ctg gta gag ctg gcg ctg gcg ctg<br>Ala Ala Leu Arg Gly Leu Val Glu Leu Ala Leu Ala Leu<br>390    395     400 | 1357 |
| cgg cca ggg gcg gcg ggg gac ctg ccc ggg ctg gct gca<br>Arg Pro Gly Ala Ala Gly Asp Leu Pro Gly Leu Ala Ala<br>405    410     415 | 1396 |
| gtc atg ggc gcc ctg ctc atg ccc cag gtg tcc cgg ttg<br>Val Met Gly Ala Leu Leu Met Pro Gln Val Ser Arg Leu<br>420    425 | 1435 |
| gag cac acg tgg cgc cag ctc cga agg agc cac acg gag<br>Glu His Thr Trp Arg Gln Leu Arg Arg Ser His Thr Glu<br>430    435     440 | 1474 |
| gct gcg ctg gcc ttt gag cag gag ctg aag ccg ctg atg<br>Ala Ala Leu Ala Phe Glu Gln Glu Leu Lys Pro Leu Met<br>445    450 | 1513 |

```
cgg gct ctg gat gag ggc gct gga ccc tgc gac ccc ggc              1552
Arg Ala Leu Asp Glu Gly Ala Gly Pro Cys Asp Pro Gly
455             460                 465 gag gtg gcg ctg ccg cac gtg gca ccc atg gtt cgc cta              1591
Glu Val Ala Leu Pro His Val Ala Pro Met Val Arg Leu
        470                 475                 480 ctg gag ggc gag gaa gtc gcg ggg ccg ctg gac gag agc              1630
Leu Glu Gly Glu Glu Val Ala Gly Pro Leu Asp Glu Ser
                485                 490 tgt gag cgg ctg ttg cgc acc ctg cac ggg gcg cgt cac              1669
Cys Glu Arg Leu Leu Arg Thr Leu His Gly Ala Arg His
    495                 500                 505 atg gtc cgg gac gca ccc aaa ttc cgc aag gtg gca gcc              1708
Met Val Arg Asp Ala Pro Lys Phe Arg Lys Val Ala Ala
            510                 515 cag cgc ctg cga gga ttc cgg cct aac ccg gag ctg agg              1747
Gln Arg Leu Arg Gly Phe Arg Pro Asn Pro Glu Leu Arg
520             525                 530 gag gcc ctg acc acc ggc ttc gtg cgg agg ctg ctc tgg              1786
Glu Ala Leu Thr Thr Gly Phe Val Arg Arg Leu Leu Trp
        535                 540                 545 ggt agc cgg ggc gcg gga gct ccg cgc gct gaa cgc ttt              1825
Gly Ser Arg Gly Ala Gly Ala Pro Arg Ala Glu Arg Phe
                550                 555 gag aag ttc cag cgc gtc ctc ggc gtc ctg tcg cag cgc              1864
Glu Lys Phe Gln Arg Val Leu Gly Val Leu Ser Gln Arg
    560                 565                 570 ctg gag cct gac cgc t gagagcgcag acacccttct tcacacccgg           1910
Leu Glu Pro Asp Arg
            575 576 gaccccagg tttttgcgaa ccccagaaga gaccaaagga gtcgtcccag             1960
gctcctcgcg cctcaggtgg aatcctgccc tgtgcctcac agaagaggtg            2010
gggaccgcag tcagggtcac ctggaccatg gtgaacatgt gacctgcaga            2060
tctggcatca gaggccagag ttcaaatgtg actccacctc ttaaaagccg            2110
tgatttctag cagttgactt cacctctgtg tcggccttta acaaaatcat            2160
agccatacag cagctcaggc ctgtaatctc agcactttgg gaggccgagg            2210
cggaaggaag gcttgaggcc aggagttcaa gaccagccag gcaacatgg             2260 tgagacctca tctctacaaa aactgaaaaa taaaaaactt ttaaaaatg             2310 taaaaaaaaa aaaaaagg cggccgcgac tctagagtcg acctgcagaa              2360
gcttggccgc catggcccaa cttgtttatt gcagcttata atggttacaa            2410
ata                                                              2413
```

<210> SEQ ID NO 3
<211> LENGTH: 501
<212> TYPE: PRT
<213> ORGANISM: Homo sapiens

<400> SEQUENCE: 3

```
Met Gln Asp Arg Arg Ala Leu Ser Leu Lys Ala His Gln Ser Glu
1               5                   10                  15

Ser Tyr Leu Pro Ile Gly Cys Lys Leu Pro Pro Gln Ser Ser Gly
                20                  25                  30

Val Asp Thr Ser Pro Cys Pro Asn Ser Pro Val Phe Arg Thr Gly
                35                  40                  45
```

```
Ser Glu Pro Ala Leu Ser Pro Ala Val Val Arg Arg Val Ser Ser
                 50                  55                  60

Asp Ala Arg Ala Gly Glu Ala Leu Arg Gly Ser Asp Ser Gln Leu
                 65                  70                  75

Cys Pro Lys Pro Pro Lys Pro Cys Lys Val Pro Phe Leu Lys
                 80                  85                  90

Val Pro Ser Ser Pro Ser Ala Trp Leu Asn Ser Glu Ala Asn Tyr
                 95                 100                 105

Cys Glu Leu Asn Pro Ala Phe Ala Thr Gly Cys Gly Arg Gly Ala
                110                 115                 120

Lys Leu Pro Ser Cys Ala Gln Gly Ser His Thr Glu Leu Leu Thr
                125                 130                 135

Ala Lys Gln Asn Glu Ala Pro Gly Pro Arg Asn Ser Gly Val Asn
                140                 145                 150

Tyr Leu Ile Leu Asp Asp Asp Arg Glu Arg Pro Trp Glu Pro
                155                 160                 165

Ala Ala Ala Gln Met Glu Lys Gly Gln Trp Asp Lys Gly Glu Phe
                170                 175                 180

Val Thr Pro Leu Leu Glu Thr Val Ser Ser Phe Arg Pro Asn Glu
                185                 190                 195

Phe Glu Ser Lys Phe Leu Pro Pro Glu Asn Lys Pro Leu Glu Thr
                200                 205                 210

Ala Met Leu Lys Arg Ala Lys Glu Leu Phe Thr Asn Asn Asp Pro
                215                 220                 225

Lys Val Ile Ala Gln His Val Leu Ser Met Asp Cys Arg Val Ala
                230                 235                 240

Arg Ile Leu Gly Val Ser Glu Glu Met Arg Arg Asn Met Gly Val
                245                 250                 255

Ser Ser Gly Leu Glu Leu Ile Thr Leu Pro His Gly His Gln Leu
                260                 265                 270

Arg Leu Asp Ile Ile Glu Arg His Asn Thr Met Ala Ile Gly Ile
                275                 280                 285

Ala Val Asp Ile Leu Gly Cys Thr Gly Thr Leu Glu Asp Arg Ala
                290                 295                 300

Ala Thr Leu Ser Lys Ile Ile Gln Val Ala Val Glu Leu Lys Asp
                305                 310                 315

Ser Met Gly Asp Leu Tyr Ser Phe Ser Ala Leu Met Lys Ala Leu
                320                 325                 330

Glu Met Pro Gln Ile Thr Arg Leu Glu Lys Thr Trp Thr Ala Leu
                335                 340                 345

Arg His Gln Tyr Thr Gln Thr Ala Ile Leu Tyr Glu Lys Gln Leu
                350                 355                 360

Lys Pro Phe Ser Lys Leu Leu His Glu Gly Arg Glu Ser Thr Cys
                365                 370                 375

Val Pro Pro Asn Asn Val Ser Val Pro Leu Leu Met Pro Leu Val
                380                 385                 390

Thr Leu Met Glu Arg Gln Ala Val Thr Phe Glu Gly Thr Asp Met
                395                 400                 405

Trp Glu Lys Asn Asp Gln Ser Cys Glu Ile Met Leu Asn His Leu
                410                 415                 420

Ala Thr Ala Arg Phe Met Ala Glu Ala Ala Asp Ser Tyr Arg Met
                425                 430                 435
```

-continued

```
Asn Ala Glu Arg Ile Leu Ala Gly Phe Gln Pro Asp Glu Met
                440                 445                 450

Asn Glu Ile Cys Lys Thr Glu Phe Gln Met Arg Leu Leu Trp Gly
                455                 460                 465

Ser Lys Gly Ala Gln Val Asn Gln Thr Glu Arg Tyr Glu Lys Phe
                470                 475                 480

Asn Gln Ile Leu Thr Ala Leu Ser Arg Lys Leu Glu Pro Pro
                485                 490                 495

Val Lys Gln Ala Glu Leu
                500
```

<210> SEQ ID NO 4
<211> LENGTH: 2174
<212> TYPE: DNA
<213> ORGANISM: Homo sapiens

<400> SEQUENCE: 4

```
ggcccctgga gtccagccgc agtggtcact gcttaaatat cacttctcgg            50
gagatatttc cttttgtaat ttgccctcgg tcttgtctta tcttcgaaag           100
gttgctggaa tttctctgtt ccttggagtt tgggggtttt ttgatttgtt           150
ttttctttgg tgcttgtaaa gaaacaaaga aaagagtggg agccagcccg           200
cctgcctgga tcac atg cag gac aga aga gcc ttg tcc ctc              241
              Met Gln Asp Arg Arg Ala Leu Ser Leu
                1               5 aaa gcc cac cag tca gag agc tac ctg ccg att ggc tgc              280
Lys Ala His Gln Ser Glu Ser Tyr Leu Pro Ile Gly Cys
 10              15                  20 aag ctg cca cct cag tcc tcg ggt gtg gac aca agc ccc              319
Lys Leu Pro Pro Gln Ser Ser Gly Val Asp Thr Ser Pro
     25                  30                  35 tgc cca aac tca cct gtg ttc agg acg gga agc gag cct              358
Cys Pro Asn Ser Pro Val Phe Arg Thr Gly Ser Glu Pro
             40                  45 gcc ctg agc cca gca gtg gtt cgg agg gtc tcc tca gac              397
Ala Leu Ser Pro Ala Val Val Arg Arg Val Ser Ser Asp
 50                  55                  60 gcc agg gct ggg gag gcg ctg agg gga tca gac agt caa              436
Ala Arg Ala Gly Glu Ala Leu Arg Gly Ser Asp Ser Gln
         65                  70 ctg tgc cct aag ccc ccg cct aag ccc tgc aag gtg ccg              475
Leu Cys Pro Lys Pro Pro Pro Lys Pro Cys Lys Val Pro
 75              80                  85 ttc ctc aag gtt ccc tcg tct ccc tct gcc tgg ctc aac              514
Phe Leu Lys Val Pro Ser Ser Pro Ser Ala Trp Leu Asn
     90                  95                 100 tca gag gcc aac tac tgt gaa ctg aac cca gcg ttt gcc              553
Ser Glu Ala Asn Tyr Cys Glu Leu Asn Pro Ala Phe Ala
             105                 110 aca ggc tgc ggc agg gga gca aag cta ccc tca tgt gcc              592
Thr Gly Cys Gly Arg Gly Ala Lys Leu Pro Ser Cys Ala
 115                 120                 125 cag gga agc cac aca gaa ctg ctc aca gcc aag cag aat              631
Gln Gly Ser His Thr Glu Leu Leu Thr Ala Lys Gln Asn
             130                 135 gag gcg cca ggt ccc cgg aac tct ggc gtc aac tac ttg              670
Glu Ala Pro Gly Pro Arg Asn Ser Gly Val Asn Tyr Leu
 140                 145                 150
```

```
atc ctt gat gat gat gac agg gaa aga cct tgg gaa cct        709
Ile Leu Asp Asp Asp Asp Arg Glu Arg Pro Trp Glu Pro
        155                 160                 165 gcg gca gct cag atg gag aag ggg cag tgg gac aag ggc        748
Ala Ala Ala Gln Met Glu Lys Gly Gln Trp Asp Lys Gly
            170                 175 gag ttt gtg acg ccc ctc ctg gag act gtc tcc tcc ttc        787
Glu Phe Val Thr Pro Leu Leu Glu Thr Val Ser Ser Phe
180                 185                 190 agg ccc aac gag ttt gag tca aag ttc ctt ccc cct gag        826
Arg Pro Asn Glu Phe Glu Ser Lys Phe Leu Pro Pro Glu
        195                 200 aat aag ccc ctg gaa aca gca atg ttg aaa cgt gca aaa        865
Asn Lys Pro Leu Glu Thr Ala Met Leu Lys Arg Ala Lys
205                 210                 215 gaa ctg ttc acc aac aac gac ccc aag gtc atc gcc cag        904
Glu Leu Phe Thr Asn Asn Asp Pro Lys Val Ile Ala Gln
            220                 225                 230 cac gta ctg agc atg gac tgc agg gtt gct agg ata ctt        943
His Val Leu Ser Met Asp Cys Arg Val Ala Arg Ile Leu
                235                 240 gga gtc tct gaa gag atg agg agg aac atg ggg gtg agc        982
Gly Val Ser Glu Glu Met Arg Arg Asn Met Gly Val Ser
245                 250                 255 tca ggc ctg gaa ctc att acc ttg cct cac gga cac cag       1021
Ser Gly Leu Glu Leu Ile Thr Leu Pro His Gly His Gln
            260                 265 ctg cgc ctg gac ata att gaa aga cac aac aca atg gcc       1060
Leu Arg Leu Asp Ile Ile Glu Arg His Asn Thr Met Ala
270                 275                 280 atc ggc att gca gtg gac att ctg gga tgc acg ggc act       1099
Ile Gly Ile Ala Val Asp Ile Leu Gly Cys Thr Gly Thr
            285                 290                 295 ttg gag gac cga gcg gcc act ctg agt aag atc atc cag       1138
Leu Glu Asp Arg Ala Ala Thr Leu Ser Lys Ile Ile Gln
                300                 305 gtg gcg gtg gaa ctg aag gat tcc atg ggg gac ctc tat       1177
Val Ala Val Glu Leu Lys Asp Ser Met Gly Asp Leu Tyr
310                 315                 320 tcc ttc tca gct ctc atg aaa gcc ctg gaa atg cca cag       1216
Ser Phe Ser Ala Leu Met Lys Ala Leu Glu Met Pro Gln
            325                 330 atc aca agg tta gaa aag acg tgg act gct ctg cgg cac       1255
Ile Thr Arg Leu Glu Lys Thr Trp Thr Ala Leu Arg His
335                 340                 345 cag tac acc caa act gcc att ctc tat gag aaa cag ctg       1294
Gln Tyr Thr Gln Thr Ala Ile Leu Tyr Glu Lys Gln Leu
        350                 355                 360 aag ccc ttc agc aaa ctc ctg cat gaa ggc aga gag tcc       1333
Lys Pro Phe Ser Lys Leu Leu His Glu Gly Arg Glu Ser
                365                 370 aca tgt gtt ccc cca aac aat gta tca gtc cca ctg ctg       1372
Thr Cys Val Pro Pro Asn Asn Val Ser Val Pro Leu Leu
375                 380                 385 atg ccg ctt gtg acg tta atg gag cgc cag gct gtg act       1411
Met Pro Leu Val Thr Leu Met Glu Arg Gln Ala Val Thr
            390                 395 ttt gaa gga acc gac atg tgg gaa aaa aac gac cag agc       1450
Phe Glu Gly Thr Asp Met Trp Glu Lys Asn Asp Gln Ser
400                 405                 410
```

-continued

```
tgt gaa atc atg ctg aac cat ttg gca aca gcg cga ttc              1489
Cys Glu Ile Met Leu Asn His Leu Ala Thr Ala Arg Phe
        415                 420                 425 atg gcc gag gct gca gac agc tac cgg atg aat gct gag              1528
Met Ala Glu Ala Ala Asp Ser Tyr Arg Met Asn Ala Glu
                430                 435 agg atc ctg gca ggt ttt caa cca gat gaa gaa atg aat              1567
Arg Ile Leu Ala Gly Phe Gln Pro Asp Glu Glu Met Asn
440                 445                 450 gaa atc tgc aag act gaa ttt caa atg cga ttg cta tgg              1606
Glu Ile Cys Lys Thr Glu Phe Gln Met Arg Leu Leu Trp
                455                 460 ggc agc aaa ggt gca caa gtc aat cag aca gag aga tat              1645
Gly Ser Lys Gly Ala Gln Val Asn Gln Thr Glu Arg Tyr
465                 470                 475 gag aaa ttc aac cag att tta act gcc ctc tcg cgt aaa              1684
Glu Lys Phe Asn Gln Ile Leu Thr Ala Leu Ser Arg Lys
                480                 485                 490 ttg gaa cct cct cct gta aag cag gca gag ctt tga                  1720
Leu Glu Pro Pro Pro Val Lys Gln Ala Glu Leu
                495                 500 501 taactctcca gagaaccttt agaatatctt ttcaagtttc cccagcttca           1770
tctttgggaa agcttactgt ttttgataaa gtaataatgt gcaaatctga           1820
caatatacaa gcttttagta tccacaggat attaaacgtg taaattgcac           1870
agagcacact tatttatgaa ttgtctaaag ttactactga ttttaaaatg           1920
aataatttat tattaaggta actactgcta atgttgatca gcaaatttaa           1970
gagaagacct agctatgttg gctggttgct ttctattatc atggtatttg           2020
accatttttag ttttaattcc atgtcagata agtgtaaata gaagagttta          2070
aaagcatgaa acatttcaga aggtatcagt tatatgatat tctttaaaca           2120
aatatgaaaa atgtaaatac tcatgaatga aaatacatct ttttgtgaaa           2170
cagt                                                             2174
```

<210> SEQ ID NO 5
<211> LENGTH: 703
<212> TYPE: PRT
<213> ORGANISM: Homo sapiens

<400> SEQUENCE: 5

```
Met Thr Ala Val Gly Arg Arg Cys Pro Ala Leu Gly Ser Arg Gly
  1               5                  10                  15

Ala Ala Gly Glu Pro Glu Ala Gly Ser Asp Tyr Val Lys Phe Ser
                 20                  25                  30

Lys Glu Lys Tyr Ile Leu Asp Ser Ser Pro Glu Lys Leu His Lys
             35                  40                  45

Glu Leu Glu Glu Glu Leu Lys Leu Ser Ser Thr Asp Leu Arg Ser
             50                  55                  60

His Ala Trp Tyr His Gly Arg Ile Pro Arg Glu Val Ser Glu Thr
             65                  70                  75

Leu Val Gln Arg Asn Gly Asp Phe Leu Ile Arg Asp Ser Leu Thr
             80                  85                  90

Ser Leu Gly Asp Tyr Val Leu Thr Cys Arg Trp Arg Asn Gln Ala
             95                 100                 105

Leu His Phe Lys Ile Asn Lys Val Val Val Lys Ala Gly Glu Ser
```

```
                        110                 115                 120
Tyr Thr His Ile Gln Tyr Leu Phe Glu Gln Glu Ser Phe Asp His
                125                 130                 135
Val Pro Ala Leu Val Arg Tyr His Val Gly Ser Arg Lys Ala Val
                140                 145                 150
Ser Glu Gln Ser Gly Ala Ile Ile Tyr Cys Pro Val Asn Arg Thr
                155                 160                 165
Phe Pro Leu Arg Tyr Leu Glu Ala Ser Tyr Gly Leu Gly Gln Gly
                170                 175                 180
Ser Ser Lys Pro Ala Ser Pro Val Ser Pro Ser Gly Pro Lys Gly
                185                 190                 195
Ser His Met Lys Arg Arg Ser Val Thr Met Thr Asp Gly Leu Thr
                200                 205                 210
Ala Asp Lys Val Thr Arg Ser Asp Gly Cys Pro Thr Ser Thr Ser
                215                 220                 225
Leu Pro Arg Pro Arg Asp Ser Ile Arg Ser Cys Ala Leu Ser Met
                230                 235                 240
Asp Gln Ile Pro Asp Leu His Ser Pro Met Ser Pro Ile Ser Glu
                245                 250                 255
Ser Pro Ser Ser Pro Ala Tyr Ser Thr Val Thr Arg Val His Ala
                260                 265                 270
Ala Pro Ala Ala Pro Ser Ala Thr Ala Leu Pro Ala Ser Pro Val
                275                 280                 285
Ala Arg Cys Ser Ser Glu Pro Gln Leu Cys Pro Gly Ser Ala Pro
                290                 295                 300
Lys Thr His Gly Glu Ser Asp Lys Gly Pro His Thr Ser Pro Ser
                305                 310                 315
His Thr Leu Gly Lys Ala Ser Pro Ser Pro Ser Leu Ser Ser Tyr
                320                 325                 330
Ser Asp Pro Asp Ser Gly His Tyr Cys Gln Leu Gln Pro Pro Val
                335                 340                 345
Arg Gly Ser Arg Glu Trp Ala Ala Thr Glu Thr Ser Ser Gln Gln
                350                 355                 360
Ala Arg Ser Tyr Gly Glu Arg Leu Lys Glu Leu Ser Glu Asn Gly
                365                 370                 375
Ala Pro Glu Gly Asp Trp Gly Lys Thr Phe Thr Val Pro Ile Val
                380                 385                 390
Glu Val Thr Ser Ser Phe Asn Pro Ala Thr Phe Gln Ser Leu Leu
                395                 400                 405
Ile Pro Arg Asp Asn Arg Pro Leu Glu Val Gly Leu Leu Arg Lys
                410                 415                 420
Val Lys Glu Leu Leu Ala Glu Val Asp Ala Arg Thr Leu Ala Arg
                425                 430                 435
His Val Thr Lys Val Asp Cys Leu Val Ala Arg Ile Leu Gly Val
                440                 445                 450
Thr Lys Glu Met Gln Thr Leu Met Gly Val Arg Trp Gly Met Glu
                455                 460                 465
Leu Leu Thr Leu Pro His Gly Arg Gln Leu Arg Leu Asp Leu Leu
                470                 475                 480
Glu Arg Phe His Thr Met Ser Ile Met Leu Ala Val Asp Ile Leu
                485                 490                 495
Gly Cys Thr Gly Ser Ala Glu Glu Arg Ala Ala Leu Leu His Lys
                500                 505                 510
```

```
Thr Ile Gln Leu Ala Ala Glu Leu Arg Gly Thr Met Gly Asn Met
            515                 520                 525

Phe Ser Phe Ala Ala Val Met Gly Ala Leu Asp Met Ala Gln Ile
            530                 535                 540

Ser Arg Leu Glu Gln Thr Trp Val Thr Leu Arg Gln Arg His Thr
            545                 550                 555

Glu Gly Ala Ile Leu Tyr Glu Lys Lys Leu Lys Pro Phe Leu Lys
            560                 565                 570

Ser Leu Asn Glu Gly Lys Glu Gly Pro Pro Leu Ser Asn Thr Thr
            575                 580                 585

Phe Pro His Val Leu Pro Leu Ile Thr Leu Leu Glu Cys Asp Ser
            590                 595                 600

Ala Pro Pro Glu Gly Pro Glu Pro Trp Gly Ser Thr Glu His Gly
            605                 610                 615

Val Glu Val Val Leu Ala His Leu Glu Ala Ala Arg Thr Val Ala
            620                 625                 630

His His Gly Gly Leu Tyr His Thr Asn Ala Glu Val Lys Leu Gln
            635                 640                 645

Gly Phe Gln Ala Arg Pro Glu Leu Leu Glu Val Phe Ser Thr Glu
            650                 655                 660

Phe Gln Met Arg Leu Leu Trp Gly Ser Gln Gly Ala Ser Ser Ser
            665                 670                 675

Gln Ala Arg Arg Tyr Glu Lys Phe Asp Lys Val Leu Thr Ala Leu
            680                 685                 690

Ser His Lys Leu Glu Pro Ala Val Arg Ser Ser Glu Leu
            695                 700

<210> SEQ ID NO 6
<211> LENGTH: 2153
<212> TYPE: DNA
<213> ORGANISM: Homo sapiens

<400> SEQUENCE: 6
taggaggtcc ccgggttgcc ggcggcgaca gcgggggaag c   atg               44
                                              Met
                                                1 act gct gtg ggc cga agg tgc ccc gcg ctg ggg tcc cga                83
Thr Ala Val Gly Arg Arg Cys Pro Ala Leu Gly Ser Arg
            5                   10 ggg gct gct gga gag cca gag gct ggc agc gac tat gtg              122
Gly Ala Ala Gly Glu Pro Glu Ala Gly Ser Asp Tyr Val
 15                  20                  25 aag ttc tcc aag gag aag tac atc ctg gac tca tcg cca              161
Lys Phe Ser Lys Glu Lys Tyr Ile Leu Asp Ser Ser Pro
         30                  35                  40 gag aaa ctc cac aag gaa ttg gag gag gag ctc aaa ctc              200
Glu Lys Leu His Lys Glu Leu Glu Glu Glu Leu Lys Leu
             45                  50 agc agc acg gat ctc cgc agc cat gcc tgg tac cat ggc              239
Ser Ser Thr Asp Leu Arg Ser His Ala Trp Tyr His Gly
     55                  60                  65 cgc atc ccc cga gag gtc tcg gag acc ttg gta caa cgc              278
Arg Ile Pro Arg Glu Val Ser Glu Thr Leu Val Gln Arg
         70                  75 aac ggc gac ttc ctc atc cgg gac tcg ctc acc agc ctg              317
Asn Gly Asp Phe Leu Ile Arg Asp Ser Leu Thr Ser Leu
 80                  85                  90
```

-continued

```
ggc gac tat gtg ctc acg tgc cgc tgg cgc aac cag gcc                    356
Gly Asp Tyr Val Leu Thr Cys Arg Trp Arg Asn Gln Ala
         95                 100                 105 ttg cac ttc aag atc aac aag gtg gtg gtg aag gca ggc                    395
Leu His Phe Lys Ile Asn Lys Val Val Val Lys Ala Gly
                    110                 115 gag agc tac aca cac atc cag tac ctg ttt gag cag gag                    434
Glu Ser Tyr Thr His Ile Gln Tyr Leu Phe Glu Gln Glu
        120                 125                 130 agc ttt gac cac gtg ccc gcc ctc gtg cgc tat cat gtg                    473
Ser Phe Asp His Val Pro Ala Leu Val Arg Tyr His Val
            135                 140 ggc agc cgc aag gct gtg tca gag cag agt ggt gcc atc                    512
Gly Ser Arg Lys Ala Val Ser Glu Gln Ser Gly Ala Ile
145                 150                 155 atc tac tgc ccg gtg aac cgc acc ttc cca ctg cgc tac                    551
Ile Tyr Cys Pro Val Asn Arg Thr Phe Pro Leu Arg Tyr
                160                 165                 170 ctc gag gcc agc tat ggc ctg gga cag ggg agt agc aag                    590
Leu Glu Ala Ser Tyr Gly Leu Gly Gln Gly Ser Ser Lys
                    175                 180 cct gct agc ccc gtc agc ccc tca ggc ccc aag ggc agc                    629
Pro Ala Ser Pro Val Ser Pro Ser Gly Pro Lys Gly Ser
        185                 190                 195 cac atg aag cgg cgc agc gtc acc atg acc gat ggg ctc                    668
His Met Lys Arg Arg Ser Val Thr Met Thr Asp Gly Leu
            200                 205 act gct gac aag gtc acc cgc agc gat ggc tgc ccc acc                    707
Thr Ala Asp Lys Val Thr Arg Ser Asp Gly Cys Pro Thr
210                 215                 220 agt acg tcg ctg ccc cgc cct cgg gac tcc atc cgc agc                    746
Ser Thr Ser Leu Pro Arg Pro Arg Asp Ser Ile Arg Ser
                225                 230                 235 tgt gcc ctc agc atg gac cag atc cca gac ctg cac tca                    785
Cys Ala Leu Ser Met Asp Gln Ile Pro Asp Leu His Ser
                    240                 245 ccc atg tcg ccc atc tcc gag agc cct agc tcc cct gcc                    824
Pro Met Ser Pro Ile Ser Glu Ser Pro Ser Ser Pro Ala
        250                 255                 260 tac agc act gta acc cgt gtc cat gcc gcc cct gca gcc                    863
Tyr Ser Thr Val Thr Arg Val His Ala Ala Pro Ala Ala
            265                 270 cct tct gcc aca gca ttg cct gcc tcc cct gtc gcc cgc                    902
Pro Ser Ala Thr Ala Leu Pro Ala Ser Pro Val Ala Arg
275                 280                 285 tgt tcc agt gag ccc cag ctg tgt ccc gga agt gcc cca                    941
Cys Ser Ser Glu Pro Gln Leu Cys Pro Gly Ser Ala Pro
                290                 295                 300 aag acc cat ggg gag tca gac aag ggc ccc cac acc agc                    980
Lys Thr His Gly Glu Ser Asp Lys Gly Pro His Thr Ser
                    305                 310 ccc tcc cac acc ctt ggc aag gcc tcc ccg tca cca tca                   1019
Pro Ser His Thr Leu Gly Lys Ala Ser Pro Ser Pro Ser
        315                 320                 325 ctc agc agc tac agt gac ccg gac tct ggc cac tac tgc                   1058
Leu Ser Ser Tyr Ser Asp Pro Asp Ser Gly His Tyr Cys
            330                 335 cag ctc cag cct ccc gtg cgt ggc agc cga gag tgg gca                   1097
Gln Leu Gln Pro Pro Val Arg Gly Ser Arg Glu Trp Ala
```

-continued

```
      340                 345                 350
gcg act gag acc tcc agc cag cag gcc agg agc tat ggg          1136
Ala Thr Glu Thr Ser Ser Gln Gln Ala Arg Ser Tyr Gly
            355                 360                 365 gag agg cta aag gaa ctg tca gaa aat ggg gcc cct gaa          1175
Glu Arg Leu Lys Glu Leu Ser Glu Asn Gly Ala Pro Glu
                        370                 375 ggg gac tgg ggc aag acc ttc aca gtc ccc atc gtg gaa          1214
Gly Asp Trp Gly Lys Thr Phe Thr Val Pro Ile Val Glu
        380                 385                 390 gtc act tct tcc ttc aac ccg gcc acc ttc cag tca cta          1253
Val Thr Ser Ser Phe Asn Pro Ala Thr Phe Gln Ser Leu
                395                 400 ctg atc ccc agg gat aac cgg cca ctg gag gtg ggc ctt          1292
Leu Ile Pro Arg Asp Asn Arg Pro Leu Glu Val Gly Leu
405                 410                 415 ctg cgc aag gtc aag gag ctg ctg gca gaa gtg gat gcc          1331
Leu Arg Lys Val Lys Glu Leu Leu Ala Glu Val Asp Ala
            420                 425                 430 cgg acg ctg gcc cgg cat gtc acc aag gtg gac tgc ctg          1370
Arg Thr Leu Ala Arg His Val Thr Lys Val Asp Cys Leu
                        435                 440 gtt gct agg ata ctg ggc gtt acc aag gag atg cag acc          1409
Val Ala Arg Ile Leu Gly Val Thr Lys Glu Met Gln Thr
        445                 450                 455 cta atg gga gtc cgc tgg ggc atg gaa ctg ctc acc ctc          1448
Leu Met Gly Val Arg Trp Gly Met Glu Leu Leu Thr Leu
                460                 465 ccc cat ggc cgg cag cta cgc cta gac ctg ctg gaa agg          1487
Pro His Gly Arg Gln Leu Arg Leu Asp Leu Leu Glu Arg
470                 475                 480 ttc cac acc atg tcc atc atg ctg gcc gtg gac atc ctg          1526
Phe His Thr Met Ser Ile Met Leu Ala Val Asp Ile Leu
            485                 490                 495 ggc tgc acc ggc tct gcg gag gag cgg gca gcg ctg ctg          1565
Gly Cys Thr Gly Ser Ala Glu Glu Arg Ala Ala Leu Leu
                        500                 505 cac aag acc att cag ctg gcg gcc gag cta cgg ggg act          1604
His Lys Thr Ile Gln Leu Ala Ala Glu Leu Arg Gly Thr
        510                 515                 520 atg ggc aac atg ttc agc ttc gcg gcg gtc atg ggt gcc          1643
Met Gly Asn Met Phe Ser Phe Ala Ala Val Met Gly Ala
                525                 530 ctg gac atg gct cag att tct cgg ctg gag cag aca tgg          1682
Leu Asp Met Ala Gln Ile Ser Arg Leu Glu Gln Thr Trp
535                 540                 545 gtg acc ctg cgg cag cga cac aca gag ggt gcc atc ctg          1721
Val Thr Leu Arg Gln Arg His Thr Glu Gly Ala Ile Leu
            550                 555                 560 tac gag aag aag ctc aag cct ttt ctc aag agc ctc aac          1760
Tyr Glu Lys Lys Leu Lys Pro Phe Leu Lys Ser Leu Asn
                        565                 570 gag ggc aaa gaa ggc ccg ccg ctg agc aac acc acg ttt          1799
Glu Gly Lys Glu Gly Pro Pro Leu Ser Asn Thr Thr Phe
        575                 580                 585 cct cat gtg ctg ccc ctc atc acc ctg ctg gag tgt gac          1838
Pro His Val Leu Pro Leu Ile Thr Leu Leu Glu Cys Asp
                590                 595 tcg gcc cca cca gag ggc cct gag ccc tgg ggc agc acg          1877
Ser Ala Pro Pro Glu Gly Pro Glu Pro Trp Gly Ser Thr
```

```
Ser Ala Pro Pro Glu Gly Pro Glu Pro Trp Gly Ser Thr
600             605             610 gag cac ggc gtg gag gtg gtg ctg gct cac ctg gag gcc           1916
Glu His Gly Val Glu Val Val Leu Ala His Leu Glu Ala
        615             620             625 gcc cgc aca gtg gca cac cac gga ggc ctg tac cac acc           1955
Ala Arg Thr Val Ala His His Gly Gly Leu Tyr His Thr
                630             635 aat gct gaa gtc aag ctg cag ggg ttc cag gcc cgg ccg           1994
Asn Ala Glu Val Lys Leu Gln Gly Phe Gln Ala Arg Pro
640             645             650 gag ctc ctg gag gtg ttc agc acg gag ttc cag atg cgc           2033
Glu Leu Leu Glu Val Phe Ser Thr Glu Phe Gln Met Arg
        655             660 ctt ctc tgg ggc agt cag ggt gcc agc agc agc cag gcc           2072
Leu Leu Trp Gly Ser Gln Gly Ala Ser Ser Ser Gln Ala
665             670             675 cgg cgc tat gag aag ttc gac aag gtc ctc act gcc ctg           2111
Arg Arg Tyr Glu Lys Phe Asp Lys Val Leu Thr Ala Leu
        680             685             690 tcc cac aag ctg gaa cct gct gtc cgc tcc agc gag ctg           2150
Ser His Lys Leu Glu Pro Ala Val Arg Ser Ser Glu Leu
                695             700             703 tga                                                            2153

<210> SEQ ID NO 7
<211> LENGTH: 30
<212> TYPE: DNA
<213> ORGANISM: Artificial Sequence
<220> FEATURE:
<223> OTHER INFORMATION: Oligonucleotide Probe

<400> SEQUENCE: 7
actgaggcct gttgaaagtg cagagctcag                              30

<210> SEQ ID NO 8
<211> LENGTH: 18
<212> TYPE: DNA
<213> ORGANISM: Artificial Sequence
<220> FEATURE:
<223> OTHER INFORMATION: Oligonucleotide Probe

<400> SEQUENCE: 8
gctgaagaag agcttcag                                           18

<210> SEQ ID NO 9
<211> LENGTH: 48
<212> TYPE: DNA
<213> ORGANISM: Artificial Sequence
<220> FEATURE:
<223> OTHER INFORMATION: Oligonucleotide Probe

<400> SEQUENCE: 9
caatgccgat ggccattgtg ttgtgtcttt caattatgtc caggcgca          48

<210> SEQ ID NO 10
<211> LENGTH: 18
<212> TYPE: DNA
<213> ORGANISM: Artificial Sequence
<220> FEATURE:
<223> OTHER INFORMATION: Oligonucleotide Probe

<400> SEQUENCE: 10
```

-continued atcccagaat gtccactg                                                    18

<210> SEQ ID NO 11
<211> LENGTH: 50
<212> TYPE: DNA
<213> ORGANISM: Artificial Sequence
<220> FEATURE:
<223> OTHER INFORMATION: Oligonucleotide Probe

<400> SEQUENCE: 11
ggccagcatg atggacatgg tgtggaacct ttccagcagg tctaggcgta                 50

<210> SEQ ID NO 12
<211> LENGTH: 18
<212> TYPE: DNA
<213> ORGANISM: Artificial Sequence
<220> FEATURE:
<223> OTHER INFORMATION: Oligonucleotide Probe

<400> SEQUENCE: 12
ggtgcagccc aggatgtc                                                    18

<210> SEQ ID NO 13
<211> LENGTH: 254
<212> TYPE: DNA
<213> ORGANISM: Homo Sapien

<400> SEQUENCE: 13
gtggagggcg ggggtgacag cagcccggag ccgcggagcc tcagcttccg                 50
cctggaccca gcctcgtggg agcccgcgg gtcctgccca gatgtggaag                 100
actgaggcct gttgaaagtg cagagctcag ccctggcacc ctctgttccc                150
aagagctcca tgcaggtgcc acaggatgga gaagaccttg ctggccaacc                200
ttggtaccac ggcctcctgt cccgccagaa ggctgaagct cttcttcagc                250
aaaa                                                                  254

<210> SEQ ID NO 14
<211> LENGTH: 212
<212> TYPE: DNA
<213> ORGANISM: Homo Sapien
<220> FEATURE:
<221> NAME/KEY: unsure
<222> LOCATION: 59
<223> OTHER INFORMATION: unknown base

<400> SEQUENCE: 14
catcgcccag cacgtactga gcatggactg cagggttgct aggatacttg                 50
gagtctctna agagatgagg aggaacatgg gggtgagctc aggcctggaa                100
ctcattacct tgcctcacgg acaccagctg cgcctggaca taattgaaag                150
acacaacaca atggccatcg gcattgcagt ggacattctg ggatgcacgg                200
gcactttgga gg                                                         212

<210> SEQ ID NO 15
<211> LENGTH: 242
<212> TYPE: DNA
<213> ORGANISM: Homo Sapien
<220> FEATURE:
<221> NAME/KEY: unsure
<222> LOCATION: 204
<223> OTHER INFORMATION: unknown base

<400> SEQUENCE: 15

―continued

```
gctggcagaa gtggatgccc ggacgctggc ccggcatgtc accaaggtgg           50
actgcctggt tgctaggata ctgggcgtta ccaaggagat gcagaccta           100 atgggagtcc gctggggcat ggaactgctc accctccccc atggccggca         150
gctacgccta gacctgctgg aaaggttcca caccatgtcc atcatgctgg         200
ccgnggacat cctgggctgc accggctctg cggaggagcg gg                 242
```

<210> SEQ ID NO 16
<211> LENGTH: 99
<212> TYPE: PRT
<213> ORGANISM: Homo sapiens

<400> SEQUENCE: 16

```
Glu Gln Leu Arg Gly Glu Pro Trp Phe His Gly Lys Leu Ser Arg
 1               5                  10                  15

Arg Glu Ala Glu Ala Leu Leu Gln Leu Asn Gly Asp Phe Leu Val
                20                  25                  30

Arg Glu Ser Thr Thr Thr Pro Gly Gln Tyr Val Gly Leu Gln Ser
                35                  40                  45

Gly Gln Pro Lys His Leu Leu Leu Val Asp Pro Glu Gly Val Val
                50                  55                  60

Arg Thr Lys Asp His Arg Phe Glu Ser Val Ser His Leu Ile Ser
                65                  70                  75

Tyr His Met Asp Asn Pro Ile Ile Ser Ala Gly Ser Glu Leu Cys
                80                  85                  90

Leu Gln Gln Pro Val Glu Arg Lys Leu
                95
```

<210> SEQ ID NO 17
<211> LENGTH: 99
<212> TYPE: PRT
<213> ORGANISM: Homo sapiens

<400> SEQUENCE: 17

```
Glu Gln Leu Arg Gln Glu Pro Trp Tyr His Gly Arg Met Ser Arg
 1               5                  10                  15

Arg Ala Ala Glu Arg Met Leu Arg Ala Asp Gly Asp Phe Leu Val
                20                  25                  30

Arg Asp Ser Val Thr Asn Pro Gly Gln Tyr Val Gly Met His Ala
                35                  40                  45

Gly Gln Pro Lys His Leu Leu Leu Val Asp Pro Glu Gly Val Val
                50                  55                  60

Arg Thr Lys Asp Val Leu Phe Glu Ser Ile Ser His Leu Ile Asp
                65                  70                  75

His His Leu Gln Asn Pro Ile Val Ala Ala Glu Ser Glu Leu His
                80                  85                  90

Leu Arg Gly Val Val Ser Arg Glu Pro
                95
```

<210> SEQ ID NO 18
<211> LENGTH: 115
<212> TYPE: PRT
<213> ORGANISM: Homo sapiens

<400> SEQUENCE: 18

```
Lys Pro Leu His Glu Gln Leu Trp Tyr His Gly Ala Ile Pro Arg
 1               5                  10                  15
```

Ala Glu Val Ala Glu Leu Leu Val His Ser Gly Asp Phe Leu Val
                20                  25                  30

Arg Glu Ser Gln Gly Lys Gln Glu Tyr Val Val Leu Trp Asp Gly
            35                  40                  45

Leu Pro Arg His Phe Ile Ile Gln Ser Leu Asp Asn Leu Tyr Arg
        50                  55                  60

Leu Glu Gly Glu Gly Phe Pro Ser Ile Pro Leu Leu Ile Asp His
    65                  70                  75

Leu Leu Ser Thr Pro Leu Thr Lys Lys Ser Gly Val Val Leu His
                80                  85                  90

Arg Ala Val Pro Lys Asp Lys Trp Val Leu Asn His Glu Asp Leu
            95                 100                 105

Val Leu Gly Glu Gln Ile Gly Arg Gly Asn
        110                 115

<210> SEQ ID NO 19
<211> LENGTH: 8
<212> TYPE: PRT
<213> ORGANISM: Homo sapiens

<400> SEQUENCE: 19

Asp Tyr Lys Asp Asp Asp Asp Lys
 1               5

<210> SEQ ID NO 20
<211> LENGTH: 688
<212> TYPE: PRT
<213> ORGANISM: Homo Sapiens

<400> SEQUENCE: 20

Ala Ala Gly Glu Pro Glu Ala Gly Ser Asp Tyr Val Lys Phe Ser
 1               5                  10                  15

Lys Glu Lys Tyr Ile Leu Asp Ser Ser Pro Glu Lys Leu His Lys
                20                  25                  30

Glu Leu Glu Glu Glu Leu Lys Leu Ser Ser Thr Asp Leu Arg Ser
            35                  40                  45

His Ala Trp Tyr His Gly Arg Ile Pro Arg Glu Val Ser Glu Thr
        50                  55                  60

Leu Val Gln Arg Asn Gly Asp Phe Leu Ile Arg Asp Ser Leu Thr
    65                  70                  75

Ser Leu Gly Asp Tyr Val Leu Thr Cys Arg Trp Arg Asn Gln Ala
                80                  85                  90

Leu His Phe Lys Ile Asn Lys Val Val Lys Ala Gly Glu Ser
            95                 100                 105

Tyr Thr His Ile Gln Tyr Leu Phe Glu Gln Glu Ser Phe Asp His
        110                 115                 120

Val Pro Ala Leu Val Arg Tyr His Val Gly Ser Arg Lys Ala Val
    125                 130                 135

Ser Glu Gln Ser Gly Ala Ile Ile Tyr Cys Pro Val Asn Arg Thr
                140                 145                 150

Phe Pro Leu Arg Tyr Leu Glu Ala Ser Tyr Gly Leu Gly Gln Gly
            155                 160                 165

Ser Ser Lys Pro Ala Ser Pro Val Ser Pro Ser Gly Pro Lys Gly
        170                 175                 180

Ser His Met Lys Arg Arg Ser Val Thr Met Thr Asp Gly Leu Thr
    185                 190                 195

-continued

```
Ala Asp Lys Val Thr Arg Ser Asp Gly Cys Pro Thr Ser Thr Ser
            200                 205                 210
Leu Pro Arg Pro Arg Asp Ser Ile Arg Ser Cys Ala Leu Ser Met
            215                 220                 225
Asp Gln Ile Pro Asp Leu His Ser Pro Met Ser Pro Ile Ser Glu
            230                 235                 240
Ser Pro Ser Ser Pro Ala Tyr Ser Thr Val Thr Arg Val His Ala
            245                 250                 255
Ala Pro Ala Ala Pro Ser Ala Thr Ala Leu Pro Ala Ser Pro Val
            260                 265                 270
Ala Arg Arg Ser Ser Glu Pro Gln Leu Cys Pro Gly Ser Ala Pro
            275                 280                 285
Lys Thr His Gly Glu Ser Asp Lys Gly Pro His Thr Ser Pro Ser
            290                 295                 300
His Thr Leu Gly Lys Ala Ser Pro Ser Pro Ser Leu Ser Ser Tyr
            305                 310                 315
Ser Asp Pro Asp Ser Gly His Tyr Cys Gln Leu Gln Pro Pro Val
            320                 325                 330
Arg Gly Ser Arg Glu Trp Ala Ala Thr Glu Thr Ser Ser Gln Gln
            335                 340                 345
Ala Arg Ser Tyr Gly Glu Arg Leu Lys Glu Leu Ser Glu Asn Gly
            350                 355                 360
Ala Pro Glu Gly Asp Trp Gly Lys Thr Phe Thr Val Pro Ile Val
            365                 370                 375
Glu Val Thr Ser Ser Phe Asn Pro Ala Thr Phe Gln Ser Leu Leu
            380                 385                 390
Ile Pro Arg Asp Asn Arg Pro Leu Glu Val Gly Leu Leu Arg Lys
            395                 400                 405
Val Lys Glu Leu Leu Ala Glu Val Asp Ala Arg Thr Leu Ala Arg
            410                 415                 420
His Val Thr Lys Val Asp Cys Leu Val Ala Arg Ile Leu Gly Val
            425                 430                 435
Thr Lys Glu Met Gln Thr Leu Met Gly Val Arg Trp Gly Met Glu
            440                 445                 450
Leu Leu Thr Leu Pro His Gly Arg Gln Leu Arg Leu Asp Leu Leu
            455                 460                 465
Glu Arg Phe His Thr Met Ser Ile Met Leu Ala Val Asp Ile Leu
            470                 475                 480
Gly Cys Thr Gly Ser Ala Glu Glu Arg Ala Ala Leu Leu His Lys
            485                 490                 495
Thr Ile Gln Leu Ala Ala Glu Leu Arg Gly Thr Met Gly Asn Met
            500                 505                 510
Phe Ser Phe Ala Ala Val Met Gly Ala Leu Asp Met Ala Gln Ile
            515                 520                 525
Ser Arg Leu Glu Gln Thr Trp Val Thr Leu Arg Gln Arg His Thr
            530                 535                 540
Glu Gly Ala Ile Leu Tyr Glu Lys Lys Leu Lys Pro Phe Leu Lys
            545                 550                 555
Ser Leu Asn Glu Gly Lys Glu Gly Pro Pro Leu Ser Asn Thr Thr
            560                 565                 570
Phe Pro His Val Leu Pro Leu Ile Thr Leu Leu Glu Cys Asp Ser
            575                 580                 585
```

```
Ala Pro Pro Glu Gly Pro Glu Pro Trp Gly Ser Thr Glu His Gly
                590                 595                 600

Val Glu Val Val Leu Ala His Leu Glu Ala Ala Arg Thr Val Ala
                605                 610                 615

His His Gly Gly Leu Tyr His Thr Asn Ala Glu Val Lys Leu Gln
                620                 625                 630

Gly Phe Gln Ala Arg Pro Glu Leu Leu Glu Val Phe Ser Thr Glu
                635                 640                 645

Phe Gln Met Arg Leu Leu Trp Gly Ser Gln Gly Ala Ser Ser Ser
                650                 655                 660

Gln Ala Arg Arg Tyr Glu Lys Phe Asp Lys Val Leu Thr Ala Leu
                665                 670                 675

Ser His Lys Leu Glu Pro Ala Val Arg Ser Ser Glu Leu
                680                 685

<210> SEQ ID NO 21
<211> LENGTH: 576
<212> TYPE: PRT
<213> ORGANISM: Artificial Sequence
<220> FEATURE:
<223> OTHER INFORMATION: Mutation of SEQ ID NO:1

<400> SEQUENCE: 21

Met Gln Val Pro Gln Asp Gly Glu Asp Leu Ala Gly Gln Pro Trp
  1               5                  10                  15

Phe His Gly Leu Leu Ser Arg Gln Lys Ala Glu Ala Leu Leu Gln
                 20                  25                  30

Gln Asp Gly Asp Phe Leu Val Arg Ala Ser Gly Ser Arg Gly Gly
                 35                  40                  45

Asn Pro Val Ile Ser Cys Arg Trp Arg Gly Ser Ala Leu His Phe
                 50                  55                  60

Glu Val Phe Arg Val Ala Leu Arg Pro Arg Pro Gly Arg Pro Thr
                 65                  70                  75

Ala Leu Phe Gln Leu Glu Asp Glu Gln Phe Pro Ser Ile Pro Ala
                 80                  85                  90

Leu Val His Ser Tyr Met Thr Gly Arg Arg Pro Leu Ser Gln Ala
                 95                 100                 105

Thr Gly Ala Val Val Ser Arg Pro Val Thr Trp Gln Gly Pro Leu
                110                 115                 120

Arg Arg Ser Phe Ser Glu Asp Thr Leu Met Asp Gly Pro Ala Arg
                125                 130                 135

Ile Glu Pro Leu Arg Ala Arg Lys Trp Ser Asn Ser Gln Pro Ala
                140                 145                 150

Asp Leu Ala His Met Gly Arg Ser Arg Glu Asp Pro Ala Gly Met
                155                 160                 165

Glu Ala Ser Thr Met Pro Ile Ser Ala Leu Pro Arg Thr Ser Ser
                170                 175                 180

Asp Pro Val Leu Leu Lys Ala Pro Ala Pro Leu Gly Thr Val Ala
                185                 190                 195

Asp Ser Leu Arg Ala Ser Asp Gly Gln Leu Gln Ala Lys Ala Pro
                200                 205                 210

Thr Lys Pro Pro Arg Thr Pro Ser Phe Glu Leu Pro Asp Ala Ser
                215                 220                 225

Glu Arg Pro Pro Thr Tyr Cys Glu Leu Val Pro Arg Val Pro Ser
                230                 235                 240
```

-continued

```
Val Gln Gly Thr Ser Pro Ser Gln Ser Cys Pro Glu Pro Glu Ala
                245                 250                 255

Pro Trp Trp Glu Ala Glu Asp Glu Glu Glu Asn Arg Cys
        260                 265                 270

Phe Thr Arg Pro Gln Ala Glu Ile Ser Phe Cys Pro His Asp Ala
                275                 280                 285

Pro Ser Cys Leu Leu Gly Pro Gln Asn Arg Pro Leu Glu Pro Gln
                290                 295                 300

Val Leu His Thr Leu Arg Gly Leu Phe Leu Glu His His Pro Gly
                305                 310                 315

Ser Thr Ala Leu His Leu Leu Val Asp Cys Gln Ala Thr Gly
                320                 325                 330

Leu Leu Gly Val Thr Arg Asp Gln Arg Gly Asn Met Gly Val Ser
                335                 340                 345

Ser Gly Leu Glu Leu Leu Thr Leu Pro His Gly His His Leu Arg
                350                 355                 360

Leu Glu Leu Leu Glu Arg His Gln Thr Leu Ala Leu Ala Gly Ala
                365                 370                 375

Leu Ala Val Leu Gly Cys Ser Gly Pro Leu Glu Glu Arg Ala Ala
                380                 385                 390

Ala Leu Arg Gly Leu Val Glu Leu Ala Leu Ala Leu Arg Pro Gly
                395                 400                 405

Ala Ala Gly Asp Leu Pro Gly Leu Ala Ala Val Met Gly Ala Leu
                410                 415                 420

Leu Met Pro Gln Val Ser Arg Leu Glu His Thr Trp Arg Gln Leu
                425                 430                 435

Arg Arg Ser His Thr Glu Ala Ala Leu Ala Phe Glu Gln Glu Leu
                440                 445                 450

Lys Pro Leu Met Arg Ala Leu Asp Glu Gly Ala Gly Pro Cys Asp
                455                 460                 465

Pro Gly Glu Val Ala Leu Pro His Val Ala Pro Met Val Arg Leu
                470                 475                 480

Leu Glu Gly Glu Glu Val Ala Gly Pro Leu Asp Glu Ser Cys Glu
                485                 490                 495

Arg Leu Leu Arg Thr Leu His Gly Ala Arg His Met Val Arg Asp
                500                 505                 510

Ala Pro Lys Phe Arg Lys Val Ala Ala Gln Arg Leu Arg Gly Phe
                515                 520                 525

Arg Pro Asn Pro Glu Leu Arg Glu Ala Leu Thr Thr Gly Phe Val
                530                 535                 540

Arg Arg Leu Leu Trp Gly Ser Arg Gly Ala Gly Ala Pro Arg Ala
                545                 550                 555

Glu Arg Phe Glu Lys Phe Gln Arg Val Leu Gly Val Leu Ser Gln
                560                 565                 570

Arg Leu Glu Pro Asp Arg
                575
```

<210> SEQ ID NO 22
<211> LENGTH: 576
<212> TYPE: PRT
<213> ORGANISM: Artificial Sequence
<220> FEATURE:
<223> OTHER INFORMATION: Mutation of SEQ ID NO:1

<400> SEQUENCE: 22

-continued

```
Met Gln Val Pro Gln Asp Gly Glu Asp Leu Ala Gly Gln Pro Trp
 1               5                  10                  15

Tyr His Gly Leu Leu Ser Arg Gln Lys Ala Glu Ala Leu Leu Gln
            20                  25                  30

Gln Asp Gly Asp Phe Leu Val Arg Ala Ser Gly Ser Arg Gly Gly
            35                  40                  45

Asn Pro Val Ile Ser Cys Arg Trp Arg Gly Ser Ala Leu His Phe
            50                  55                  60

Glu Val Phe Arg Val Ala Leu Arg Pro Arg Pro Gly Arg Pro Thr
            65                  70                  75

Ala Leu Phe Gln Leu Glu Asp Glu Gln Phe Pro Ser Ile Pro Ala
            80                  85                  90

Leu Val His Ser Phe Met Thr Gly Arg Arg Pro Leu Ser Gln Ala
            95                 100                 105

Thr Gly Ala Val Val Ser Arg Pro Val Thr Trp Gln Gly Pro Leu
           110                 115                 120

Arg Arg Ser Phe Ser Glu Asp Thr Leu Met Asp Gly Pro Ala Arg
           125                 130                 135

Ile Glu Pro Leu Arg Ala Arg Lys Trp Ser Asn Ser Gln Pro Ala
           140                 145                 150

Asp Leu Ala His Met Gly Arg Ser Arg Glu Asp Pro Ala Gly Met
           155                 160                 165

Glu Ala Ser Thr Met Pro Ile Ser Ala Leu Pro Arg Thr Ser Ser
           170                 175                 180

Asp Pro Val Leu Leu Lys Ala Pro Ala Pro Leu Gly Thr Val Ala
           185                 190                 195

Asp Ser Leu Arg Ala Ser Asp Gly Gln Leu Gln Ala Lys Ala Pro
           200                 205                 210

Thr Lys Pro Pro Arg Thr Pro Ser Phe Glu Leu Pro Asp Ala Ser
           215                 220                 225

Glu Arg Pro Pro Thr Tyr Cys Glu Leu Val Pro Arg Val Pro Ser
           230                 235                 240

Val Gln Gly Thr Ser Pro Ser Gln Ser Cys Pro Glu Pro Glu Ala
           245                 250                 255

Pro Trp Trp Glu Ala Glu Glu Asp Glu Glu Glu Asn Arg Cys
           260                 265                 270

Phe Thr Arg Pro Gln Ala Glu Ile Ser Phe Cys Pro His Asp Ala
           275                 280                 285

Pro Ser Cys Leu Leu Gly Pro Gln Asn Arg Pro Leu Glu Pro Gln
           290                 295                 300

Val Leu His Thr Leu Arg Gly Leu Phe Leu Glu His Pro Gly
           305                 310                 315

Ser Thr Ala Leu His Leu Leu Val Asp Cys Gln Ala Thr Gly
           320                 325                 330

Leu Leu Gly Val Thr Arg Asp Gln Arg Gly Asn Met Gly Val Ser
           335                 340                 345

Ser Gly Leu Glu Leu Leu Thr Leu Pro His Gly His Leu Arg
           350                 355                 360

Leu Glu Leu Leu Glu Arg His Gln Thr Leu Ala Leu Ala Gly Ala
           365                 370                 375

Leu Ala Val Leu Gly Cys Ser Gly Pro Leu Glu Glu Arg Ala Ala
           380                 385                 390

Ala Leu Arg Gly Leu Val Glu Leu Ala Leu Ala Leu Arg Pro Gly
```

-continued

```
                 395                 400                 405

Ala Ala Gly Asp Leu Pro Gly Leu Ala Ala Val Met Gly Ala Leu
            410                 415                 420

Leu Met Pro Gln Val Ser Arg Leu Glu His Thr Trp Arg Gln Leu
        425                 430                 435

Arg Arg Ser His Thr Glu Ala Ala Leu Ala Phe Glu Gln Glu Leu
    440                 445                 450

Lys Pro Leu Met Arg Ala Leu Asp Glu Gly Ala Gly Pro Cys Asp
455                 460                 465

Pro Gly Glu Val Ala Leu Pro His Val Ala Pro Met Val Arg Leu
            470                 475                 480

Leu Glu Gly Glu Glu Val Ala Gly Pro Leu Asp Glu Ser Cys Glu
        485                 490                 495

Arg Leu Leu Arg Thr Leu His Gly Ala Arg His Met Val Arg Asp
    500                 505                 510

Ala Pro Lys Phe Arg Lys Val Ala Ala Gln Arg Leu Arg Gly Phe
515                 520                 525

Arg Pro Asn Pro Glu Leu Arg Glu Ala Leu Thr Thr Gly Phe Val
            530                 535                 540

Arg Arg Leu Leu Trp Gly Ser Arg Gly Ala Gly Ala Pro Arg Ala
        545                 550                 555

Glu Arg Phe Glu Lys Phe Gln Arg Val Leu Gly Val Leu Ser Gln
    560                 565                 570

Arg Leu Glu Pro Asp Arg
575

<210> SEQ ID NO 23
<211> LENGTH: 576
<212> TYPE: PRT
<213> ORGANISM: Artificial Sequence
<220> FEATURE:
<223> OTHER INFORMATION: Mutation of SEQ ID NO:1

<400> SEQUENCE: 23

Met Gln Val Pro Gln Asp Gly Glu Asp Leu Ala Gly Gln Pro Trp
  1               5                  10                  15

Tyr His Gly Leu Leu Ser Arg Gln Lys Ala Glu Ala Leu Leu Gln
             20                  25                  30

Gln Asp Gly Asp Phe Leu Val Arg Ala Ser Gly Ser Arg Gly Gly
         35                  40                  45

Asn Pro Val Ile Ser Cys Arg Trp Arg Gly Ser Ala Leu His Phe
     50                  55                  60

Glu Val Phe Arg Val Ala Leu Arg Pro Arg Pro Gly Arg Pro Thr
 65                  70                  75

Ala Leu Phe Gln Leu Glu Asp Glu Gln Phe Pro Ser Ile Pro Ala
             80                  85                  90

Leu Val His Ser Tyr Met Thr Gly Arg Arg Pro Leu Ser Gln Ala
         95                 100                 105

Thr Gly Ala Val Val Ser Arg Pro Val Thr Trp Gln Gly Pro Leu
    110                 115                 120

Arg Arg Ser Phe Ser Glu Asp Thr Leu Met Asp Gly Pro Ala Arg
125                 130                 135

Ile Glu Pro Leu Arg Ala Arg Lys Trp Ser Asn Ser Gln Pro Ala
            140                 145                 150

Asp Leu Ala His Met Gly Arg Ser Arg Glu Asp Pro Ala Gly Met
```

-continued

```
                    155                 160                 165
Glu Ala Ser Thr Met Pro Ile Ser Ala Leu Pro Arg Thr Ser Ser
                170                 175                 180
Asp Pro Val Leu Leu Lys Ala Pro Ala Pro Leu Gly Thr Val Ala
                185                 190                 195
Asp Ser Leu Arg Ala Ser Asp Gly Gln Leu Gln Ala Lys Ala Pro
                200                 205                 210
Thr Lys Pro Pro Arg Thr Pro Ser Phe Glu Leu Pro Asp Ala Ser
                215                 220                 225
Glu Arg Pro Pro Thr Phe Cys Glu Leu Val Pro Arg Val Pro Ser
                230                 235                 240
Val Gln Gly Thr Ser Pro Ser Gln Ser Cys Pro Glu Pro Glu Ala
                245                 250                 255
Pro Trp Trp Glu Ala Glu Asp Glu Glu Glu Asn Arg Cys
                260                 265                 270
Phe Thr Arg Pro Gln Ala Glu Ile Ser Phe Cys Pro His Asp Ala
                275                 280                 285
Pro Ser Cys Leu Leu Gly Pro Gln Asn Arg Pro Leu Glu Pro Gln
                290                 295                 300
Val Leu His Thr Leu Arg Gly Leu Phe Leu Glu His His Pro Gly
                305                 310                 315
Ser Thr Ala Leu His Leu Leu Val Asp Cys Gln Ala Thr Gly
                320                 325                 330
Leu Leu Gly Val Thr Arg Asp Gln Arg Gly Asn Met Gly Val Ser
                335                 340                 345
Ser Gly Leu Glu Leu Leu Thr Leu Pro His Gly His His Leu Arg
                350                 355                 360
Leu Glu Leu Leu Glu Arg His Gln Thr Leu Ala Leu Ala Gly Ala
                365                 370                 375
Leu Ala Val Leu Gly Cys Ser Gly Pro Leu Glu Glu Arg Ala Ala
                380                 385                 390
Ala Leu Arg Gly Leu Val Glu Leu Ala Leu Ala Leu Arg Pro Gly
                395                 400                 405
Ala Ala Gly Asp Leu Pro Gly Leu Ala Ala Val Met Gly Ala Leu
                410                 415                 420
Leu Met Pro Gln Val Ser Arg Leu Glu His Thr Trp Arg Gln Leu
                425                 430                 435
Arg Arg Ser His Thr Glu Ala Ala Leu Ala Phe Glu Gln Glu Leu
                440                 445                 450
Lys Pro Leu Met Arg Ala Leu Asp Glu Gly Ala Gly Pro Cys Asp
                455                 460                 465
Pro Gly Glu Val Ala Leu Pro His Val Ala Pro Met Val Arg Leu
                470                 475                 480
Leu Glu Gly Glu Glu Val Ala Gly Pro Leu Asp Glu Ser Cys Glu
                485                 490                 495
Arg Leu Leu Arg Thr Leu His Gly Ala Arg His Met Val Arg Asp
                500                 505                 510
Ala Pro Lys Phe Arg Lys Val Ala Ala Gln Arg Leu Arg Gly Phe
                515                 520                 525
Arg Pro Asn Pro Glu Leu Arg Glu Ala Leu Thr Thr Gly Phe Val
                530                 535                 540
Arg Arg Leu Leu Trp Gly Ser Arg Gly Ala Gly Ala Pro Arg Ala
                545                 550                 555
```

Glu Arg Phe Glu Lys Phe Gln Arg Val Leu Gly Val Leu Ser Gln
            560                 565                 570

Arg Leu Glu Pro Asp Arg
            575

<210> SEQ ID NO 24
<211> LENGTH: 20
<212> TYPE: DNA
<213> ORGANISM: Artificial Sequence
<220> FEATURE:
<223> OTHER INFORMATION: Oligonucleotide Probe

<400> SEQUENCE: 24
cgcagacacc cttcttcaca                                         20

<210> SEQ ID NO 25
<211> LENGTH: 22
<212> TYPE: DNA
<213> ORGANISM: Artificial Sequence
<220> FEATURE:
<223> OTHER INFORMATION: Oligonucleotide Probe

<400> SEQUENCE: 25
cgactccttt ggtctcttct gg                                      22

<210> SEQ ID NO 26
<211> LENGTH: 21
<212> TYPE: DNA
<213> ORGANISM: Artificial Sequence
<220> FEATURE:
<223> OTHER INFORMATION: Oligonucleotide Probe

<400> SEQUENCE: 26
ccgggacccc caggtttttg c                                       21

<210> SEQ ID NO 27
<211> LENGTH: 19
<212> TYPE: DNA
<213> ORGANISM: Artificial Sequence
<220> FEATURE:
<223> OTHER INFORMATION: Oligonucleotide Probe

<400> SEQUENCE: 27
agggtcctgc gtggactct                                          19

<210> SEQ ID NO 28
<211> LENGTH: 23
<212> TYPE: DNA
<213> ORGANISM: Artificial Sequence
<220> FEATURE:
<223> OTHER INFORMATION: Oligonucleotide Probe

<400> SEQUENCE: 28
tcctgttctt cctcaatgga gac                                     23

<210> SEQ ID NO 29
<211> LENGTH: 25
<212> TYPE: DNA
<213> ORGANISM: Artificial Sequence
<220> FEATURE:
<223> OTHER INFORMATION: Oligonucleotide Probe

<400> SEQUENCE: 29
ccatcccacc tgctacatgc tcacc                                   25

```
<210> SEQ ID NO 30
<211> LENGTH: 48
<212> TYPE: DNA
<213> ORGANISM: Artificial Sequence
<220> FEATURE:
<223> OTHER INFORMATION: Oligonucleotide Probe

<400> SEQUENCE: 30
ggattctaat acgactcact atagggcgcg gaggctgctc tggggtag                48

<210> SEQ ID NO 31
<211> LENGTH: 48
<212> TYPE: DNA
<213> ORGANISM: Artificial Sequence
<220> FEATURE:
<223> OTHER INFORMATION: Oligonucleotide Probe

<400> SEQUENCE: 31
ctatgaaatt aaccctcact aaagggatgt tgccctggct ggtcttga                48

<210> SEQ ID NO 32
<211> LENGTH: 48
<212> TYPE: DNA
<213> ORGANISM: Artificial Sequence
<220> FEATURE:
<223> OTHER INFORMATION: Oligonucleotide Probe

<400> SEQUENCE: 32
ggattctaat acgactcact atagggcatc tgccttgccc cgaacgag                48

<210> SEQ ID NO 33
<211> LENGTH: 48
<212> TYPE: DNA
<213> ORGANISM: Artificial Sequence
<220> FEATURE:
<223> OTHER INFORMATION: Oligonucleotide Probe

<400> SEQUENCE: 33
ctatgaaatt aaccctcact aaagggatca tccagagccc gcatcagc                48

<210> SEQ ID NO 34
<211> LENGTH: 48
<212> TYPE: DNA
<213> ORGANISM: Artificial Sequence
<220> FEATURE:
<223> OTHER INFORMATION: Oligonucleotide Probe

<400> SEQUENCE: 34
ggattctaat acgactcact atagggcaga tgtggaagac tgaggcct                48

<210> SEQ ID NO 35
<211> LENGTH: 49
<212> TYPE: DNA
<213> ORGANISM: Artificial Sequence
<220> FEATURE:
<223> OTHER INFORMATION: Oligonucleotide Probe

<400> SEQUENCE: 35
ctatgaaatt aaccctcact aaagggaata tgtgccaaat ctgcaggct               49
```

SH2 DOMAIN-CONTAINING PEPTIDES

This application is a 371 of PCT/US99/08847 filed Apr. 23, 1999 which claims benefit of provisional No. 60/082,767 filed Apr. 23, 1998, and 60/113,29 filed Dec. 22, 1998.

FIELD OF THE INVENTION

The present invention relates generally to the identification and isolation of novel DNA and to the recombinant production of novel polypeptides which are characterized by the presence of novel SH2-containing proteins (Nsp's).

BACKGROUND OF THE INVENTION

Interactions between ligands and the cognate cell surface receptors are critical for a variety of biological processes including maintenance of cellular and organism homeostasis, development, and tumorigenesis. Many of these ligands can activate multiple independent pathways and the strength of the activation of different pathways can be modulated by the presence or absence of signals generated by other receptors, Hostamsigil, et al., *Proc. Natl. Acad. Sci. USA* 91: 4854–58 (1994); Kanety et al., *J. Biol. Chem.* 270: 23780–84 (1995); Luttrell et al., *J. Biol. Chem.* 272: 4637–44 (1997). Adaptor molecules may be critical in integrating multiple signaling cascades and in determining the cell type specific response to extracellular stimuli. These adaptor proteins have no apparent catalytic activity. Rather, they contain one or more domains that mediate protein-protein or protein-lipid interactions. The most common conserved interaction domains in these adaptor molecules are Src homology (SH2), SH3, phosphotyrosine binding (PTB) and pleckstrin homology domains. [Reviewed in Pawson and Scott, *Science* 278: 2075–80 (1997)].

Signals generated by growth factors such as epidermal growth factor (EGF) or insulin growth factor-1 (IGF-1) through receptor tyrosine kinases (RTK) or by extracellular matrix components acting through the integrin receptors can induce cytoskeletal changes, Leventhal, et al., *J. Biol. Chem.* 272: 5214–18 (1997); Ojaniemi & Vuori, *J. Biol. Chem.* 272: 2443–47 (1996). There are also indications that RTKs can modulate intogrin signals and vice versa, Doerr & Jones, *J. Biol. Chem.* 271: 2443–47 (1996); Jones et al., *Proc. Natl. Acad. Sci. USA* 93: 2482–87 (1996); Knight et al., *J. Biol. Chem.* 270: 10199–203 (1995); Matsumoto et al., *Cancer Metas. Rev.* 14: 205–17 (1995). However the details of how RTKs signal to the cytoskelelal components have not been fully resolved. Further, while some adaptor proteins have a limited pattern of expression [Liu & Roth, *Proc. Natl. Acad. Sci. USA* 92: 10287–91 (1995), Nakamura et al., *Oncogene* 13: 1111–21 (1996)], many are ubiquitously expressed [Araki et al., *Diabetes* 42: 1041–54 (1993): Frantz et al., *J. Biol. Chem.* 272: 2659–67 (1997)]. Thus, it is not clear how biologically relevant outputs are modulated as cells differentiate.

Cancer is characterized by the increase in the number of abnormal, or neoplastic, cells derived from a normal tissue which proliferate to form a tumor mass, the invasion of adjacent tissues by these neoplastic tumor cells, and the generation of malignant cells which eventually spread via the blood or lymphatic system to regional lymph nodes and to distant sites (metastasis). In a cancerous state a cell proliferates under conditions in which normal cells would not grow. Cancer manifests itself in a wide variety of forms, characterized by different degrees of invasiveness and aggressiveness.

Alteration of gene expression is intimately related to the uncontrolled cell growth and de-differentiation which are a common feature of all cancers. The genomes of certain well studied tumors have been found to show decreased expression of recessive genes, usually referred to as tumor suppression genes, which would normally function to prevent malignant cell growth, and/or overexpression of certain dominant genes, such as oncogenes, that act to promote malignant growth. Each of these genetic changes appears to be responsible for importing some of the traits that, in aggregate, represent the full neoplastic phenotype (Hunter, *Cell* 64: 1129 [1991]; Bishop, *Cell* 64: 235–248 [1991]).

A well known mechanism of gene (eg. oncogene) overexpression in cancer cells is gene amplification. This is a process where in the chromosome of the ancestral cell multiple copies of a particular gene are produced. The process involves unscheduled replication of the region of chromosome comprising the gene, followed by recombination of the replicated segments back into the chromosome (Alitalo et al., *Adv. Cancer Res.* 47: 235–281 [1986]). It is believed that the overexpression of the gene parallels gene amplification, ie. is proportionate to the number of copies made.

Proto-oncogenes that encode growth factors and growth factor receptors have been identified to play important roles in the pathogenesis of various human malignancies, including breast cancer. For example, it has been found that the human ErbB2 gene (erbB2, also known as her2, or c-erbB-2), which encodes a 185-kd transmembrane glycoprotein receptor ($p185^{HER2}$; HER2) related to the epidermal growth factor receptor EGFR), is overexpressed in about 25% to 30% of human breast cancer (Slamon et al., *Science* 235: 177–182 [1987];Slamon et al., *Science* 244: 707–712 [1989]).

It has been reported that gene amplification of a proto-oncogene is an event typically involved in the more malignant forms of cancer, and could act as a predictor of clinical outcome (Schwab et al., *Genes Chromosomes Cancer* 1, 181–193 [1990]; Alitalo et al., supra). Thus, erbB2 overexpression is commonly regarded as a predictor of a poor prognosis, especially in patients with primary disease that involves axillary lymph nodes (Slamon et al., [1987] and [1989], supra; Ravdin and Chamness, *Gene* 159: 19–27 [1995]; and Hynes and Stern, *Biochem Biophys Acta* 1198: 165–184 [1994]), and has been linked to sensitivity and/or resistance to hormone therapy and chemotherapeutic regimens, including CMF (cyclophosphamide, methotrexate, and fluoruracil) and anthracyclines (Baselga et al., *Oncology* 11 (3 Suppl 1): 43–48 [1997]). However, despite the association of erbB2 overexpression with poor prognosis, the odds of HER2-positive patients responding clinically to treatment with taxanes were greater than three times those of HER2-negative patients. A recombinant humanized anti-ErbB2 (anti-HER2) monoclonal antibody (a humanized version of the murine anti-ErbB2 antibody 4D5, referred to as rhuMAb HER2 or Herceptin*) has been clinically active in patients with ErbB2-overexpressing metastatic breast cancers that had received extensive prior anticancer therapy. (Baseiga et al., *J. Clin. Oncol.* 14: 737–744 [1996]).

SUMMARY OF THE INVENTION

Applicants have identified cDNA clone (DNA30676, DNA40575, DNA61601)(SEQ ID NO:s 2, 4 & 6, respectively) that encodes a novel polypeptide, designated in the present application as "Nsp1, Nsp2 & Nsp3" (SEQ ID NOS: 1, 3 and 6), respectively.

In one embodiment, the invention provides an isolated nucleic acid molecule having at least about 80% sequence identity to (a) a DNA molecule encoding a polypeptide comprising the sequence of amino acids 1 to 576 of FIG. 1 (SEQ ID NO: 1), amino acids 1 to 501 of FIG. 2 (SEQ ID NO: 3) or amino acids 1 to 703 of FIG. 3 (SEQ ID NO: 5); or (b) the complement of the DNA molecule of (a). The sequence identity preferably is about 85%, more preferably about 90%, most preferably about 95%. In one aspect, the isolated nucleic acid has at least about 80%, preferably at least about 85%, more preferably at least about 90%, and most preferably at least about 95% sequence identity with a polypeptide having amino acid residues 1 to 576 of FIG. 1 (SEQ ID NO: 1), 1 to 501 of FIG. 2, (SEQ ID NO: 3), and 1 to 703 of FIG. 3 (SEQ ID NO: 5). Preferably, the greatest degree of identity occurs in the serine/proline rich domain (ie., amino acid residues 145–299 of SEQ ID NO: 1, amino acid residues 28–210 of SEQ ID NO: 3 and amino acids 181–415 of SEQ ID NO: 5). Alternatively, the greatest degree of identity occurs in the SH2 domain (i.e., amino acid residues 1–118 of SEQ ID NO: 1 and amino acid residues 50–166 of SEQ ID NO: 5). In a further embodiment, the isolated nucleic acid molecule comprises DNA encoding a PRO201, PRO308 or PRO309 polypeptide having amino acid residues: (a) 1 to 576 of FIG. 1 (SEQ ID NO: 1), (b) 1 to 501 of FIG. 2 (SEQ ID NO: 3), or (c) 1 to 703 of FIG. 3 (SEQ ID NO: 5); or is complementary to such encoding nucleic acid sequence, and remains stably bound to it under at least moderate, and optionally, under high stringency conditions. Preferably, said nucleic acid molecule hybridizes to DNA encoding a fragment within the region defined by amino acid residues: (a) 32–576 of FIG. 1 (SEQ ID NO:1) or (b) 1–424 or 506 to 703 of FIG. 3 (SEQ ID NO:5). In another aspect, the invention provides a nucleic acid of the full length protein of clones DNA30676-1223 (SEQ ID NO:2), DNA40575-1223 (SEQ ID NO:4) and DNA61601-1223 (SEQ ID NO:6), deposited with the ATCC under accession number ATCC 209567, ATCC 209565 and ATCC 209713, respectively, alternatively the coding sequence of clones DNA30676-1223 (SEQ ID NO:2), DNA40575-1223 (SEQ ID NO:4) and DNA61601-1223 (SEQ ID NO:6), deposited under accession number ATCC 209567, ATCC 209565 and ATTC 209713, respectively.

In yet another embodiment, the invention provides a vector comprising DNA encoding a PRO201, PRO308, or PRO309 polypeptide. A host cell comprising such a vector is also providied. By way of example, the host cells may be CHO cells, *E. coli*, or yeast. A process for producing PRO201, PRO308 or PRO309 polypeptides is further provided and comprises culturing host cells under conditions suitable for expression of PRO201, PRO308 or PRO309 and recovering the same from the cell culture.

In yet another embodiment, the invention provides isolated PRO201, PRO308 or PRO309 polypeptide. In particular, the invention provides isolated native sequence PRO201, PRO308 or PRO309 polypeptide, which in one embodiment, includes an amino acid sequence comprising residues 1 to 576 of FIG. 1 (SEQ ID NO: 1); 1 to 501 of FIG. 2 (SEQ ID NO: 3) or 1 to 703 of FIG. 3 (SEQ ID NO: 5). Native PRO201, PRO308 or PRO309 polypeptides with or without the initiating methionine are specifically included. Alternatively, the invention provides a PRO201, PRO308 or PRO309 polypeptide encoded by the nucleic acid deposited under accession number ATCC 209567, ATCC 209565 and ATTC209713, respectively.

In yet another embodiment, the invention provides chimeric molecules comprising a PRO201, PRO308 or PRO309 polypeptide fused to a heterologous polypeptide or amino acid sequence. An example of such a chimeric molecule comprises a PRO201, PRO308 or PRO309 polypeptide fused to an epitope tag sequence or an Fc region of an immunoglobulin.

In yet another embodiment, the invention provides for compounds and methods for developing antagonists against and agonists promoting the PRO201, PRO308 and/or PRO309 modulated cellular signaling. In particular, an antagonist of PRO201 (e.g., Nsp1, SEQ ID NO:1), PRO308 (e.g., Nsp2, SEQ ID NO:3) and/or PRO309 (e.g., Nsp3, SEQ ID NO:5) which blocks, inhibits and/or neutralizes the normal functioning of the latter compounds in cellular signaling, including both small bioorganic molecules and antisense nucleotides.

In yet another embodiment, the invention provides for alternatively spliced variants of PRO201, PRO308 or PRO309 (e g., DNA40556).

The present invention further concerns compositions and methods for the diagnosis and treatment of neoplastic cell growth and proliferation in mammals, including humans. The present invention is based on the identification of genes that are amplified in the genome of tumor cells. Such gene amplification is expected to be associated with the overexpression of the gene product and contribute to tumorigenesis. Accordingly, the proteins encoded by the amplified genes are believed to be useful targets for the diagnosis and/or treatment (including prevention) of certain cancers, and may act of predictors of the prognosis of tumor treatment.

In one embodiment, the present invention concerns an isolated antibody which binds a polypeptide which is designated PRO201 (e.g., Nsp1, SEQ ID NO:1), PRO308 (e.g., Nsp2, SEQ ID NO:3) or PRO309 (e.g., Nsp3, SEQ ID NO:5). In one aspect, the antibody induces death of a cell overexpressing a PRO201, PRO308 or PRO309 polypeptide. In another aspect, the antibody is a monoclonal antibody, which preferably has nonhuman complementarity determining region (CDR) residues and human framework region (FR) residues. The antibody may be labeled and may be immobilized on a solid support. In a further aspect, the antibody is an antibody fragment, a single-chain antibody, or an anti-idiotypic antibody.

In another embodiment, the invention concerns a composition comprising an antibody which binds a PRO201, PRO308 or PRO309 polypeptide in admixture with a pharmaceutically acceptable carrier. In one aspect, the composition comprises a therapeutically effective amount of the antibody. In another aspect, the composition comprises a further active ingredient, which may, for example, be a further antibody or a cytotoxic or chemotherapeutic agent. Preferably, the composition is sterile.

In a further embodiment, the invention concerns nucleic acid encoding an anti-PRO201, anti-PRO308 or anti-PRO309 antibody, and vectors and recombinant host cells comprising such nucleic acid.

In a still further embodiment, the invention concerns a method for producing an anti-PRO0201, anti-PRO308 or anti-PRO309 antibody by culturing a host cell transformed with nucleic acid encoding the antibody under conditions such that the antibody is expressed, and recovering the antibody from the cell culture.

The invention further concerns antagonists and agonists of a PRO201, PRO308 or PRO309 polypeptide that inhibit one or more of the functions or activities of the PRO201, PRO308 or PRO309 polypeptide.

In a further embodiment, the invention concerns isolated nucleic acid molecules that hybridize to the complement of the nucleic acid molecules encoding the PRO201, PRO308 or PRO309 polypeptides. The nucleic acid preferably is DNA, and hybridization preferably occurs under stringent conditions. Preferably, said nucleic acid molecule hybridizes to the region from nucleotide residues (a) about 245 to 2413 of FIG. 1 (SEQ ID NO:2) or (b) 1 to about 1312 or about 1555 to about 2150 of FIG. 3 (SEQ ID NO:6). Such nucleic acid molecules can act as antisense molecules of the amplified genes identified herein, which, in turn, can find use in the modulation of the respective amplified genes, or as antisense primers in amplification reactions. Furthermore, such sequences can be used as part of ribozyme and/or triple helix sequence which, in turn, may be used in regulation of the amplified genes.

In another embodiment, the invention concerns a method for determining the presence of a PRO201, PRO308 or PRO309 polypeptide comprising exposing a cell suspected of containing the PRO201, PRO308 or PRO309 polypeptide to an anti-PRO201, anti-PRO308 or anti-PRO309 antibody and determining binding of the antibody to the cell.

In yet another embodiment, the present invention concerns a method of diagnosing tumor in a mammal, comprising detecting the level of expression of a gene encoding a PRO201, PRO308 or PRO309 polypeptide (a) in a test sample of tissue cells obtained from the mammal, and (b) in a control sample of known normal tissue cells of the same cell type, wherein a higher expression level in the test sample indicates the presence of tumor in the mammal from which the test tissue cells were obtained.

In another embodiment, the present invention concerns a method of diagnosing tumor in a mammal, comprising (a) contacting an anti-PRO20 1, anti-PRO308 or anti-PRO309 antibody with a test sample of tissue cells obtained from the mammal, and (b) detecting the formation of a complex between the anti-PRO201, anti-PRO308 or anti-PRO309 antibody and the PRO201, PRO308 or PRO309 polypeptide in the test sample. The detection may be qualitative or quantitative, and may be performed in comparison with monitoring the complex formation in a control sample of known normal tissue cells of the same cell type. A larger quantity of complexes formed in the test sample indicates the presence of tumor in the mammal from which the test tissue cells were obtained. The antibody preferably carries a detectable label. Complex formation can be monitored, for example, by light microscopy, flow cytometry, fluorimetry, or other techniques known in the art.

The test sample is usually obtained from an individual suspected to have neoplastic cell growth or proliferation (e.g. cancerous cells).

In another embodiment, the present invention concerns a cancer diagnostic kit, comprising an anti-PRO201, anti-PRO308 or anti-PRO309 antibody and a carrier (e.g. a buffer) in suitable packaging. The kit preferably contains instructions for using the antibody to detect the PRO201, PRO308 or PRO309 polypeptide.

In yet another embodiment, the invention concerns a method for inhibiting the growth of tumor cells comprising exposing a cell which overexpresses a PRO201, PRO308 or PRO309 potypeptide to an effective amount of an agent inhibiting the expression and/or activity of the PRO201, PRO308 or PRO309 polypeptide. The agent preferably is an anti-PRO201, anti-PRO308 or anti-PRO309 antibody, a small organic and inorganic molecule, peptide, phosphopeptide, antisense or ribozyme molecule, or a triple helix molecule. In a specific aspect, the agent, e.g. anti-PRO201, anti-PRO308 or anti-PRO309 antibody induces cell death. In a further aspect, the tumor cells are further exposed to radiation treatment and/or a cytotoxic or chemotherapeutic agent.

In a further embodiment, the invention concerns an article of manufacture, comprising:

a container;

a label on the container; and a composition comprising an active agent contained within the container, wherein the composition is effective for inhibiting the growth of tumor cells, the label on the container indicates that the composition can be used for treating conditions characterized by overexpression of a PRO201, PRO308 or PRO309 polypeptide, and the active agent in the composition is an agent inhibiting the expression and/or activity of PRO201, PRO308 or PRO309 polypeptide. In a preferred aspect, the active agent is an anti-PRO201, anti-PRO308 or anti-PRO309 antibody.

A method for identifying a compound capable of inhibiting the expression and/or activity of a PRO201, PRO308 or PRO309 polypeptide, comprising contacting a candidate compound with a PRO201, PRO308 or PRO309 polypeptide under conditions and for a time sufficient to allow these two components to interact. In a specific aspect, either the candidate compound or the PRO201, PRO308 or PRO309 polypeptide is immobilized on a solid support.

BRIEF DESCRIPTION OF THE DRAWINGS

FIGS. 1A–1C show both the nucleic acid sequence of DNA30676 (SEQ ID NO:2) as well as the encoded amino acid sequence of a native sequence PRO201 (Nsp1) polypeptide (SEQ ID NO:1).

FIGS. 2A–2C show both the nucleic acid sequence of DNA40575 (SEQ ID NO:4) as well as the encoded amino acid sequence of a native sequence PRO308 (Nsp2) polypeptide (SEQ ID NO:3).

FIGS. 3A–3C show both the nucleic acid sequence of DNA61601 (SEQ ID NO:6) as well as the encoded amino acid sequence of a native sequence PRO309 (Nsp3) polypeptide (SEQ ID NO:5).

FIGS. 4A–C shows the sequences of 1328938 (SEQ ID NO:13), 104191 (SEQ ID NO:14) and 1651811(SEQ ID NO:15), respectively, of the (LIFESEQ® database, Incyte Pharmaceuticals, Palo Alto, Calif.), which were used to isolate the full length DNA30676 (SEQ ID NO:2), DNA40575 (SEQ ID NO:4) and DNA61601 (SEQ ID NO:6) nucleic acid sequences of the invention.

FIG. 5A shows the oligonucleotide sequences (SEQ ID NO:7, SEQ ID NO: 8) which were used in the isolation of DNA30676 (SEQ ID NO:2). FIG. 5B shows the oligonucleotide sequences (SEQ ID NO: 9, SEQ ID NO: 10) which were used in the isolation of DNA40575 (SEQ ID NO:4). FIG. 5C shows the oligonucieotide sequences (SEQ ID NO: 11, SEQ ID NO: 12) which were used in the isolation of DNA61601 (SEQ ID NO:6).

FIG. 6B show an actual comparison between the 3 sequences themselves introducing gaps, as necessary in order to maximize the overall degree of identity between the three sequences.

FIG. 7 shows the sequence of Nsp1 (SEQ ID NO:1) wherein the SH2 region is identified in bold and the prolines and serines of the P/S region are indicated in single and double underline, respectively.

FIG. 8 shows a comparison of Nsp1 (SEQ ID NO:1) with human Shc (SEQ ID NO:16), Sck (SEQ ID NO:17) and Fes (SEQ ID NO:18) proteins.

FIGS. 19A–19C shows DNA40556 (SEQ ID NO:20) a splice variant of DNA30676 (SEQ ID NO:2) which was also found to be amplified in various lung and colon tumors.

FIG. 20 is a comparison of Nsp1 (SEQ ID NO:2), Nsp2 (SEQ ID NO:4) and the protein sequence encoded by DNA40556 (SEQ ID NO:20).

DETAILED DESCRIPTION OF THE PREFERRED EMBODIMENTS

I. Definitions

Figure 6A:
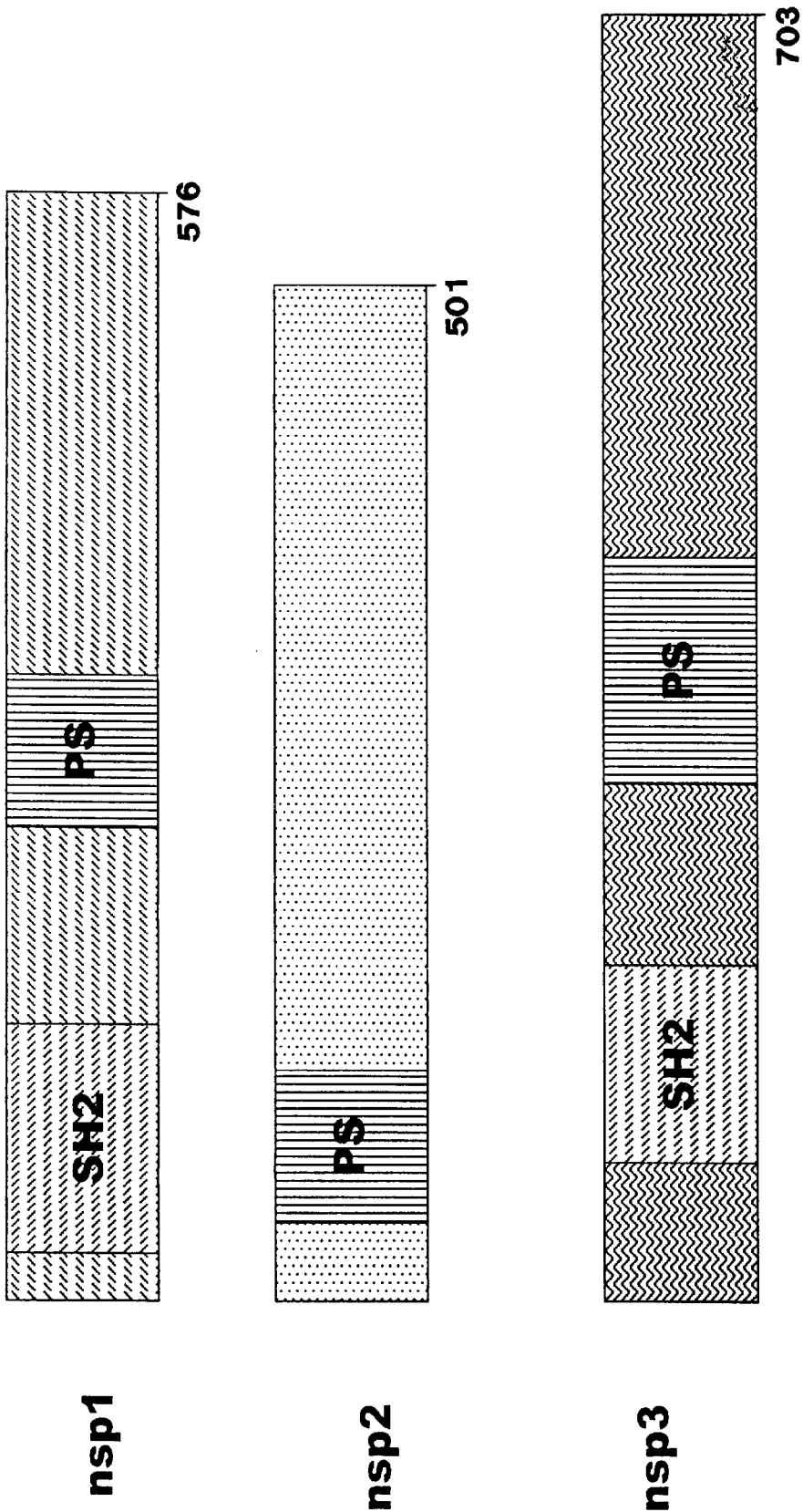
FIG. 6A shows a figurative illustrative comparison of the various domains between Nsp1 (SEQ ID NO:1), Nsp2 (SEQ ID NO:3) and Nsp3 (SEQ ID NO:5).

The terms "PRO201, PRO308 or PRO309," "PRO201, PRO308 or PRO309 polypeptide", when used herein encompass both native sequence PRO201, PRO308 or PRO309, respectively, and variants thereof (which are further defined herein). They may be isolated from a variety of sources, such as from human tissue types or from another source, or prepared by recombinant or synthetic methods.

Figure 1A:
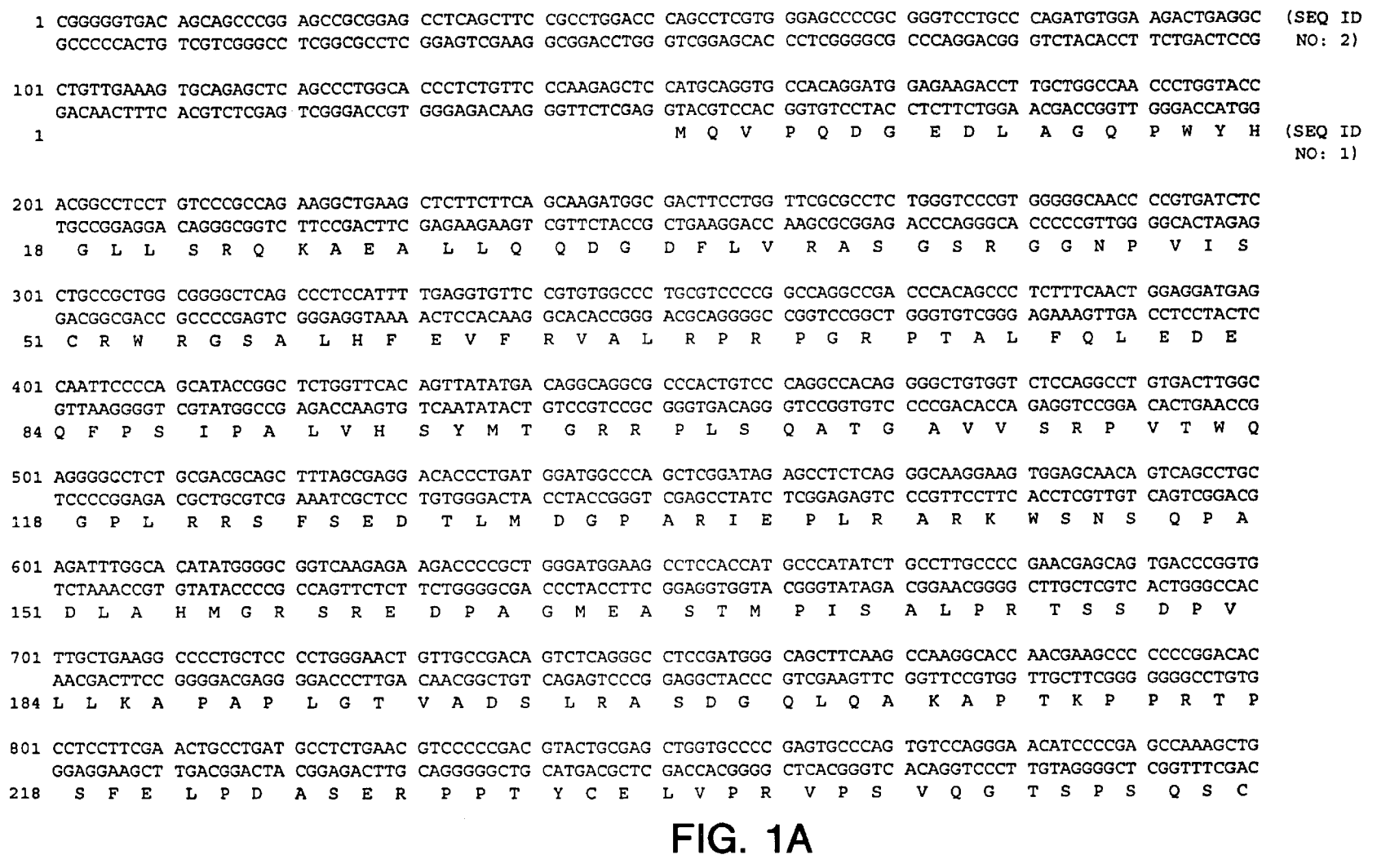

A "native sequence PRO201, PRO308 or PRO309" comprises a polypeptide having the same amino acid sequence as a PRO201, PRO308 or PRO309 derived from nature. Such native sequence PRO201, PRO308 or PRO309 can be isolated from nature or can be produced by recombinant or synthetic means. The term "native sequence PRO201, PRO308 or PRO309" specifically encompasses naturally-occurring truncated or secreted forms of PRO201, PRO308 or PRO309 (e.g., an extracellular domain sequence), naturally-occurring variant forms (e.g., alternatively spliced forms) and naturally-occurring allelic variants of PRO201, PRO308 or PRO309. Throughout this specification, the "PRO" and "Nsp" designations are both used to designate the respective proteins, wherein "Nsp" designates only the particular native human sequence of the sequence of FIGS. 1, 2, 3 and/or the sequence of the cDNA insert deposited under ATCC 209567, 209565 and 209713, respectively. Whereas "Nsp" designates the particularly enumerated species,"PRO" designates the native sequence (including the Nsps) and active variants thereof. In one embodiment of the invention, the native sequence PRO201, PRO308 or PRO309 is a mature or full-length native sequence PRO201, PRO308 or PRO309 comprising: (a) amino acids 1 to 576 of FIG. 1 (SEQ ID NO: 1); (b) amino acids 1 to 501 of FIG. 2 (SEQ ID NO: 3) and (c) amino acids 1 to 703 of FIG. 3 (SEQ ID NO: 5), respectively, with or without the N-terminal signal sequence, and with or without the initiating methionine at position 1.

"PRO201, PRO308 or PRO309 variant" means a biologically active PRO201, PRO308 or PRO309, respectively, as defined below having at least about 80% amino acid sequence identity to: (a) a DNA molecule encoding a PRO201, PRO308 or PRO309 polypeptide, with or without its native signal sequence, or (b) the complement of the DNA molecule of (a). In a particular embodiment, the PRO201, PRO308 or PRO309 variant has at least about 80% amino acid sequence homology with the PRO201, PRO308 or PRO309 having the deduced amino acid sequence shown in FIG. 1 (SEQ ID NO: 1, FIG. 2 (SEQ ID NO: 3) or FIG. 3 (SEQ ID NO: 5) for a full-length native sequence PRO201, PRO308 or PRO309. Such PRO201, PRO308 or PRO309 variants include, for instance, PRO201, PRO308 or PRO309 polypeptides wherein one or more amino acid residues are added, or deleted, at the N- or C-terminus of the sequence of FIG. 1 (SEQ ID NO:1), FIG. 2 (SEQ ID NO: 3) or FIG. 3 (SEQ ID NO: 5). Preferably, the nucleic acid or amino acid sequence identity is at least about 85%, more preferably at least about 90%, and even more preferably at least about 95%.

"Percent (%) amino acid sequence identity" with respect to the PRO201, PRO308 or PRO309 sequences identified herein is defined as the percentage of amino acid residues in a candidate sequence that are identical with the amino acid residues in the PRO201, PRO308 or PRO309 sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST-2 software set to the default parameters. Those skilled in the art can determine appropriate parameters for measuring alignment, including any algorithms needed to achieve maximal alignment over the full length of the sequences being compared. Alternatively, the percentage identity values used herein may be generated by the program "Align-2", which has no parameter settings, was authored by Genentech, Inc. and which was filed on Dec. 10, 1991 with user documentation in the United States Copyright Office, Washington, D.C. 20559. Align-2 is registered under U.S. copyright registration number TXU-510087.

"Percent (%) nucleic acid sequence identity" with respect to the PRO201, PRO308 and PRO309 sequences identified herein is defined as the percentage of nucleotides in a candidate sequence that are identical with the nucleotides in the PRO201, PRO308 or PRO309 sequence, after aligning the sequences and introducing gaps, if necessary, to achieve the maximum percent sequemce identity. Alignment for purposes of determining percent nucleic acid sequence identity can be acnieved in various ways that are within the skill in the art, for instance, using publicly available computer sokftware such as BLAST-2 software set the default parameters. Those skidded in the art can determine appropriate parameters for measuring alignment, including any algorithms needed to achieve maximal alignment over the full length of the sequences being compared. Alternatively, the percentage identity values used herein may be generated by the program "Align-2", which has no parameter settings, was authored by Genetech, Inc. and which was filed on Dec. 10, 1991 with user documentation in the United States Copyright Office, Washington, D.C. 20559. Align-2 is registered under U.S. copyright number TXU-510087.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the PRO201, PRO308 or PRO309 natural environment will not be present. Ordinarily, however, isolated polypeptide will be prepared by at least one purification step.

An "isolated" DNA30676 (SEQ ID NO:2), DNA40575 (SEQ ID NO:4) or DNA61601 (SEQ ID NO:6) nucleic acid molecule is a nucleic acid molecule that is identified and separated from at least one contaminant nucleic acid molecule with which it is ordinarily associated in the natural source of the DNA30676, DNA40575 or DNA61601 nucleic acid (SEQ ID NO:s 2, 4 & 6, respectively). An isolated DNA30676, DNA40575 or DNA61601 nucleic acid molecule (SEQ ID NO:s 2, 4 & 6, respectively) is other than in the form or setting in which it is found in nature. Isolated DNA30676, DNA40575 or DNA61601 nucleic acid molecules (SEQ ID NO:s 2, 4 & 6, respectively) therefore are distinguished from the DNA30676, DNA40575 or DNA61601 nucleic acid molecule (SEQ ID NO:s 2, 4 & 6, respectively) as it exists in natural cells. However, an isolated DNA30676, DNA40575 or DNA61601 nucleic acid molecule (SEQ ID NO:s 2, 4 & 6, respectively) includes DNA30676, DNA40575 or DNA61601 nucleic acid molecules (SEQ ID NO:s 2, 4 & 6, respectively) contained in cells that ordinarily express DNA30676, DNA40575 or DNA61601 (SEQ ID NO:s 2, 4 & 6, respectively) where, for example, the nucleic acid molecule is in a chromosomal location different from that of natural cells.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley lnterscience Publishers, (1995).

"Stringent conditions" or"high stringency conditions", as defined herein, may be identified by those that: (1) employ low ionic strength and high temperature for washing, for example 0.0 15 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising,: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37–50° C. The skilled artisan will recognize how to adjust the temperature, ionic strength, etc. as necessary to accommodate factors such as probe length and the like. The term "epitope tagged" when used herein refers to a chimeric polypeptide comprising a DNA30676, DNA40575 or DNA61601 potypeptide (SEQ ID NO:1, 3 & 5, respectively) fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers single anti-PRO201, anti-PRO308 or anti-PRO309 monoclonal antibodies (including agonist, antagonist, and neutralizing antibodies) and anti-PRO201, anti-PRO308 or anti-PRO309 antibody compositions with polyepitopic specificity. The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Active" or "activity" in the context of molecules identified based upon the PRO201, PRO308 or PRO309 polypeptides (or their coding sequences) refers to polypeptides (e.g., antibodies) or organic or inorganic small molecules, peptides, etc. which retain a biological and/or immunological activity of native or naturally-occurring PRO201, PRO308 or PRO309. A "biological" activity refers to a biological function (either inhibitory or stimulatory), caused by a native or naturally-occurring, PRO201, PRO308 or PRO309, other than the ability to induce the production of an antibody against an antigenic epitope possessed by a native or naturally-occurring PRO201, PRO308 or PRO309. An "immunological" activity refers to the ability to induce the production of an antibody against an antigenic epitope possessed by a native or naturally occurring PRO201, PRO308 or PRO309.

A preferred biological activity includes, for example, a biological activity identified by the screening assays identified herein, for example, growth inhibition of a target tumor cell. Another preferred biological activity is cytotoxic activity resulting in the death of the target tumor cell. Additional preferred activities involve the regulation or tumorigenesis and response to stimulation by, for example, integrin receptors ligands and by epidermal growth factor (EGF), insulin growth factor (IGF) and through other receptor tyrosine (RTK) ligands. More preferably, biological activity can be determined by measurement of guanylate exchange, in particular, the activation of c-jun kinase (JNK).

The term "modulate" means to affect (e.g., either upregulate, downregulate or otherwise control) the level of a signaling pathway. Cellular processes under the control of signal transduction include, but are not limited to, transcription of specific genes, normal cellular functions, such as metabolism, proliferation, differentiation, adhesion, apoptosis and survival, as well as abnormal processes, such as transformation, blocking of differentiation and metastasis.

The term "antagonist" is used herein in the broadest sense to include any molecule which blocks, prevents, inhibits, or neutralizes the process by which the PRO201, PRO308 or PRO309 molecules of the invention that interferes with the interaction of any of the protein domains of PRO201, PRO308 or PRO309 with various target proteins. Such interactions can generally occur with the C-terminal end of PRO201, PRO308 or PRO309, or specifically the SH2 and/or proline/serine (P/S) rich regions with phosphotyrosyl residues and polyproline motifs with a target binding site. In a similar manner, the term "agonist" is used herein to include any molecule which promotes, enhances or stimulates the interaction of the protein domains of PRO201, PRO308 or PRO309 (e.g., Nsp1, Nsp2 and Nsp3, respectively) including the SH2 and/or proline/serine (P/S) rich regions with phosphotyrosyl residues and polyproline motifs, respectively on various target proteins. Suitable molecules that affect the interaction of the SH2 and/or P/S regions of PRO201, PRO308 or PRO309 and the phosphotyrosyl residues and polyproline motifs, respectively or target proteins include fragments of the latter or small bioorganic molecules, e.g., peptidomimetics, which will prevent or enhance, as the case may be, the interaction. Non-limiting examples include proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like. Another preferred form of antagonist includes antisense nucleotides that inhibit the PRO201, PRO308 or PRO309 modulated signaling. Preferred forms bind to specific regions on either PRO201, PRO308 or PRO309 or the targets with which PRO201, PRO308 or PRO309 interact.

A "small molecule" is defined herein to have a molecular weight below about 500 Dattons. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas. The term "antibody" is used in the broadest sense and specifically covers, without limitation, intact monoclonal antibodies, polyclonal antibodies, multispecific antibodies (e.g. bispecific antibodies) formed from at least two intact antibodies, and antibody fragments so long as they exhibit the desired biological activity.

The phrases "gene amplification" and "gene duplication" are used interchangeably and refer to a process by which multiple copies of a gene or gene fragment are formed in a particular cell or cell line. The duplicated region (a stretch of amplified DNA) is often referred to as "amplicon." Usually, the amount of the messenger RNA (MRNA) produced, i.e. the level of gene expression, also increases in the proportion of the number of copies made of the particular gene expressed.

"Tumor", as used herein, refers to all neoplastic cell proliferation, whether malignant or benign, and all precancerous and cancerous cells and tissues.

The terms "cancer" and "cancerous" refer to or describe the physiological condition in mammals that is typically characterized by unregulated cell growth. Examples of cancer include but are not limited to, carcinoms, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, colorectal cancer, endometrial carcinoma, salivary gland carcinama, kidney cancer, liver cancer, vulva cancer, thyroid cancer, hepatic carcinoma and various types of head and neck cancer.

"Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. In tumor (e.g. cancer) treatment, a therapeutic agent may directly decrease the pathology of tumor cells, or render the tumor cells more susceptible to treatment by other therapeutic agents, e.g. radiation and/or chemotherapy.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products as abnormal levels, suppression or aggravation of inflammatory or immunological response, etc.

"Mammal" for purposes of treatment refers to any animal classified as a mammal, including humans, domestic and farm animals, and zoo, sports, or pet animals, such as dogs, horses, cats, hamsters, rats, mice, cattle pigs, goats, sheep, etc. Preferably, the mammal is human.

"Carriers" as used herein include pharmaceutically acceptable carriers, excipients, or stabilizers which are non-toxic to the cell or mammal being exposed thereto at the dosages and concentrations empolyed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyuethylene glycol (PEG), and PLURONICS™.

Administration "in combination with" or "admixture with" one or more further therapeutic agents includes simultaneous (concurrent) and consecutive administration in any order.

The term "cytotoxic agent" as used herein refers to a substance that inhibits or prevents the function of cells and/or causes destruction of cells. The term is intended to include radioactive isotopes (e.g. $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents includeadriamycin, doxorubicin, epirubicin, 5-fluorouracil, bytosine arabinoside ("Ara-C"), cyclophosphamide, thiotepa, busulfan, cytoxin, taxoids, e.g. paclitaxel (Taxol™, Bristol-Myers Squibb Oncology, Princeton, N.J. and doxetaxel (Taxotere™, Rhône-Poulenc Rorer, Antony, France), toxotere, methotrexate, cisplatin, melphalan, vinblastine, bleomycin, etoposide, ifosfamide, mitomycin C, mitoxantrone, vincristine, vinorelbine, carboplatin, teniposide, daunomycin, carminomycin, aminopterin, dactinomycin, mitomycins, esperamicins (see U.S. Pat. No. 4,675,187), 5-FU, 6-thioguanine, 6-mercaptopurine, actinomycin D, VP-16, chlorambucil, melphalan, and other related nitrogen mustards. Also included in this definition are hormonal agents that act to regulate or inhibit hormone actin on tumors such as tamoxifen and onapristone.

A "growth inhibitory agent" when used herein refers to a compound or composition which inhibits growth of a cell, especially cancer cell overexpressing any of the genes identified herein, either in vitro or in vivo. Thus, the growth inhibitory agent is one which significantly reduces the percentage of cells overexpressing such genes in S phase. Examples of growth inhibitory agents include agents that block cell cytcle progression (at a place other than S phase), such as agents that induce G1 arrest and M-phase arrest. Classical M-phase blockers include the vincas (vincristine and vinblastine), taxol, and topo II inhibitors such as doxoroubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogens, and antineoplastic drugs" by Murakami et al. (WB Saunders: Philadelphia, 1995), especially p. 13.

"Doxorubicin" is an athracycline antibiotic. The full chemical name of doxorubicin is (8S-cis)-10-[(3-amino-2,3,6trideoxy-α-L-lyxo-hexapyranosyl)oxy]-7,8,9,10-tetrahydro-6,8,11trihydroxy-8-(hydroxyacetyl)-1-methoxy-5,12-naphthacenedione.

The term "cytokine" is a generic term for proteins released by one cell populatin which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; porrelaxin; glycoprotein hormones such as follicle stijulatin hormone (FSH), thyroid stimulatin hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-;ike growth factor-I and -II; erthropoietin (EPO); osteoinductive factors; interferons such as interferon -α, -β, and -γ; colony stimulating factors (CSFs) such as macrophage-CSF (M-CSF); granulocytemacrophage-CSF (GM-CSF); and granulocyte-CSF (G-CSF); interleukins (ILs) such as IL-1, IL- 1α, IL-2, IL-3, IL-4, IL- 5, IL-6, IL-7, IL-8, IL-9, IL-10, IL-11, IL-12; a tumor necrosis factor such as TGF-α and TGF-β; and other polypeptide factors including LIF and kit ligand (KL). As used herein, the term cytokine includes proteins from natural sources or from recombinant cell culture and biologically active equivalents of the native sequence cytokines.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g. Wilman, "Prodrugs in Cancer Chemotherapy", Biochemical Society Transactions, 14, pp. 375–382, 615th Meeting, Belfast (1986), and Stella et al., "Prodrugs: A Chemical Approach to Targeted Drug Delivery", Directed Drug delivery, Borchardt et al., (ed), pp. 147–267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glysocylated prodrugs, β-lactam-containing prodrugs, optionally substituted phenoxyacetamide-containing prodrugs or optionally substituted phenylacetamide-containing prodrus, 5-fluorocytosine and other 5-fluorouridine prodrugs which can be converted into the more active cytotoxic free drug. Examples of cytotoxic drugs that can be derivatized into a prodrugs form for use in this invention include, but are not limited to, those chemotherapeutic agents described above.

"Native antibodies" and "native immunoglobulins" are usually heterotetraeric glycoproteins of about 150,000 Dalton, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three or four segments called "complementarity-determining regions" (CDRS) or "hypervariable regions" in both in the light-chain and the heavy-chain variable domains. The more highly conserved portions of variable domains are called the framework (FR). The variable domains of native heavy and light chains each comprise four or five FR regions, largely adopting a β-sheet configuration, connected by the CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., NIH Pubt. No.91–3242, Vol. 1, pages 647–669 (1991)). The constant domains are not necessarily involved directly in binding an antibody to an antigen, but exhibit various effector functions, such as participation of the antibody in antibody-dependent cellular toxicity.

The term "hypervariable region" or "complementarity-determining regions" (CDRS) as used herein define a sub-region within the variable region of extreme sequence variability of the antibody, which forma the antigen-binding site and are the main determinants of antigen specificity. According to one definition, they can be residues (Kabat nomenclature) 24–34 (L1), 50–56 (L2) and 89–97 (L3) in the light chain variable region and resides (Kabat nomenclature 31–35 (H1), 50–65 (H2), 95–102 (H3) in the heavy chain variable region. Kabat et al. *Sequences of Proteins of Immunological Interest*, 5th Ed. Public Health Service, National Institute of Health, Bethesda, Md. [1991]). Alternatively, or in combination with the region defined by Kabat, the hypervariable region can be the "hypervariable loop", comprising residues (Chothia nomenclature) 26–32 (L1), 50–53 (L2), 91–96 (L3) in the light chain variable region and residue (Chothia nomenclature) 26–32 (H1), 53–55 (L2) and 96–101 (L3); Chothia and Lesk, *J. Mol. Biol.* 196: 901–917 [1987]). "Framework" or "FR" residues are those variable domain residues of relatively low sequence variability which lie in between the CDR regions.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al. , *Protein Eng.* 8 (10) :1057–1062 [1995]); single-chain antibody molecules; and multispecific antibodies formed from antibody fragments.

Papai digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$–$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobutins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further-divided into subclasses (isotypes), e.g., IgG1, IgG2, IgG3, IgG4, IgA, and IgA2. The heavy-chain constant domains that correspond to the different classes of immunoglobulins are called α, δ, ε, γ, and μ, respectively. The subunit structures and thnree-dimensional configurations of different classes of immunoglobulins are well known.

The term "monoclonal antibody" as used herein refers to an antibody obtained from a population of substantially homogeneous antibodies, i e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256:495 [1975], or may be made by recombinant DNA methods (see, e.g., U.S. Pat. No. 4,816,567). The "monoclonal antibodies" may also be isolated from phange antibody libraries using the techniques described in Clackson et al., Nature, 352: 624–628 [1991] and Marks et al., J. Mol. Biol., 222:581–597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81:6851–6855 [1984]).

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part humanized antibodies are human immunoglobulins (recipient antibody) in which residues from a CDR of the recipient are replaced by residues from a CDR of a non-human species (donor antibody) such as mouse, rat or rabbit having the desired specificity, affinity, and capacity. In some instances, Fv FR residues of the human immunoglobulin are replaced by corresponding non-human residues. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321:522–525 (1986); Reichmann et al., Nature, 332: 323–329 [1998]; and Presta, Curr. Op. Struct. Biol., 2:593–596 (1992). The humanized antibody includes a PRIMATIZED® antibody wherein the antigen-binding region of the antibody is derived from an antibody produced by immunizing macaque monkeys with the antigen of interest.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv see Pluckthun in The Pharmacology of Monoclonal Antibodies, vol. 113, Rosenburg and Moore eds., Springer-Veriag, New York, pp. 269–315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$–$V_L$). BY using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90: 6444–6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable. Radionuclides that can serve as detectable labels include, for example, I-131, I-123, I-125, Y-90, Re-188, Re-186, At-211, Cu-67, Bi-212, and Pd-109.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

II. Compositions and Methods of the Invention

A. Full-length PRO201, PRO308 or PRO309

The present invention provides newly identified and isolated nucleotide sequences encoding polypeptides referred to in the present application as PRO201 (e.g., Nsp1, SEQ ID NO:1), PRO308 (e.g., Nsp2, SEQ ID NO:3) or PRO309 (e.g., Nsp3, SEQ ID NO:5). In particular, Applicants have identified and isolated cDNA encoding a PRO201, PRO308 and PRO309 polypeptide, as disclosed in further detail in the Examples below. Using the BLAST-2 sequence alignment computer program set to the default parameters, Applicants found that a full-length native sequence Nsp1 and Nsp3 (shown in FIGS. 6A & 6B and SEQ ID NO:1 & 3, respectively) have regions of SH2 homology, while Nsp1, Nsp2 and Nsp3 (SEQ ID NO:1, 3 & 5) have a proline/serine rich (P/S) region homology. SH2 domains are known to bind specific phosphotyrosyl residues, while the P/S region could be a potential SH3 interaction domain. Accordingly, it is presently believed that PRO201, PRO308 and PRO309 disclosed in the present application are newly identified family of adaptor proteins and may possess properties which modulate intracellular signaling pathways.

B. PRO201, PRO308 or PRO309 Variants

In addition to the full-length native sequence PRO201, PRO308 and PRO309 described herein, it is contemplated that PRO201, PRO308 and PRO309 variants can be prepared. PRO201, PRO308 and PRO309 variants can be prepared by introducing appropriate nucleotide changes into the PRO201, PRO308 or PRO309 DNA, or by synthesis of the desired PRO201, PRO308 or PRO309 polypeptides. Those skilled in the art will appreciate that amino acid changes may alter post-translational processes of the PRO201, PRO308 or PRO309, such as changing the number or position of giycosylation sites or altering the membrane anchoring characteristics.

Variations in the native full-length sequence PRO201, PRO308 or PRO309 or in various domains of the PRO201, PRO308 or PRO309 described herein, can be made, for example, using any of the techniques and guidelines for conservative and non-conservative mutations set forth, for instance, in U.S. Pat. No. 5,364,934. Variations may be a substitution, deletion or insertion of one or more codons encoding the PRO201, PRO308 or PRO309 that results in a change in the amino acid sequence of the PRO201, PRO308 or PRO309 as compared with the native sequence PRO201, PRO308 or PRO309. Optionally the variation is by substitution of at least one amino acid with any other amino acid in one or more of the domains of the PRO201, PRO308 or PRO309. Guidance in determining which amino acid residue may be inserted, substituted or deleted without adversely affecting the desired activity may be found by comparing the sequence of the PRO201, PRO308 or PRO309 with that of homologous known protein molecules and minimizing the number of amino acid sequence changes made in regions of high homology. Amino acid substitutions can be the result of replacing one amino acid with another amino acid having similar structural and/or chemical properties, such as the replacement of a feucine with a serine, i.e., conservative amino acid replacements. Insertions or deletions may optionally be in the range of 1to 5 amino acids. The variation allowed may be determined by systematically making insertions, deletions or substitutions of amino acids in the sequence and testing the resulting variants for activity in the in vitro assay described in the Examples below.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Phi-los. Trans. R. Soc. London Ser A*, 317:415 (1986)] or other known techniques can be performed on the cloned DNA to produce the PRO201, PRO309 or PRO309 variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions [Creighton, *The Proteins*, (W. H. Freeman & Co., N.Y.); Chothia, *J. Mol. Biol.*, 150:1 (1976)]. If alanine substitution does not yield adequate amounts of variant, an isoteric amino acid can be used.

C. Modifications of PRO201, PRO308 or PRO309

Covalent modifications of PRO201, PRO308 or PRO309 are included within the scope of this invention. One type of covalent modification includes reacting targeted amino acid residues of the PRO201, PRO308 or PRO309 with an organic derivatizing agent that is capable of reacting with selected side chains or the N- or C-terminal residues of the PRO201, PRO308 or PRO309. Derivatization with bifunctional agents is useful, for instance, for crosslinking PRO201, PRO308 or PRO309 to a water-insoluble support matrix or surface for use in the method for purifying anti-PRO201, PRO308 or PRO309 antibodies, and vice-versa. Commonly used crosslinking agents include, e.g., 1,1-bis(diazoacetyl)-2-phenylethane, glutaraidehyde, N-hydroxysuccinimide esters, for example, esters with 4-azidosalicylic acid, homobifunctional imidoesters, including disuccinimidyl esters such as 3,3'-dithiobis (succinimidylpropionate), bifunctional maleimides such as bis-N-maleimido-1,8-octane and agents such as methyl-3-[(p-azidophenyl)dithiol]propioimidate.

Other modifications include deamidation of giutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W. H. Freeman & Co., San Francisco, pp. 79–86 (1983)], acetylation of the N-terminal amine, and amidation of any C-terminal carboxyl group.

Another type of covalent modification of the PRO201, PRO308 or PRO309 polypeptide included within the scope of this invention comprises altering the native glycosylation pattern of the polypeptide. "Altering the native glycosylation pattern" is intended for purposes herein to mean deleting one or more carbohydrate moieties found in native sequence PRO201, PRO308 or PRO309, and/or adding one or more glycosylation sites that are not present in the native sequence PRO201, PRO308 or PRO309, and/or alteration of the ratio and/or composition of the sugar residues attached to the glycosylation site(s).

Addition of glycosylation sites to the PRO201, PRO308 or PRO309 potypeptide may be accomplished by altering the amino acid sequence. The alteration may be made, for example, by the addition of, or substitution by, one or more serine or threonine residues to the native sequence PRO201, PRO308 or PRO309 (for O-linked glycosylation sites). The PRO201, PRO308 or PRO309 amino acid sequence may optionally be altered through changes at the DNA level, particularly by mutating the DNA encoding die PRO201, PRO308 or PRO309 polypeptide at preselected bases such that codons are generated that will translate into the desired amino acids.

Another means of increasing the number of carbohydrate moieties on the PRO201, PRO308 or PRO309 polypeptide is by chemical or enzymatic coupling of glycosides to the polypeptide. Such methods are described in the art, e.g., in WO 87105330 published Sep. 11, 1987, and in Aplin and Wriston, *CRC Crit. Rev. Biochem.*, pp. 259–306 (1981).

Removal of carbohydrate moieties present on the PRO201, PRO308 or PRO309 polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of PRO201, PRO308 or PRO309 comprises linking the PRO201, PRO308 or PRO309 polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

The PRO201, PRO308 or PRO309 of the present invention may also be modified in a way to form a chimeric molecule comprising PRO201, PRO308 or PRO309 fused to another, heterologous polypeptide or amino acid sequence. In one embodiment, such a chimeric molecule comprises a fusion of the PRO201, PRO308 or PRO309 with a tag polypeptide which provides an epitope to which an anti-tag antibody can selectively bind. The epitope tag is generally placed at the amino- or carboxyl- terminus of the PRO201, PRO308 or PRO309. The presence of such epitope-tagged forms of the PRO201, PRO308 or PRO309 can be detected using an antibody against the tag polypeptide. Also, provision of the epitope tag enables the PRO201, PRO308 or PRO309 to be readily purified by affinity purification using an anti-tag antibody or another type of affinity matrix that binds to the epitope tag. In an alternative embodiment, the chimeric molecule may comprise a fusion of the PRO201, PRO308 or PRO309 with an immunoglobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol*, 8:2159–2165 (1998)]; the c-myc tag and the 8F9, 3C7, 6E10, G4, B7 and 9E10 antibodies thereto [Evan et al., *Molecular and Cellular Biology*, 5:3610–3616 (1985)]; and the Herpes Simplex virus glycoprotein D (gD)) tag and its antibody [Paborsky et al., *Protein Engineering*, 3(6):547–553 (1990)]. Other tag polypeptides include the Flag-peptide [Hopp et al., *Bio Technology*, 6:1204–1210 (1988)]; the KT3 epitope peptide [Martin et al., *Science*, 255:192–194 (1992)]; an α-tubulin epitope peptide [Skinner et al., *J. Biol. Chem.*, 266:15163–15166 (1991)]; and the T7 gene 10 protein peptide tag [Lutz-Freyermuth et al., *Proc. Natl. Acad. Sci. USA*, 87:6393–6397 (1990)].

D. Preparation of PRO201, PRO308 or PRO309

The description below relates primarily to production of PRO201, PRO308 OR PRO309 by culturing cells transformed or transfected with a vector containing PRO201, PRO308 OR PRO309 nucleic acid. It is, of course, contemplated that alternative methods, which are well known in the art, may be employed to prepare PRO201, PRO308 or PRO309. For instance, the PRO201, PRO308 or PRO309 sequence, or portions thereof, may be produced by direct peptide synthesis using solid-phase techniques [see, e.g., Stewart et al., *Solid-Phase Peptize Synthesis*, W. H. Freeman Co., San Francisco, Calif. (1969); Merrifield, *J. Am. Chem. Soc.*, 85:2149–2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the PRO201, PRO308 or PRO309 may be chemically synthesized separately and combined using chemical or enzymatic methods to produce the full-length PRO201, PRO308 or PRO309.

1. Isolation of DNA Encoding PRO201, PRO308 or PRO309

DNA encoding PRO201, PRO308 or PRO309 may be obtained from a cDNA library prepared from tissue believed to possess the PRO201, PRO308 or PRO309 mRNA and to express it at a detectable level. Accordingly, human PRO201, PRO308 or PRO309 DNA can be conveniently obtained from a cDNA library prepared from human tissue, such as described in the Examples. The PRO201, PRO308 or PRO309-encoding gene may also be obtained from a genomic library or by oligonucleotide synthesis.

Libraries can be screened with probes (such as antibodies to the PRO201, PRO308 or PRO309 or oligonucleotides of at least about 20–80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding PRO201, PRO308 or PRO309 is to use PCR methodology [Sambrook et al., supra; Dieffenbach et al., *PCR Primer: A Laboratory Manual* (Cold Spring Harbor Laboratory Press, 1995)].

Exemplary techniques for screening a cDNA library are described below in the Examples. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucieutide level) within defined regions of the molecule or across the full-length sequence can be determined through sequence alignment using computer software programs such as BLAST, BLAST-2, ALIGN, DNAstar, and INHERIT which employ various algorithms to measure homology.

Nucleic acid having protein coding sequence may be obtained by screening selected cDNA or genomic libraries using the deduced amino acid sequence disclosed herein for the first time, and, if necessary, using conventional primer extension procedures as described in Saznbrook et al., supra, to detect precursors and processing intermediates of mRNA that may not have been reverse-transcribed into cDNA.

2. Selection and Transformation of Host Cells

Host cells are transfected or transformed with expression or cloning vectors described herein for PRO201, PRO308 or PRO309 production and cultured in conventional nutrient media modified as appropriate for inducing promoters, selecting ftwasformants, or amplifying the genes encoding the desired sequences. The culture conditions, such as media, temperature, pH and the like, can be selected by the skilled artisan without undue experimentation. in general, principles, protocols, and practical techniques for maximizing the productivity of cell cultures can be found in *Mammalian Cell Biotechnology: A Practical Approach*, M. Butler, ed. (IRL Press, 1991) and Sambrook et al., suapra.

Methods of transfection are known to the ordinarily skilled artisan, for example, $CaPO_4$ and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published Jun. 29, 1989. For mammalian cells without such cell walls, the calcium phosphate precipitation method of Graham and van der Eb, *Virology*, 52:456–457 (1978) can be employed. General aspects of mammalian cell host system transformations have been described in U.S. Pat. No. 4,399,216. Transformations into yeast are typically carried out according to the method of Van Solingen et al., *J. Bact*, 130:946 (1977) and Hsiao et al., *Proc. Natl. Acad. Sci.* (USA), 76:3829 (1979). However, other methods for introducing DNA into cells, such as by nuclear microinjection, electroporation, bacterial protoplast fusion with intact cells, or polycations, e.g., polybrene, polyomithine, may also be used. For various techniques for transforming mammalian cells, see Keown et al., *Methods in Enzymology*, 185:527–537 (1990) and Mansour et al., *Nature*, 336:348–352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and KS 772 (ATCC 53,635).

In addition to prokaryotes, eukaryotic microbes such as filamentous fungi or yeast are suitable cloning or expression hosts for PRO201, PRO308 OR PRO309-encoding vectors. *Saccharomyces cerevisiae* is a commonly used lower eukaryotic host microorganism.

Suitable host cells for the expression of glycosylated PRO201, PRO308 or PRO309 are derived from multicellular organisms. Examples of invertebrate cells include insect cells such as Drosophila S2 and Spodoptera Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcioned for growth in suspension culture, Graham et al., *J. Gen Virol.*, 36:59 (1977)); Chinese hamster ovary cells/-DHFR (CHO, Urlaub and Chasin, *Proc. Natl. Acad. Sci. USA*, 77:4216 (1980)); mouse sertoli cells (TM4, Mather, *Biol. Reprod*, 23:243–251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Reipiicable Vector

The nucleic acid (e.g., cDNA or genomic DNA) encoding PRO201, PRO308 or PRO0309 may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The PRO201, PRO308 or PRO309 may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the PRO201, PRO308 or PRO309 DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including Saccharomyces and Kluyveromyces α-factor leaders, the latter described in U.S. Pat. No. 5,010,182), or acid phosphatase leader, the *C. albicans* glucoamylase leader (EP 362,179 published Apr. 4, 1990), or the signal described in WO 90/13646 published Nov. 15, 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the $2\,\mu$ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable markner. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the PRO201, PRO308 or PRO309 nucleic acid, such as DHFR or thymidine kinase. An appropriate host cell when wild-type DHFR is employed is the CHO cell line deficient in DHFR activity, prepared and propagated as described by Urfaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the PRO201, PRO308 or PRO309 nucleic acid sequence to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., *Proc. Natl. Acad. Sci. USA*, 80:21–25 (1983)]. Promoters for use in bacterial systems also will contain a Shine-Daigamo (S.D.) sequence operably linked to the DNA encoding PRO201, PRO308 or PRO309.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol debydrogenase 2, isocytochrome C, acid phosphatase, degradative enzymes associated with nitrogen metabolism, metaliothionein, glyceraidehyde-3-phosphate dehydrogenase, and enzymes responsible for maitose and galactose utilization. Suitable vectors and promoters for use in yeast expression are further described in EP 73,657.

PRO201, PRO308 or PRO309 transcription from vectors in mammalian host cells is controlled, for example, by promoters obtained from the genomes of viruses such as polyoma virus, fowipox virus (UK 2,211,504 published Jul. 5, 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the PRO201, PRO308 or PRO309 by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, a-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at a position 5' or 3' to the PRO201, PRO308 or PRO0309 coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucteotide segments transcribed as polyadenylated fragments in the untranslated portion of the mRNA encoding PRO201, PRO308 or PRO309.

Still other methods, vectors, and host cells suitable for adaptation to the synthesis of PRO201, PRO308 or PRO309 in recombinant vertebrate cell culture are described in Gething et al., *Nature*, 293:620–625 (1981); Mantei et al., *Nature*, 281:40–46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201–5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or poiyclonal, and may be prepared in any mammal. Conveniently, the antibodies may be prepared against a native sequence PRO201, PRO308 or PRO309 polypeptide or against a synthetic peptide based on the DNA sequences provided herein or against exogenous sequence fused to PRO201, PRO308 or PRO309 DNA and encoding a specific antibody epitope.

5. Purification of Polypeptide

Forms of PRO201, PRO308 or PRO309 may be recovered from culture medium or from host cell lysates. If membrane-bound, it can be released from the membrane using a suitable detergent solution (e.g. Triton-X 100) or by enzymatic cleavage. Cells employed in expression of PRO201, PRO308 or PRO309 can be disrupted by various physical or chemical means, such as freeze-thaw cycling, sonication, mechanical disruption, or cell lysing agents.

It may be desired to purify PRO201, PRO308 or PRO309 from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the PRO201, PRO308 or PRO309. Various methods of protein purification may be employed and such methods are known in the art and described for example in Deutscher, *Methods in Enzymology*, 182 (1990) Scopes, *Protein Purification: Principles and Practice*, Springer- Veriag, New York (1982). The purification step(s) selected will depend, for example, on the nature of the production process used and the particular PRO201, PRO308 or PRO309 produced.

E. Uses for PRO201, PRO308 OR PRO309

Nucleotide sequences (or their complement) encoding PRO201, PRO308 or PRO309 have various applications in the art of molecular biology, including uses as hybridization probes, in chromosome and gene mapping and in the generation of anti-sense RNA and DNA. PRO201, PRO308 or PRO309 nucleic acid will also be useful for the preparation of PRO201, PRO308 or PRO309 potypeptides by the recombinant techniques described herein.

Figure 2A:
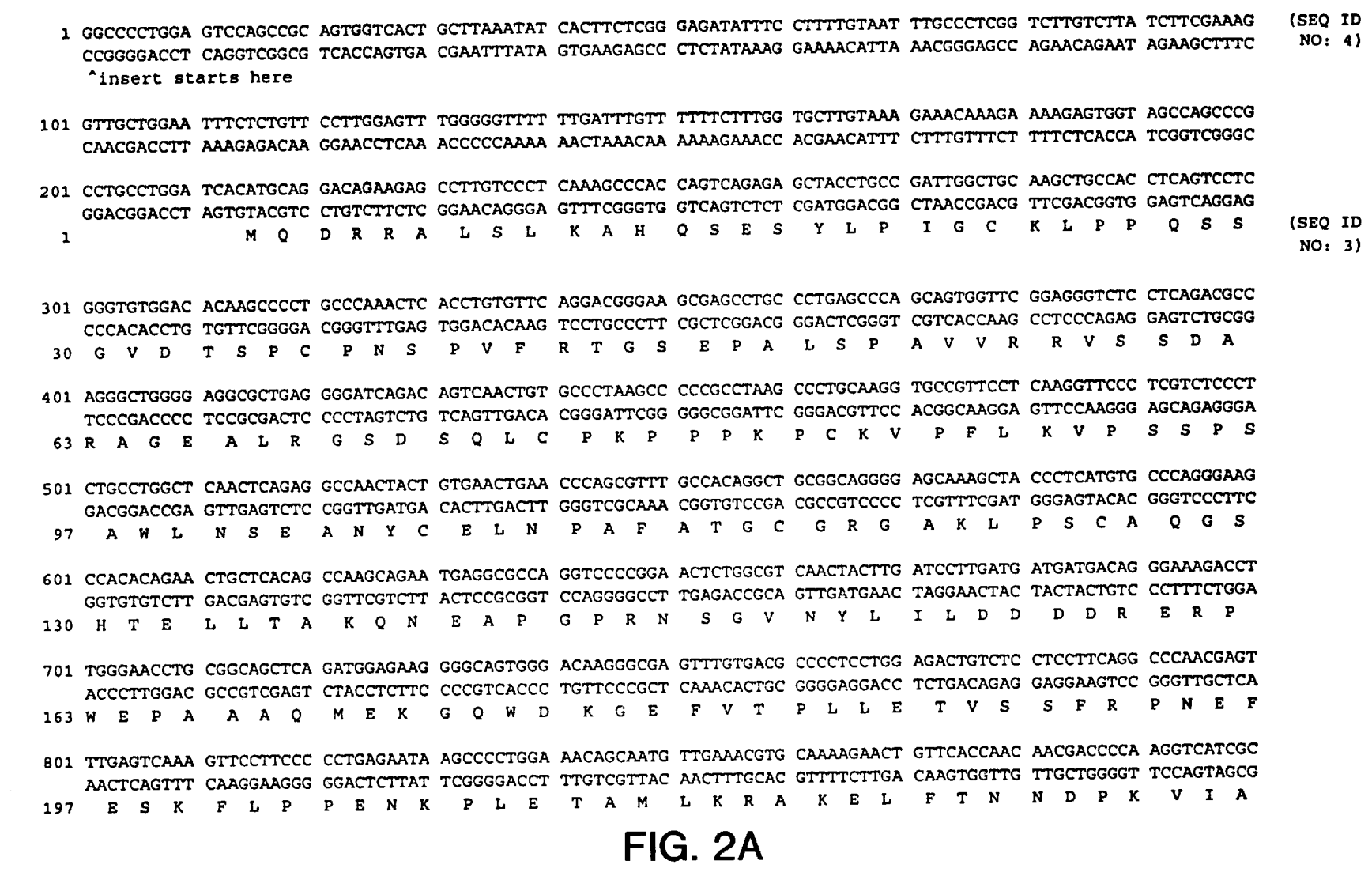

The full-length native sequence PRO201, PRO308 or PRO309 (SEQ ID NO:1, 3 & 5) gene, or portions thereof, may be used as hybridization probes for a cDNA library to isolate the full-length gene or to isolate still other genes (for instance, those encoding naturally-occurring variants of PRO201, PRO308 or PRO309 or PRO201, PRO308 or PRO309 from other species) which have a desired sequence identity to the PRO201, PRO308 or PRO309 sequence disclosed in FIGS. 1–3 (SEQ ID NO: 1, 3 & 5). Optionally, the length of the probes will be about 20 to about 50 bases. The hybridization probes may be derived from the nucleotide sequence of SEQ ID NO: 1, 3 or 5 or from genomic sequences including promoters, enhancer elements and introns of native sequence PRO201, PRO308 or PRO309. By way of example, a screening method will comprise isolating the coding region of the PRO201, PRO308 or PRO309 gene using the known DNA sequence to synthesize a selected probe of about 40 bases. Hybridization probes may be labeled by a variety of labels, including radionucieotides such as $^{32}P$ or $^{35}S$, or enzymatic labels such as alkaline phosphatase coupled to the probe via avidin/biotin coupling systems. Labeled probes having a sequence complementary to that of the PRO201, PRO308 or PRO309 gene of the present invention can be used to screen libraries of human cDNA, genomic DNA or mRNA to determine which members of such libraries the probe hybridizes to. Hybridization techniques are described in farther detail in the Examples below.

The probes may also be employed in PCR techniques to generate a pool of sequences for identification of closely related PRO201, PRO308 or PRO309 sequences.

Nucleotide sequences encoding a PRO201, PRO308 or PRO309 can also be used to construct hybridization probes for mapping the gene which encodes that PRO201, PRO308 or PRO309 and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for PRO201, PRO308 or PRO309 encode a protein which binds to another protein (example, where the PRO201, PRO308 or PRO309 is a receptor), the PRO201, PRO308 or PRO309 can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor PRO201, PRO308 or PRO309 can be used to isolate correlative ligand(s). Screening assays can be designed to find lead compounds that mimic the biological activity of a native PRO201, PRO308 or PRO309 or a receptor for PRO201, PRO308 or PRO309. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

DNA30676 (SEQ ID NO:2) contains a single long open reading frame which can encode a 576 amino acid protein, herein termed Nsp1 (novel SH2 containing protein) (FIG. 1). Nsp1 (SEQ ID NO:1) is related to Sck and Shc (See FIG. 8, SEQ ID NO:s 16 & 17) as determined by the indicated N-terminal homology. Nsp1 (SEQ ID NO:1) also contains a proline-scrine rich domain (P/S) in the middle of the protein that may function as an SH3 interaction domain. The C terminus of the protein has no obviously relevant homology to any known mammalian proteins. Nsp1 (SEQ ID NO:1), Nsp2 (SEQ ID NO:3) and Nsp3 (SEQ ID NO:5) share an overall homology between 33 and 47%. Nsp3 (SEQ ID NO:5) has an SH2 domain and a potential SH3 interaction domain, while Nsp2 (SEQ ID NO:3) lacks the SH2 domain but does have a potential SH3 interaction domain. The absence of the SH2 domain in Nsp2 (SEQ ID NO:3) is suggestive that this protein could act as a dominant negative regulator of the other two Nsps. The lack of any apparent kinase or phosphatase domain suggests that they represent a novel family of adaptor proteins.

Adapter proteins are believed to play a significant role integrating multiple signaling cascades and in determining specific response to extraceilular stimuli. Signals generated by growth factors such as EGF or IGF-1 through receptor tyrosine kinases or by extracellular matrix components acting through the integrin receptors can induce cytoskeletal changes. Applicants have shown that the EGF receptor coimmunoprecipitates with Nsp1 and is phosphorylated in response to EGF signaling. Thus, antagonists of Nsp1 would be expected to be useful to inhibit cellular response attributed to stimulation by growth factors such as EGF or IGF-1 (e.g., tumorigenesis).

Several characteristics suggest that Nsp1 could play an important role in modulating the response to external stimuli. Nsp1 (SEQ ID NO:1) is phosphorylated in response to EGF stimulation and forms a complex that includes the EGF receptor, P13 kinase and Cas. The Nsp1/Cas complex also responds to signalig through the fibronectin receptor. However, the stoichiometry of the interaction and the phosphorylation status of the components differs between the two stimuli. The implication is that that biological outcome in response to these extracellular signals could be quite distinct in the presence or absence of Nsp1. For example, FAK associates with the SH3 region of Cas via a PXXP region at the C-terminus of FAK P(715)SRP—mouse nomenclature (Harte et al., *J. Biol. Chem.* 271: 13649–55 (1996). There are six PXXP signatures in Nsp1 (SEQ ID NO:1). This raises the possibility that Nsp1 could compete for the SH3 region on Cas and decrease the amount of Fak that is bound to Cas and so alter Fak dependent events. The data also point to an EGF mediated decrease in the extent of phosphorylation of the Cas that is associated with Nsp1 (SEQ ID NO:1). This complex then is likely to have a decrease in the number of proteins associated with the phosphorylated tyrosines of the Cas and so lead to changes in downstream events. As Nsp1 (SEQ ID NO:1) expression is highest in fetal bissues this protein could potentially have an important role in mediating the developmental readout of extracellular signals.

F. Amplification of Genes Encoding the PRO201, PRO308 or PRO309 Polypeptides in Tumor Tissues and Cell Lines The present invention is based in part on the identification and characterization of genes that are amplified in certain cancer cells.

The genome of prokaryotic and eukaryotic organisms is subjected to two seemingly conflicting requirements. One is the preservation and propagation of DNA as the genetic information in its original form, to guarantee stable inheritance through multiple generations. On the other hand, cells or organisms must be able to adapt to lasting environmental changes. The adaptive mechanisms can include qualitative or quantitative modifications of the genetic material. Qualitative modifications include DNA mutations, in which coding sequences are altered resulting in a structurally and/or functionally different protein. Gene amplification is a quantitative modification, whereby the actual number of complete coding sequence, ie. a gene, increases, leading to an increased number of available templates for transcription, an increased number of translatable transcripts, and, ultimately, to an increased abundance of the protein encoded by the amplified gene.

The phenomenon of gene amplification and its underlying mechanisms have been investigated in vitro in several prokwryotic and eukaryotic culture systems. The best-characterized example of gene amplification involves the culture of eukaryotic cells in medium containing variable concentrations of the cytotoxic drug methotrexate (MTX). MTX is a folic acid analogue and interferes with DNA synthesis by blocking the enzyme dihydrofoiate reductase (DHFR). During the initial exposure to low concentrations of MTX most cells (>99.9%) will die. A small number of cells survive, and are capable of growing in increasing concentrations of MTX by producing large amounts of DHFR-RNA and protein. The basis of this overproduction is the amplification of the single DHFR gene. The additional copies of the gene are found as extrachromosomal copies in the form of small, supernumerary chromosomes (double minutes) or as integrated chromosomal copies.

Gene amplification is most commonly encountered in the development of resistance to cytotoxic drugs (antibiotics for bacteria and chemotherapeutic agents for eukaryotic cells) and neoplastic transformation. Transformation of a eukaryotic cell as a spontaneous event or due to a viral or chemical/environmental insult is typically associated with changes in the genetic material of that cell. One of the most common genetic changes observed in human malignancies are mutations of the p53 protein. p53 controls the transition of cells from the stationary (G1) to the replicative (S) phase and prevents this transition in the presence of DNA damage. In other words, one of the main consequences of disabling p53 mutations is the accumuiation and propagation of DNA damage, iLe. genetic changes. Common types of genetic changes in neoplastic cells are, in addition to point mutations, amplifications and gross, structural alterations, such as translocations.

The amplification of DNA sequences may indicate specific functional requirement as illustrated in the DHFR experimental system. Therefore, the amplification of certain oncogenes in malignancies points toward a causative role of these genes in the process of malignant transformation and maintenance of the transformed phenotype. This hypothesis has gained support in recent studies. For example, the bcl-2 protein was found to be amplified in certain types of non-Hodgkin's lymphoma. This protein inhibits apoptosis and leads to the progressive accumulation of neoplastic cells. Members of the gene family of growth factor receptors have been found to be amplified in various types of cancers suggesting that overexpression of these receptors may make neoplastic cells less susceptible to limiting amounts of available growth factor. Examples include the amplification of the androgen receptor in recurrent prostate cancer during androgen deprivation therapy and the amplification of the growth factor receptor homologue ERB2 in breast cancer. Lastly, genes involved in intracellular signaling and control of cell cycle progression can undergo amplification during malignant transformation. This is illustrated by the amplification of the bcl-1 and ras genes in various epithelial and lymphoid neoplasms.

These earlier studies illustrate the feasibility of identifying amplified DNA sequences in neoplasms, because this approach can identify genes important for malignant transformation. The case of ERB2 also demonstrates the feasibility from a therapeutic standpoint, since transforming proteins may represent novel and specific targets for tumor therapy.

Several different techniques can be used to demonstrate amplified genomic sequences. Classical cytogenctic analysis of chromosome spreads prepared from cancer cells is adequate to identify gross structural alterations, such as translocations, deletions and inversions. Amplified genomic regions can only be visualized, if they involve large regions with high copy numbers or are present as extrachromosomal material. While cytogenetics was the first technique to demonstrate the consistent association of specific chromosomal changes with particular neoplasms it is inadequate for the identification and isolation of manageable DNA sequences. The more recently developed technique of comparative genomic hybridization (CGH) has illustrated the widespread phenomenon of genomic amplification in neoplasms. Tumor and normal DNA are hybridized simultaneously onto metaphases of normal cells and the entire genome can be screened by image analysis for DNA sequences that are present in the tumor at an increased frequency. (WO 93/18,186; Gray et al., *Radiation Res.* 137, 275–289 [1994]) As a screening method, this type of analysis has revealed a large number of recurring amplicons (a stretch of amplified DNA) in a variety of human neoplasms. Although CGH is more sensitive than classical cytogenetic analysis in identifying amplified stretches of DNA, it does not allow a rapid identification and isolation of coding sequences within the amplicon by standard molecular genetic techniques.

The most sensitive methods to detect gene amplification are polymerase chain reaction (PCR)-based assays. These assays utilize very small amount of tumor DNA as starting material, are exquisitely sensitive, provide DNA that is amenable to further analysis, such as sequencing and are suitable for high-volume throughput analysis.

The above-mentioned assays are not mutually exclusive, but are frequently used in combination to identify amplifications in neoplasms. While cytogenetic analysis and CGH represent screening methods to survey the entire genome for amplified regions, PCR-based assays are most suitable for the final identification of coding sequences, i.e. genes in amplified regions.

According to the present invention, such genes have been identified by quantitative PCR (S. Gelmini et al., *Clin. Chem.* 43:752 [1997]), by comparing DNA from a variety of primary tumors, including breast, lung, colon, prostate, brain, liver, kidney, pancreas, spleen, thymus, testis, ovary, uterus, etc. tumor, or tumor cell lines, with pooled DNA from healthy donors. Quantitative PCR was performed using a TaqMan instrument (ABI). Gene-specific primers and fluorogenic probes were designed based upon the coding sequences of the DNAs.

If Human lung carcinoma cell lines include A549 (SRC768), Calu-1 (SRC769), Calu-6 (SRC770), H157 (SRC771), H441 (SRC772), H460 (SRC773), H522 (SRC832), H810 (SRC833), SKMES-1 (SRC774) and SW900 (SRC775), all available from ATCC. Primary human lung tumor cells usually derive from adenocarcinomas, squamous cell carcinomas, large cell carcinomas, non-small cell carcinomas, small cell carcinomas, and broncho alveolar carcinomas, and include, for example, SRC724 (squamous cell carcinoma abbreviated as "SqCCa")(LT1), SRC725 (non-small cell carcinoma, abbreviated as "NSCCa")(LT1a), SRC726 (adenocarcinoma, abbreviated as "AdenoCa") (LT2), SRC727 (adenocarcinoma)(LT3), SRC728 (squamous cell carcinoma)(LT4), SRC729 (adenocarcinoma)(LT6), SRC730 (adeno/squamous cell carcinoma)(LT7), SRCC731 (adenocarcinoma)(LT9), SRC732 (squamous cell carcinoma)(LT10), SRC733 (adenocarcinoma)(LT11), SRC734 (adenocarcinoma) (LT12), SRC735 (broncho alveolar carcinoma, abbreviated as "BAC")(LT13), SRC736 (squamous cell carcinoma) (LT15), SRC737 (squamous cell carcinoma)(LT16), SRC738 (squamous cell carcinoma)(LT17), SRC739 (squamous cell carcinoma)(LT18), SRC740 (squamous cell carcinoma)(LT19), SPC741 (lung cell carcinoma, abbreviated as "LCCa")(LT21), SRC811 (adenocarcinoma)(LT22).

Colon cancer cell lines include, for example, ATCC cell lines SW480 (adenocarcinoma, SRCC776), SW620 (lymph node metastasis of colon adenocarcinoma, SRC777), Colo320 (carcinoma, SRCC778), Colo205 (carcinoma, SRC828), HCC2998 (carcinoma, SRC830), HT29 (adenocarcinoma, SRC779), HM7 (carcinoma, SRC780), KM12 (carcinoma, SRC831), CaWiDr (adenocarcinoma, SRC781), HCT15 (carcinoma, SRC829), HCT116 (carcinoma, SRC782), SKCO1 (adenocarcinoma, SRC783), SW403 (adenocarcinoma, SRC784), LS174T (carcinoma, SRC785), and HM7 (a high mucin producing variant of ATCC colon adenocarcinoma cell line LS 174T, obtained from Dr. Robert Warren, UCSF). Primary colon tumors include colon adenoocarcinomas designated CT1 (SRC751), CT2 (SRC742), CT3 (SRC743), CT4 (SRC752), CT5 (SRC753), CT6 (SRC754), CT7 (SRC755), CT8 (SRC744), CT9 (SRC756), CT10 (SRC745), CT11 (SRC757), CT12 (SRC746), CT14 (SCR754), CT15 (SRC748), CT16 (SRC749), CT17 (SRC750), CT19 (SRCC758).

Human breast carcinoma cell lines include, for example, HBL100 (SRCC759), MB435s (SRCC760), T47D (SRCC761), MB468(SRCC762), MB175 (SRCC763), MB361 (SRCC764), BT20 (SRCC765), MCF7 (SRCC766), SKBR3 (SRCC767).

G. Tissue Distribution

The results of the gene amplification assays herein can be verified by further studies, such as, by determining mRNA expression in various human tissues.

As noted before, gene amplification and/or gene expression in various tissues may be measured by conventional Southern blotting, Northern blotting to quantitate the transcription of mRNA (Thomas, *Proc. Natl. Acad. Sci. USA*, 77:5201–5205 [1980]), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes.

Gene expression in various tissues, alternatively, may be measured by immunological methods, such as immunohistochemical staining of tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence PRO213, PRO1330, PRO1449, PRO237, PRO324, PRO351, PRO362, PRO615, PRO531, PRO538, PRO3664, PRO618, PRO772 or PRO703 polypeptide or against a synthetic peptide based on the DNA sequences provided herein or against exogenous sequence fused to sequence PRO213, PRO1330, PRO1449, PRO237, PRO324, PRO351, PRO362, PRO615, PRO531, PRO538, PRO3664, PRO618, PRO772 or PRO703 DNA and encoding a specific antibody epitope. General techniques for generating antibodies, and special protocols for Northern blotting and in situ hybridization are provided hereinbelow.

H. Chromosome Mapping

If the amplification of a given gene is functionally relevant, then that gene should be amplified more than neighboring genomic regions which are not important for tumor survival. To test this, the gene can be mapped to a particular chromosome, e.g. by radiation-hybrid analysis. The amplification level is then determined at the location identified, and at neighboring genomic region. Selective or preferential amplification at the genomic region to which to gene has been mapped is consistent with the possibility that the gene amplification observed promotes tumor growth or survival. Chromosome mapping includes both framework and epicenter mapping. For further details see e.g., Stewart et at., *Genome Research* 7, 422–433 (1997).

I. Antibody Binding Studies

The results of the gene amplification study can be further verified by antibody binding studies, in which the ability of anti-PRO201, anti-PRO308 or anti-PRO309 to inhibit the expression of the PRO201, PRO308 or PRO309 polypeptides on tumor (cancer) cells is tested. Exemplary antibodies include polyclonal, monoclonal, humanized bispecific, and heteroconjugate antibodies, the preparation of which will be described hereinbelow.

Antibody binding studies may be carried out in any known assay method, such as competitive binding assays, direct and indirect sandwich assays, and immunoprecipitation assays. Zola, *Monoclonal Antibodies: A Manual of Techniques*, pp. 147–158 (CRC Press, Inc., 1987).

Competitive binding assays rely on the ability of a labeled standard to compete with the test sample analyte for binding with a limited amount of antibody. The amount of target protein (encoded by a gene amplified in a tumor cell) in the test sample is inversely proportional to the amount of standard that becomes bound to the antibodies. To facilitate determining the amount of standard that becomes bound, the antibodies preferably are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tumor sample may be fresh or frozen or may be embedded in paraffin and fixed with a preservative such as formalin, for example.

J. Cell-Based Tumor Assays

Cell-based assays and animal models for tumors (eg. cancers) can be used to verify the findings of the gene amplification assay, and further understand the relationship between the genes identified herein and the development and pathogenesis of neoplastic cell growth. The role of gene products identified herein in the development and pathology of tumor or cancer can be tested by using primary tumor cells or cells lines that have been identified to amplify the genes herein. Such cells include, for example, the breast, colon and lung cancer cells and cell lines listed above.

In a different approach, cells of a cell type known to be involved in a particular tumor are transfected with the cDNAs herein, and the ability of these cDNAs to induce excessive growth is analyzed. Suitable cells include, for example, stable tumor cells lines such as, the B104-1-1 cell line (stable NIH-3T3 cell line transfected with the neu protooncogene) and ras-transfected NIH-3T3 cells, which can be transfected with the desired gene, and monitored for tumorogenic growth. Such transfected cell lines can then be used to test the ability of poly- or monoclonal antibodies or antibody compositions to inhibit tumoroenic cell growth by exerting cytostatic or cyotoxic activity on the growth of the transformed cells, or by mediating antibody-dependent cellular cytotoxicity (ADCC). Cells transfected with the coding sequences of the genes identified herein can further be used to identify drug candidates for the treatment of cancer.

In addition, primary cultures derived from tumors in transgenic animals (as described below) can be used in the cell-based assays herein, although stable cell lines are preferred. Techniques to derive continuous cell lines from transgenic animals are well known in the art (see, eg. Small et al., *Mol. Cell. Biol.* 5, 642–648 [1985]).

K. Animal Models

A variety of well known animal models can be used to further understand the role of the genes identified herein in the development and pathogenesis of tumors, and to test the efficacy of candidate therapeutic agents, including antibodies, and other antagonists of the native potypeptides, including small molecule antagonists. The in vivo nature of such models makes them particularly predictive of responses in human patients. Animal models of tumors and cancers (e.g. breast cancer, colon cancer, prostate cancer, lung cancer, etc.) include both non-recombinant and recombinant (transgenic) animals. Non-recombinant animal models include, for example, rodent, e.g., murine models. Such models can be generated by introducing tumor cells into syngeneic mice using standard techniques, e.g. subcutaneous injection, tail vein injection, spleen implantation, intraperitoneal implantation, implantation under the renal capsule, or orthopin implantation, e.g. colon cancer cells implanted in colonic tissue. (See, e.g. PCT publication No. WO 97/33551, published Sep. 18, 1997).

Probably the most often used animal species in oncological studies are immunodeficient mice and, in particular, nude mice. The observation that the nude mouse with hypo/aplasia could successfully act as a host for human tumor xenografts has lead to its widespread use for this purpose. The autosomal recessive nu gene has been introduced into a very large number of distinct congenic strains of nude mouse, including, for example, ASW, A/He, AKR, BALB/c, B10.LP, C17, C3H, C57BL, C57, CBA, DBA, DDD, 1/st, NC, NFR, NFS, NFS/N, NZB, NZC, NZW, P. PIII and SJL. In addition, a wide variety of other animals with inherited immunological defects other than the nude mouse have been bred and used as recipients of tumor xenografts. For further details see, e.g. *The Nude Mouse in Oncology Research*, E. Boven and B. Winograd, eds., CRC Press, Inc., 1991.

The cells introduced into such animals can be derived from known tumor/cancer cell lines, such as, any of the above-listed tumor cell lines, and, for example, the B104-1-1 cell line (stable NIH-3T3 cell line transfected with the neu protooncogene); ras-transfected NIH-3T3 cells; Caco-2 (ATCC HTB-37); a moderately well-differentiated grade II human colon adenocarcinoma cell line, HT-29 (ATCC HTB-38), or from tumors and cancers. Samples of tumor or cancer cells can be obtained from patients undergoing surgery, using standard conditions, involving freezing and storing in liquid nitrogen (Karmali et al., *Br. J. Cancer* 48: 689–696 [1983]).

Tumor cells can be introduced into animals, such as nude mice, by a variety of procedures. The subcutaneous (s.c.) space in mice is very suitable for tumor implantation. Tumors can be transplanted s.c. as solid blocks, as needle biopsies by use of a trochar, or as cell suspensions. For solid block or trochar implantation, tumor tissue fragments of suitable size are introduced into the s.c. space. Cell suspensions are freshly prepared from primary tumors or stable tumor cell lines, and injected subcutaneously. Tumor cells can also be injected as subdermal implants. In this location, the inoculum is deposited between the lower part of the dermal connective tissue and the s.c. tissue. Boven and Winograd (1991), supra.

Animal models of breast cancer can be generated, for example, by implanting rat neuroblastoma cells (from which the neu oncogen was initially isolated), or neu-transformed NIH-3T3 cells into nude mice, essentially as described by Drebin et al. *PNAS USA* 83: 9129–9133 (1986).

Similarly, animal models of colon cancer can be generated by passaging colon cancer cells in animals, e.g. nude mice, leading to the appearance of tumors in these animals. An orthotopic transplant model of human colon cancer in nude mice has been described, for example, by Wang et al., *Cancer Research* 54: 4726–4728 (1994) and Too et al., *Cancer Research* 55, 681–684 (1995). This model is based on the so-called "METAMOUSE" sold by AntiCancer, Inc. (San Diego, Calif.).

Tumors that arise in animals can be removed and cultured in vitro. Cells from the in vitro cultures can then be passaged to animals. Such tumors can serve as targets for further testing or drug screening. Alternatively, the tumors resulting from the passage can be isolated and RNA from pre-passage cells and cells isolated after one or more rounds of passage analyzed for differential expression of genes of interest. Such passaging techniques can be performed with any known tumor or cancer cell lines.

For example, Meth A, CMS4, CMS5, CMS21, and WEHI-164 are chemically induced fibrosarcomas of BALB/c female mice (DeLeo et al., *J. Exp. Med.* 146: 720 [1977]), which provide a highly controllable model system for studying the anti-tumor activities of various agents (Palladino et al., *J. Immunol.* 138: 4023–4032 [1987]). Briefly, tumor cells are propagated in vitro in cell culture. Prior to injection into the animals, the cell lines are washed and suspended in buffer, at a cell density of about $10 \times 10^6$, to $10 \times 10^7$ cells/ml. The animals are then infected subcutaneously with 10 to 100 µl of the cell suspension, allowing one to three weeks for a tumor to appear.

In addition, the Lewis lung (3LL) carcinoma of mice, which is one of the most thoroughly studied experimental tumors, can be used as an investigational tumor model. Efficacy in this tumor model has been correlated with beneficial effects in the treatment of human patients diagnosed with small cell carcinoma of the lung (SCCL). This tumor can be introduced in normal mice upon injection of tumor fragments from an affected mouse or of cells maintained in culture (Zupi et al., *Br. J. Cancer* 41: suppl. 4,309 [1980]), and evidence indicates that tumors can be started from injection of even a single cell and that a very high proportion of infected tumor cells survive. For further information about this tumor model see Zacharski, *Haemostasis* 16: 300–320 [1986]).

One way of evaluating the efficacy of a test compound in an animal model is implanted tumor is to measure the size of the tumor before and after treatment. Traditionally, the size of implanted tumors has been measured with a slide caliper in two or three dimensions. The measure limited to two dimensions does not accurately reflect the size of the tumor, therefore, it is usually converted into the corresponding volume by using a mathematical formula. However, the measurement of tumor size is very inaccurate. The therapeutic effects of a drug candidate can be better described as treatment-induced growth delay and specific growth delay. Another important variable in the description of tumor growth is the tumor volume doubling time. Computer programs for the calculation and description of tumor growth are also available, such as the program reported by Rygaard and Spang-Thomsen, *Proc. 6th Int. Workshop on Immune-Deficient Animals*, Wu and Sheng eds., Basel, 1989, 301. It is noted, however, that necrosis and inflammatory responses following treatment may actually result in an increase in tumor size, at least initially. Therefore, these changes need to be carefully monitored, by a combination of a morphometric method and flow cytometric analysis.

Recombinant (transgenic) animal models can be engineered by introducing the coding portion of the genes identified herein into the genome of animals of interest, using standard techniques for producing transgenic animals. A transgenic animal is one containing a "transgene" or genetic material integrated into the genome introduced into the animal itself or an ancestor of the animal at a prenatal stage (e.g., embryonic stage). Animals that can serve as a target for transgenic manipulation include, without limitation, mice, rats, rabbits, guinea pigs, sheep, goats, pigs, and non-human primates, eg. baboons, chimpanzees and monkeys. Techniques known in the art to introduce a transgene into such animals include pronucleic microinjection (Hoppe and Wanger, U.S. Pat. No. 4,873,191); retrovirus-mediated gene transfer into germ lines (e.g., Van der Putten et al., *Proc. Natl. Acad. Sci. USA* 82: 6148–615 [1985]); gene targeting in embryonic stem cells (Thompson et al., *Cell* 56: 313–321 [1989]); electroporation of embryos (Lo, *Mol. Cel. Biol.* 3: 1803–1814 [1983]); sperm-mediated gene transfer (Lavitrano et al., *Cell* 57: 717–73 [1989]). For review, see, for example, U.S. Pat. No. 4,736,866 and U.S. Pat. No. 4,870,009.

Typically, particular cells would be targeted for PRO201, PRO308 or PRO309 transgene incorporation with tissue-specific enhancers. Transgenic animals that include a copy of a transgene encoding a PRO201, PRO308 or PRO309 introduced into the germ line of the animal at an embryonic stage can be used to examine the effect of increased expression of DNA encoding PRO201, PRO308 or PRO309. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

For the purpose of the present invention, transgenic animals include those that carry the transgene only in part of their cells ("mosaic animals"). The transgene can be integrated either as a single transgene, or in concatamers, e.g., head-to-head or head-to-tail tandems. Selective introduction of a transgene into a particular cell type is also possible by following, for example, the technique of Lasko et al., *Proc. Natl. Acad. Sci. USA* 89: 6232–636 (1992).

The expression of the transgene in transgenic animals can be monitored by standard techniques. For example, Southern blot analysis or PCR amplification can be used to verify the integration of the transgene. The level of mRNA expression can then be analyzed using techniques such as in situ hybridization, Northern blot analysis, PCR, or immunocytochemistry. The animals are further examined for signs of tumor or cancer development.

Alternatively, "knock out" animals can be constructed which have a defective or altered gene encoding a PRO201, PRO308 or PRO309 polypeptide identified herein, as a result of homologous recombination between the endogenous gene encoding the polypeptide and altered genomic DNA encoding the same polypeptide introduced into an embryonic cell of the animal. For example, cDNA encoding a PRO201, PRO308 or PRO309 polypeptide can be used to clone genomic DNA encoding that polypeptide in accordance with established techniques. A portion of the genomic DNA encoding a particular PRO201, PRO308 or PRO309 polypeptide can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell*, 51: 503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell*, 69: 915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113–1521. A chimeric embryo can then be implanted into a suitable pseudopregnant female foster animal and the embryo brought to term to create a "knock out" animal. Progeny harboring the homoiogously recombined DNA in their germ cells can be identified by standard techniques and used to breed animals in which all cells of the animal contain the homologously recombined DNA. Knockout animals can be characterized for instance, by their ability to defend against certain pathological conditions and by their development of pathological conditions due to absence of the PRO201, PRO308 or PRO309 polypeptide.

The efficacy of antibodies specifically binding the polypeptides identified herein and other drug candidates, can be tested also in the treatment of spontaneous animal tumors. A suitable target for such studies is the feline oral squamous cell carcinoma (SCC). Feline oral SCC is a highly invasive, malignant tumor that is the most common oral malignancy of cats, accounting for over 60% of the oral tumors reported in this species. It rarely metastasizes to distant sites, although this low incidence of metastasis may merely be a reflection of the short survival times for cats with this tumor.

These tumors are usually not amenable to surgery, primarily because of the anatomy of the feline oral cavity. At present, there is no effective treatment for this tumor. Prior to entry into the study, each cat undergoes complete clinical examination, biopsy, and is scanned by computed tomography (CT). Cats diagnosed with subligual oral squamous cell tumors are excluded from the study. The tongue can become paralyzed as a result of such tumor, and even if the treatment kills the tumor, the animals may not be able to feed themselves. Each cat is treated repeatedly, over a longer period of time. Photographs of the tumors will be taken daily during the treatment period, and at each subsequent recheck. After treatment, each cat undergoes another CT scan. CT scans and thoracic radiograms are evaluated every 8 weeks thereafter. The data are evaluated for differences in survival, response and toxicity as compared to control groups. Positive response may require evidence of tumor regression, preferably with improvement of quality of life and/or increased life span.

In addition, other spontaneous animal tumors, such as fibrosarcoma, adenocarcinoma, lymphoma, chrondroma, leiomyosarcoma of dogs, cats, and baboons can also be tested. Of these mammary adenocarcinoma in dogs and cats is a preferred model as its appearance and behavior are very similar to those in humans. However, the use of this model is imrited by the rare occurrence of this type of tumor in animals.

L. Screening Assays for Drug Candidates

Screening assays for drug candidates are designed to identify compounds that bind or complex with the polypeptides encoded by the genes identified herein, or otherwise interfere with the interaction of the encoded polypeptides with other cellular proteins. Such screening assays will include assays amenable to high-throughput screening of chemical libraries, making them particularly suitable for identifying small molecule drug candidates. Small molecules contemplated include synthetic organic or inorganic compounds, including peptides, preferably soluble peptides, (poly)peptide-immunoglobulin fusions, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. The assays can be performed in a variety of formats, including protein-protein binding assays, biochemical screening assays, immunoassays and cell based assays, which are well characterized in the art.

All assays are common in that they call for contacting the drug candidate with a polypeptide encoded by a nucleic acid identified herein under conditions and for a time sufficient to allow these two components to interact.

In binding assays, the interaction is binding and the complex formed can be isolated or detected in the reaction mixture. In a particular embodiment. the polypeptide encoded by the gene identified herein or the drug candidate is immobilized on a solid phase, e.g. on a microliter plate, by covalent or non-covalent attachments. Non-covalent attachment generally is accomplished by coating the solid surface with a solution of the polypeptide and drying. Alternatively, an immobilized antibody, e.g. a monoclonal antibody, specific for the polypeptide to be immobilized can be used to anchor it to a solid surface. The assay is performed by adding the non-immobilized component, which may be labeled by a detectable label, to the immobilized component, e.g. the coated surface containing the anchored component. When the reaction is complete, the non-reacted components are removed, e.g. by washing, and complexes anchored on the solid surface are detected. When the originally non-immobilized component cares a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular PRO201, PRO308 or PRO309 polypeptide encoded by a gene identified herein, its interaction with that polypeptide can be assayed by methods well known for detecting protein-protein interactions. Such assays include traditional approaches, such as, cross-linking, co-immunoprecipitation, and co-purification through gradients or chromatographic columns. In addition, protein-protein interactions can be monitored by using a yeast-based genetic system described by Fields and co-workers [Fields and Song, *Nature* 340: 245–246 (1989); Chien et al., *Proc. Natl. Acad. Sci. USA* 88: 9578–95(1991)] as disclosed by Chevray and Nathans [*Proc. Natl. Acad Sci. USA* 89: 5789–5793 (1991)]. Many transcriptional activators, such as yeast GAL4, consist of two physically discrete modular domains, one acting as the DNA-binding domain, while the other one functioning as the transcription activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a PRO201-, PRO308- or PRO309-encoding gene identified herein and other intra- or extracellular components can be tested as follows: usually a reaction mixture is prepared containing the product of the amplified gene and the intra- or extracellular component under conditions and for a time allowing for the interaction and binding of the two products. To test the ability of a test compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

M. Compositions and Methods for the Treatment of Tumors

The compositions useful in the treatment of tumors associated with the amplification of the genes identified herein include, without limitation, antibodies, small organic and inorganic molecules, peptides, phosphopeptides, antisense and ribozyme molecules, triple helix molecules, etc. that inhibit the expression and/or activity of the target gene product.

For example, antisense RNA and RNA molecule act to directly block the translation of mRNA by hybridizing to targeted mRNA and preventing protein translation. When antisense DNA is used, oligodeoxyribonucleotides derived from the translation initiation site, e.g. between about −10 and +10 position of the target gene nucleotide sequence, are preferred.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g. Rossi, *Current Biology* 4: 469–471 (1994), and PCT publication No. WO 97/33551 (published Sep. 18, 1997).

Nucleic acid molecules in triple helix formation used to inhibit transcription should be single-stranded and composed of deoxynucleotides. The base composition of these oligonucleotides is designed such that it promotes triple helix formation via Hoogsteen base pairing rules, which generally require sizeable stretches of purines or pyrimidines on one strand of aduplex. For further details see, e.g. PCT publication No. WO 97/33551, supra.

These molecules can be identified by any or any combination of the screening assays discussed hereinabove and/or by any other screening techniques well known for those skilled in the art.

N. Anti-PRO201, PRO308 or PRO309 Antibodies

The present invention further provides anti-PRO201, anti-PRO308 or anti-PRO309 antibodies. Exemplary antibodies include polyclonal, monoclonal, humanized, bispecific, and heteroconjugate antibodies. Some of the more promising drug candidates according to the present invention are antibodies and antibody fragments which may inhibit the production or the gene product of the amplified genes identified herein and/or reduce the activity of the gene products.

1. Polyclonal Antibodies

The anti-PRO201, anti-PRO308 or anti-PRO309 antibodies may comprise polyclonal antibodiies. Methods of preparing polyclonai antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the PRO201, PRO308 or PRO309 potypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-PRO201, anti-PRO308 or anti-PRO309 antibodies may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the PRO201, PRO308 or PRO309 polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antihodies: Principles and Practice*, Academic Press, (1986) pp. 59–103]. Immortalized cell lines are usually transformed mammalian cells, particularly mycloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lackc the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium, More preferred immortalized cell lines are murine mycioma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and applications*, Marcel Dekker, Inc., New York, (1987) pp. 51–631.

The culture medium in which the hybridoma cells are cultured can then be assayed for the presence of monoclonal antibodies directed against PRO201, PRO308 or PRO309. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] by covalently joining to the immunoglobulin coding sequence all or part of the coding sequence for a non-immunoglobulin polypeptide. Such a non-immunogiobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Humanized Antibodies

The anti-PRO201, PRO308 or PRO309 antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the CDR regions are those of a human immunoglobulin consensus sequence. The humanized antibody optimally also will comprise at least a portion of an immunoglobulin constant region (Fc), typically that of a human immunoglobulin [Jones et al., *Nature*, 321:522–525 (1986); Riechmann et al., *Nature*, 332:323–329 (1988); and Presta, *Curr. Op. Struct. Biol.*, 2:593–596 (1992)].

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers [Jones et al., *Nature*, 321:522–525 (1986); Riechmann et al., *Nature*, 332:323–327 (1988); Verhoeyen el al., *Science*, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86–95 (1991)].

4. Antibody Dependent Enzyme Mediated Prodrug Therapy (ADEPT)

The antibodies of the present invention may also be used in ADEPT by conjugating the antibody to a prodrug-activating enzyme which converts a prodrug (e.g. a peptidyl chemotherapeutic agent, see WO 81/01145) to an active anti-cancer drug. See, for example, WO 88/07378 and U. S. Pat. No. 4,975,278.

The enzyme component of the immunoconjugate useful for ADEPT includes any enzyme capable of acting on a prodrug in such as way so as to convert it into its more active, cytotoxic fonn.

Enzymes that are useful in the method of this invention include, but are not limited to, glycosidase, glucose oxidase, human lysosyme, human glucuronidase, alkaline phosphatase useful for converting phosphate-containing prodrugs into free drugs; aryisulfatase useful for converting sulfate-containing prodrugs into free drugs; cytosine deaminase useful for converting non-toxic 5-fluorocytosine into the anti-cancer drug 5-fluorouracil; proteases, such as serratia protease, thermolysin, subtilisin, carboxypeptidases (e.g., carboxypeptidase G2 and carboxypeptidase A) and cathepsins (such as cathepsins B and L), that are useful for converting peptide-containing prodrugs into free drugs; D-alanylcarboxypeptidases, useful for converting prodrugs that contain D-amino acid substituents; carbohydrate-cieaving enzymes such as , β-galactosidase and neuraminidase useful for converting glycosylated prodrugs into free drugs; β-lactamase useful for converting drugs derivatized with β-lactams into free drugs; and penicillin amidases, such as penicillin Vamidase or penicilli G amidase, useful for converting drugs derivatized at their amine nitrogens with phenoxyacetyl or phenylacetyl groups, respectively, into free drugs. Alternatively, antibodies with enzymatic activity, also known in the art as "abzymes" can be used to convert the prodrugs of the invention into free active drugs (see, e.g., Massey, *Nature* 328: 457–58 (1987)). Antibody-abzyme conjugates can be prepared as described herein for delivery of the abzyme to a tumor cell population.

The enzymes of this invention can be covalently bound to the anti-PRO201, anti-PRO308 or anti-PRO309 antibodies by techniques well known in the art such as the use of the heterobifunctional cross-linking agents discussed above. Alternatively, fusion proteins comprising at least the antigen binding region of the antibody of the invention linked to at least a functionally active portion of an enzyme of the invention can be constructed using recombinant DNA techniques well known in the art (see, e.g. Neuberger et al., *Nature* 312: 604–608 (1984)).

5. Bispeciric Antibodies

Bispecific antibodies are monoclonal, preferably human or humanized, antibodies that have binding specificities for at least two different antigens. In the present case, one of the binding specificities is for the PRO201, PRO308 or PRO309, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, *Nature*, 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Trauneeker et al., *EMBO J.*, 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at icat part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (eg. F(ab')$_2$ bispecific antibodies). Techniques for generating bispecific antibodies from antibody fragments have been described in the literature. For example, bispecific antibodies can be prepared can be prepared using chemical linkage. Brennan et al., *Science* 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med.* 175: 217–225 (1992) describe the production of a fully humanized bispecific antibody F(ab')$_2$ molecule. Each Fab' fragment was separately secreted from *E. coil* and subjected to directed chemical coupling in vitro to form the bispecific antibody. Tche bispecific antibody thus formed was able to bind to cells overexpressing the ErbB2 receptor and normal human T cells, as well as trigger the lytic activity of human cytotoxic lymphocytes against human breast tumor targets.

Various technique for making and isolating bispecific antibody fragments directly from recombinant cell culture have also been described. For example, bispecific antibodies have been produced using leucine zippers, Kosteiny et al., *J. Immunol.* 148(5): 1547–1553 (1992), wherein the leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90: 6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., *J. Immunol.* 152: 5368 (1994).

Antibodies with more than two valencies are contemplated. For example, trispecific antibodies can be prepared. Tutt et al., *J. Immunol.* 147: 60 (1991).

Exemplary bispecific antibodies may bind to two different epitopes on a given "Pro" protein herein. Alternatively, an anti-"PRO" protein arm may be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular "PRO" protein. Bispecific antibodies may also be used to localize cytotoxic agents to cells which express a particular "PRO" polypeptide. These antibodies possess a "PRO"-binding arm and an arm which binds a cytotoxic agent or a radionuclide chelator, such as EOTUBE, DPTA, DOTA, or TETA. Another bispecific antibody of interest binds the "PRO" polypeptide and further binds tissue factor (TF).

6. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,9801], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

7. Effector Function Engineering

It may be desirable to modify the antibody of the invention with respect to effector function, so as to enhance the effectiveness of the antibody in treating cancer, for example. For example cysteine residue(s) may be introduced in the Fc region, thereby allowing interchain disulfide bond formation in this region. The homoditneric antibody thus generated may have improved internalization capability and/or increased complement-mediated cell killing and antibody-dependent cellular cytotoxicity (ADCC). See Caron et al., *J. Exp Med.* 176:1191–1195 (1992) and Shopes, B. *J. Immunol.* 148:2918–2922 (1992). Homodimeric antibodies with enhanced anti-tumor activity may also be prepared using heterobifunctional cross-linkers as described in Wolff et al. *Cancer Research* 53:2560–2565 (1993). Alternatively, an atibody can be engineered which has dual Fc regions and may thereby have enhanced complement lysis and ADCC capabilities. See Stevenson el al., *Anti-Cancer Drug Design* 3: 219–230 (1989).

8. Immunoconjugates

The invention also pertains to immunoconjugates comprising an antibody conjugated to a cytotoxic agent such as a chemotherapeutic agent, toxin (e.g. an enzymatically active toxin of bacterial, fungal, plant or animal origin, or fragments thereof, or a small molecule toxin), or a radioactive isotope (i e., a radioconjugate).

Chemotherapeutic agents useful in the generation of such immunoconjugates have been described above. Enzymatically active protein toxins and fragments thereof which can be used include diphtheria A chain, nonbinding active fragments of diphtheria toxin, cholera toxin, botulinus toxin, exotoxin A chain (from Pseudomonas aeruginosa), ricin A chain, abrin A chain, modeccin A chain, alpha-sarcin, *Aleurites fordii* proteins, dianthin proteins, *Phytolaca american* proteins (PAPI, PAPII, and PAP-S), momordica charantia inhibitor, curcin, crotin, sapaonaria officinalis inhibitor, gelonin, saporin, mitogellin, restrictocin, phenomycin, enomycin and the tricothecenes. Small molecule toxins include, for example, calicheamicins, maytansinoids, palytoxin and CC1065. A variety of radionuclides are available for the production of radioconjugated antibodies. Examples include $^{212}Bi$, $^{131}I$, $^{131}In$, $^{90}Y$ and $^{186}Re$.

Conjugates of the antibody and cytotoxic agent are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tumor pretargeting wherein the antibody-receptor conjugate is adtninistered to the patient, followed by removal of unbound conjugate from the circulation using a clearing agent and then administration of a "ligand" (e.g. avidin) which is conjugated to a cytotoxic agent (e.g. a radionucleotide).

9. Immunoliposomes

The antibodies disclosed herein may also be formulated as immunoliposomes. Liposomes containing the antibody are prepared by methods known in the art, such as described in Epstein et al., *Proc. Natl. Acad. Sci. USA*, 82:3688 (1985); Hwang et al., *Proc. Natl. Acad. Sci. USA*, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257: 286–288 (1982) via a disulfide interchange reaction. A chemotherapeutic agent (such as Doxorubicin) is optionally contained within the liposome. See Gabizon et al., *J. National Cancer Inst.* 81(19): 1484 (1989).

O. Uses for anti-PRO201, PRO308 or PRO309 Antibodies

The anti-PRO201, anti-PRO308 or anti-PRO309 antibodies of the invention have various utilities. For example, anti-PRO201, anti-PRO308 or anti-PRO309 antibodies may be used in diagnostic assays for PRO201, PRO308 or PRO309, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodfies: A Manual of Techniques*, CRC Press, Inc. (1987) pp. 147–158]. The antibodies used in the diagnostic assays can be labeled with a detectable moiety. The detectable moiety should be capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

Anti-PRO201, anti-PRO308 or anti-PRO309 antibodies also are useful for the affinity purification of PRO201, PRO308 or PRO309 from recombinant cell culture or natural sources. In this process, the antibodies against PRO201, PRO308 or PRO309 are immobilized on a suitable support, such a Sephadex resin or filter paper, using methods well known in the art. The immobilized antibody then is contacted with a sample containing the PRO201, PRO308 or PRO309 to be purified, and thereafter the support is washed with a suitable solvent that will remove substantially all the material in the sample except the PRO201, PRO308 or PRO309, which is bound to the immobilized antibody. Finally, the support is washed with another suitable solvent that will release the PRO201, PRO308 or PRO309 from the antibody.

P. PRO201, PRO308 and PRO309 Antagonists

Several approaches may be suitably employed to create the antagonist and agonist compounds of the present invention. Any approach where the antagonist molecule can be targeted to the interior of the cell, which interferes or prevents wild type PRO201, PRO308 or PRO309 from normal operation is suitable. Additional properties of such antagonist or agonist molecules are readily determinable by one of ordinary skill, such as size, charge and hydrophobicity suitable for transmembrane transport.

Where mimics or other mammalian homologues of PRO201, PRO308 or PRO309 are to be identified or evaluated, the cells are exposed to the test compound and compared to positive controls which are exposed only to PRO201, PRO308 or PRO309 and to negative controls which were not exposed to either the compound or the natural ligand. Where antagonists or agonists of PRO201, PRO308 or PRO309 signal modulation are to be identified or evaluated, the cells are exposed to the compound of the invention in the presence of the natural ligand and compared to controls which are not exposed to the test compound.

Detection assays may by employed as a primary screen to evaluate the phosphatase inhibition/enhancing activity of the antagonist/agonist compounds of the invention. The assays may also be used to assess the relative potency of a compound by testing a range of concentrations, in a range from 100 mM to 1 pM, for example, and computing the concentration at which the amount of phosphorylation or signal transduction is reduced or increased by 50% ($IC_{50}$) compared to controls.

Assays can be performed to identify compounds that affect phosphorylation of PRO201, PRO308 or PRO309 substrates. Specifically, assays can be performed to identify compounds that increase the phosphorylation activity of PRO201, PRO308 or PRO309 or assays can be performed to identify compounds that decrease the phosphorylation of PRO201, PRO308 or PRO309 substrates. These assays can be performed either on whole cells themselves or on cell extracts. The assays can be performed in a variety of formats, including protein-protein binding assays, biochemical screening assays, immunoassays, cell based assays, etc. Such assay formats are well known in the art.

The screening assays of the present invention are amenable to high-throughput screening of chemical libraries, and are particularly suitable for identifying small molecule drug candidates.

(1) Antagonist and Agonist Molecules

To screen for antagonists and/or agonists of PRO201, PRO308 or PRO309 signaling, the assay mixture is incubated under conditions whereby, but for the presence of the candidate pharmacological agent, PRO201, PRO308 or PRO309 induces intracellular signaling (for example, association of Nsp1 (SEQ ID NO:1) with the EGF receptor) with a reference activity. The mixture components can be added in any order that provides for the requisite activity. Incubation may be performed at any temperature that facilitates optimal binding, typically between about 4° C. and 40° C., more commonly between about 15° and 40° C. Incubation periods are likewise selected for optimal binding but also minimized to facilitate rapid, high-throughput screening, and are typically between about 0.1 and 10 hours, preferably less than 5 hours, more preferably less than 2 hours. After incubation, the effect of the candidate pharmacological agent on the PRO201, PRO308 or PRO309 signaling is determined in any convenient way. For cell-free binding-type assays, a separation step is often used to separate bound and unbound components. Separation may, for example, be effected by precipitation (e.g. TCA precipitation, immunoprecipitation, etc.), immobilization (e.g. on a solid substrate), followed by washing. The bound protein is conveniently detected by taking advantage of a detectable label attached to it, e.g. by measuring radioactive emission, optical or electron density, or by indirect detection using, e.g. antibody conjugates.

Suitable molecules that affect the protein-protein interaction of PRO201, PRO308 or PRO309 and its binding proteins include fragments of the latter or small molecules, e.g., peptidomimetics, which will prevent interaction and proper complex formation. Such small molecules, which are usually less than 10 KD molecular weight, are preferable as therapeutics since they are more likely to be permeable to cells, are less susceptible to degradation by various cellular mechanisms, and are not as apt to elicit an immune response as proteins. Small molecules include but are not limited to synthetic organic or inorganic compounds. Many pharmaceutical companies have extensive libraries of such molecules, which can be conveniently screened by using the assays of the present invention. Non-limiting examples include proteins, peptides, glycoproteins, glycopeptides, glycolipids, polysaccharides, oligosaccardies, nucleic acids, bioorganic molecules, peptidomimetics, pharmacological agents and their metabolites, transcriptional and translation control sequences, and the like.

A preferred technique for identifying molecules which bind to PRO201, PRO308 or PRO309 utilizes a chimeric substrate (e.g., epitope-tagged fused or fused immunoadhesin) attached to a solid phase, such as the well of an assay plate. The binding of the candidate molecules, which are optionally labeled (e.g., radiolabeled), to the immobilized receptor can be measured. Alternatively, competition for interaction of Nsp1 with the binding proteins can be assayed. Further yet, molecules may be screened which affect the tumorigenicity of PRO201, PRO308 or PRO309 in NIH3T3 cells in nude mice. In screening for antagonists and/or agonists, PRO201, PRO308 or PRO309 can be exposed to a PRO201, PRO308 or PRO309 substrate followed by the putative antagonist and/or agonist, or the PRO201, PRO308 or PRO309 binding protein and antagonist and/or agonist can be added simultaneously, and the ability of the antagonist and/or agonist to block PRO201, PRO308 or PRO309 activation can be evaluated.

(2) Detection Assays

The PRO201, PRO308 or PRO309 polypeptides are useful in assays for identifying lead compounds for therapeutically active agents that modulate PRO201, PRO308 or PRO309 signaling. Specifically, lead compounds that either prevent the formation of PRO201, PRO308 or PRO309 signaling complexes or prevent or attenuate PRO201, PRO308 or PRO309 modulated can be conveniently identified.

(a) Biochemical Detection Techniques

Biochemical analysis techniques can be evaluated by a variety of techniques. One typical assay mixture which can be used with the present invention contains PRO201, PRO308 or PRO309 and a protein with which PRO201, PRO308 or PRO309 is normally directly or indirectly associated (e.g. Cas), usually in an isolated, partially pure or pure form. One or both of these components may be PRO201, PRO308 or PRO309 bound to another peptide or polypeptide, which may, for example, provide or enhance protein-protein binding, improve stability under assay conditions, etc. In addition, one of the components usually comprises or is coupled to a detectable label. The label may provide for direct detection by measuring radioactivity, luminescence, optical or electron density, etc., or indirect detection such as an epitope tag, an enzyme, etc. The assay mixture can additionally comprise a candidate pharmacological agent, and optionally a variety of other components, such as salts, buffers, carrier proteins, e.g. albumin, detergents, protease inhibitors, nuclease inhibitors, antimicrobial agents, etc., which facilitate binding, increase stability, reduce non-specific or background interactions, or otherwise improve the efficiency or sensitivity of the assay.

The following detection methods may also be used in a cell-free system wherein cell lysate containing the signal transducing substrate molecule and PRO201, PRO308 or PRO309 is mixed with a compound of the invention.

(i) Whole Cell Detection

A common technique involves incubating cells with vertebrate PRO201, PRO308 or PRO309 and radiolabeled phosphate, lysing the cells, separating cellular protein components of the lysate using an SDS-polyacrylamide gel (SDS-PAGE) technique, in either one or two dimensions, and detecting the presence of phosphorylated proteins by exposing X-ray film. Detection can also be effected without using radioactive labeling. In such a technique, the protein components (e.g., separated by SDS-PAGE) are transferred to a nitrocellulose membrane where the presence of phosphorylated tyrosine is detected using an antiphosphotyrosine antibody (anti pTyr).

Alternatively, the anti-pTyr can be conjugated with an enzyme, such as horseradish peroxidase, and detected by subsequent addition of a calorimetric substrate for the enzyme. A further alternative involves detecting the anti-pTyr by reacting with a second antibody that recognizes the anti-pTyr, this second antibody being labeled with either a radioactive moiety or an enzyme as previously described. Examples of these and similar techniques are described in Hansen et al., *Electrophoresis* 14: 112–126 (1993); Campbell et al., *J. Biol. Chem.* 268: 7427–7434 (1993); Donato et al., *Cell Growth Diff.* 3: 258–268 (1992); Katagiri et al., *J. Immunol.* 150: 585–593 (1993). Additionally, the anti-pTyr can be detected by labeling it with a radioactive substance, followed by scanning the labeled nitrocellulose to detect radioactivity or exposure of X-ray film.

(b) Biological Detection Techniques

The ability of the antagonist/agonist compounds of the invention to modulate the activity PRO201, PRO308 or PRO309, which itself modulates intracellular signaling, may also be measured by scoring for morphological or functional changes associated with ligand binding. Any qualitative or quantitative technique known in the art may be applied for observing and measuring cellular processes which comes under the control of PRO201, PRO308 or PRO309. For example, expression of Nsp1 (SEQ ID NO:1) in NIH3T3 cells causes formation of morphologically transformation of the cells. The presence and or number of these foci can be used as an indicator of biological efficacy of antagonists of agonists of Nsp1 signaling.

The data obtained from these cell culture assays cans be used in formulating a range of dosages for use in humans. The dosage of the compounds of the invention should lie within a range of circulating concentrations with little or no toxicity. The dosage may vary within this range depending on the dosage form employed and the route of administration.

(2) Antisense Nucleolides

Another preferred class of antagonists involves the use of gene therapy techniques, include the administration of antisense nucleotides. Applicable gene therapy techniques include single or multiple administrations of therapeutically effective DNA or mRNA. Antisense RNAs and DNAs can be used as therapeutic agents for blocking the expression of certain genes in vivo. Short antisense oligonucleotides can be imported into cells where they act as inhibitors, despite their low intracellular concentrations caused by restricted uptake by the cell membrane, Zamecnik et al., *Proc. Natl. Acad. Sci. USA* 83: 4143–4146 (1986). The oligonucleotides can be modified to enhance their uptake, e.g., by substituting their negatively charged phophodiester groups by uncharged groups.

There are a variety of techniques known for introducing nucleic acids into viable cells. The techniques vary depending upon whether the nucleic acid is transferred into cultured cells in vitro, ex vivo, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection, Dzau et al., *Trends Biotech*. 11: 205–210 (1993). In some situations it is desirable to provide the nucleic acid source with an agent that targets the target cells, such as an antibody specific for a cell surface membrane protein associated with endocytosis may be used for targeting and/or to facilitate uptake, e.g., capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., *J. Biol. Chem*. 262: 4429–4432 (1987); Wagner et al., *Proc. Natl. Acad. Sci. USA* 87: 3410–3414 (1990). For a review of known gene marking and gene therapy protocols, see Anderson et al., *Science* 256: 808–813 (1992).

In one embodiment, PRO201, PRO308 or PRO309 antagonist and/or agonist molecules may be used to bind endogenous ligand in the cell, thereby causing the cell to be unresponsive to PRO201, PRO308 or PRO309 wild type, especially when the levels of PRO201, PRO308 or PRO309 in the cell exceed normal physiological levels. Also, it may be beneficial to bind endogenous PRO201, PRO308 or PRO309 substrates or complexing agents that are activating undesired cellular responses (such as proliferation of tumor cells).

In a further embodiment of the invention, PRO201, PRO308 or PRO309 expression may be reduced by providing PRO201-, PRO308- or PRO309-expressing cells with an amount of PRO201, PRO308 or PRO309 antisense RNA or DNA effective to reduce expression of the PRO201, PRO308 or PRO309 protein.

In a further embodiment of the invention, the expression of binding partners of PRO201, PRO308 or PRO309 may be reduced by providing PRO201, PRO308 or PRO309 expressing cells with an amount of antisense RNA or DNA effective for reduced expression of the binding partners of PRO201, PRO308 or PRO309.

Q. Diagnostic Uses

Another use of the compounds of the invention (e.g., PRO201, PRO308 or PRO309, PRO201- , PRO308- or PRO309-variants and anti-PRO201, anti-PRO308 or anti-PRO309 antibodies) described herein is to help diagnose whether a disorder is driven, to some extent, by PRO201, PRO308 or PRO309 modulated signaling.

A diagnostic assay to determine whether a particular disorder is driven by PRO201, PRO308 or PRO0309 signaling, can be carried out using the following steps: (1) culturing test cells or tissues; (2) administering a compound which can inhibit Nsp1, Nsp2 or Nsp3 modulated signaling; and (3) measuring the degree of phosphorylation on the PRO201, PRO308 or PRO309 substrate in cell lysates or PRO201, PRO308 or PRO309 mediated phenotypic effects in the test cells. The steps can be carried out using standard techniques in light of the present disclosure. For example, standard techniques can be used to isolate cells or tissues and culturing or in vivo.

Compounds of varying degree of selectivity are useful for diagnosing the role of PRO201, PRO308 or PRO309. For example, compounds which inhibit PRO201, PRO308 or PRO309 in addition to another form of adaptor molecule can be used as an initial test compound to determine if one of several adaptor molecules drive the disorder. The selective compounds can then be used to further eliminate the possible role of the other adaptor proteins in driving the disorder. Test compounds should be more potent in inhibiting intracellular signaling activity than in exerting a cytotoxic effect (e.g., an $IC_{50/LD50}$ of greater than one). The $IC_{50}$ and $LD_{50}$ can be measured by standard techniques, such as an MTT assay, or by measuring the amount of LDH released. The degree of $IC_{50}/LD_{50}$ of a compound should be taken into account in evaluating the diagnostic assay. Generally, the larger the ratio the more relative the information. Appropriate controls take into account the possible cytotoxic effect of a compound of a compound, such as treating cells not associated with a cell proliferative disorder (e.g., control cells) with a test compound, can also be used as part of the diagnostic assay. The diagnostic methods of the invention involve the screening for agents that modulate the effects of fused upon hedgehog signaling. Exemplary detection techniques include radioactive labeling and immunoprecipitating (U.S. Pat. No. 5,385,915).

While cell surface proteins, such as growth receptors overexpressed in certain tumors are excellent targets for drug candidates or tumor (e.g. cancer) treatment, the same proteins along with secreted proteins encoded by the genes amplified in tumor cells find additional use in the diagnosis and prognosis of tumors. For example, antibodies directed against the proteins products of genes amplified in tumor cells can be used as tumor diagnostics or prognostics.

For example, antibodies, including antibody fragments, can be used to qualitatively or quantitatively detect the expression of proteins encoded by the amplified genes ("marker gene products"). The antibody preferably is equipped with a detectable, e.g. fluorescent label, and binding can be monitored by light microscopy, flow cytometry, fluorimetry, or other techniques known in the art. These techniques are particularly suitable, if the amplified gene encodes a cell surface protein, e.g. a growth factor. Such binding assays are performed essentially as described in section 5 above.

In situ detection of antibody binding to the marker gene products can be performed, for example, by immunofluorescence or immunoelectron microscopy. For this purpose, a histological specimen is removed from the patient, and a labeled antibody is applied to it, preferably by overlaying the antibody on a biological sample. This procedure also allows for determining the distribution of the marker gene product in the tissue examined. It will be apparent for those skilled in the art that a wide variety of histological methods are readily available for in situ detection.

R. Pharmaceutical Compositions

Antibodies specifically binding the product of an amplified gene identified herein, as well as other molecules identified by the screening assays disclosed hereinbefore, can be administered for the treatment of tumors, including cancers, in the form of pharmaceutical compositions.

If the protein encoded by the amplified gene is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment which specifically binds to the binding domain of the target protein is preferred. For example, based upon the variable region sequences of an antibody, peptide molecules can be designed which retain the ability to bind the target protein sequence. Such peptides can be synthesized chemically and/or produced by recombinant DNA technology (see, e.g. Marasco et al., *Proc. Natl. Acad Sci. USA* 90: 7889–7893 [1993]).

Therapeutic formulations of the antibody are prepared for storage by mixing the antibody having the desired degree of purity with optional pharmaceutically acceptable carriers, excipients or stabilizers (*Remington's Pharmaceutical Sciences* 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as giycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Non-antibody compounds identified by the screening assays of the present invention can be formulated in an analogous manner, using standard techniques well known in the art.

The formulation herein may also contain more than one active compound as necessary for the particular indication being treated, preferably those with complementary activities that do not adversely affect each other. Alternatively, or in addition, the composition may comprise a cytotoxic agent, cytokine or growth inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S-S bond formation through thio-disulfide interchange, stabilization may be achieved by modifyig sulfhydryl residues, lyophikiing from acidic solutions, controlling moisture content, using appropriate additives, and developing specific polymer matrix compositions.

S. Methods of Treatment

It is contemplated that the antibodies and other anti-tumor compounds of the present invention may be used to treat various conditions, including those characterized by overexpression and/or activation of the amplified genes identified herein. Exemplary conditions or disorders to be treated with such antibodies and other compounds, including, but not limited to, small organic and inorganic molecules, peptides, antisense molecules, etc. include benign or malignant tumors (e.g. renal, liver, kidney, bladder, breast, gastric, ovarian, colorectal, prostate, pancreatic, ling, vulval, thyroid, hepatic carcinomas; sarcomas; glioblastomas; and various bead and neck tumors); leukemias and lymphoid malignancies; other disorders such as neuronal, glial, astrocytal, hypothalamic and other glandular, macrophagal, epithelial, stromal and blastocoelic disorders; and inflammatory, angiogenic and immunologic disorders.

The anti-tumor agents of the present invention, e.g. antibodies, are administered to a mammal, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Intravenous administration of the antibody is preferred.

Other therapeutic regimens may be combined with the administration of the anti-cancer agents, e.g. antibodies of the instant invention. For example, the patient to be treated with such anti-cancer agents may also receive radiation therapy. Alternatively, or in addition, a chemotherapeutic agent may be administered to the patient. Preparation and dosing schedules for such chemotherapeutic agents may be used according to manufacturers' instructions or as determined empirically by the skilled practitioner. Preparation and dosing schedules for such chemotherapy are also described in *Chemotherapy Service Ed.*, M. C. Perry, Williams & Wilkins, Baltimore, Md. (1992). The chemotherapeutic agent may precede, or follow administration of the anti-tumor agent, e.g. antibody, or may be given simultaneously therewith. The antibody may be combined with an anti-oestrogen compound such as tamoxifen or an anti-progesterone such as onapristone (see, EP 616812) in dosages known for such molecules.

It may be desirable to also administer antibodies against other tumor associated antigens, such as antibodies which bind to the ErbB2, EGFR, ErbB3, ErbB4, or vascular endothelial factor (VEGF). Alternatively, or in addition, two or more antibodies binding the same or two or more different antigens disclosed herein may be co-administered to the patient. Sometimes, it may be beneficial to also administer one or more cytokines to the patient. In a preferred embodiment, the antibodies herein are co-administered with a growth inhibitory agent. For example, the growth inhibitory agent may be administered first, followed by an antibody of the present invention. However, simultaneous administration or administration of the antibody of the present invention first is also contemplated. Suitable dosages for the growth inhibitory agent are those presently used and may be lowered due to the combined action (synergy) of the growth inhibitory agent and the antibody herein.

For the prevention or treatment of disease, the appropriate dosage of an anti-tumor agent, e.g. an antibody herein will depend on the type of disease to be treated, as defined above, the severity and course of the disease, whether the agent is administered for preventive or therapeutic purposes, previous therapy, the patient's clinical history and response to the agent, and the discretion of the attending physician. The agent is suitably administered to the patient at one time or over a series of treatments.

For example, depending on the type and severity of the disease, about 1 μg/kg to 15 mg/kg (e.g. 0.1–20 mg/kg) of antibody is an initial candidate dosage for administration to the patient, whether, for example, by one or more separate administrations, or by continuous infusion, A typical daily dosage might range from about 1 μg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

T. Articles of Manufacture

In another embodiment of the invention, an article of manufacture containing materials useful for the diagnosis or treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for diagnosing or treating the condition and may have a sterile access port (for example the container may be an intravenous solution bag or a vial having a stopper pierceable by a hypodermic injection needle). The active agent in the composition is usually an anti-tumor agent capable of interfering with the activity of a gene product identified herein, e.g. an antibody. The label on, or associated with, the container indicates that the composition is used for diagnosing or treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Rockville, Md.

Example 1

Isolation of cDNA clones Encoding Human PRO201, PRO308 OR PRO309

An expressed sequence tag (EST) DNA database (LIFESEQ™, Incyte Pharmaceuticals, Palo Alto, Calif.) was searched and an EST was identified (1328938, DNA28710, FIG. 4A)(SEQ ID NO:13) which was in a fetal pancreas library which shared significant identity which the adaptor protein Shc. A full length cDNA corresponding to the isolated EST was cloned from a human fetal kidney library using an in vivo cloning technique (DNA30676, Nsp1)(SEQ ID NO:1) in pRK5. There is a single long open reading frame which encodes a 576 amino acid protein. Nsp1 (SEQ ID NO:1) also is related to Sck and Shc (FIG. 8)(SEQ ID NO:s 17 & 16, respectively), which is apparent in the SH2 region that appears at the N-terminus of Nsp1 (SEQ ID NO:1). Nsp1 (SEQ ID NO:1) also contains a proline-serine rich domain (PS) in the middle of the protein that may function as an SH3 interaction domain. The C-terminus of Nsp1 has no significant identity to any known mammalian proteins. This C-terminal sequence was then used to rescreen the EST database, wherein was found two additional fragments (104191)(DNA38653)(FIG. 4B)(SEQ ID NO:14) and (1651811)(DNA38654)(FIG. 4C)(SEQ ID NO:15). From these sequences were constructed cloning and enrichment primers, and the corresponding fulls length sequences were isolated for Nsp2 (SEQ ID NO:3) and Nsp3 (SEQ ID NO:5), respectively, using an in vivo cloning technique from a human placenta library in pRK5. The probes used for the cloning of the full length sequences were the lowing:

Nsp1 (SEQ ID NO:1):

Cloning: ACTGAGGCCTGTTGAAAGTGCAGAGCT-CAG (SEQ ID NO:7)

Enrichment Primer: GCTGAAGAAGAGCTTCAG (SEQ ID NO:8)

Nsp2 (SEQ ID NO:3):

Cloning: CAATGCCGATGGCCATTGTGTTGT-GTCTTTCAATTATGTCCAGGCGCA (SEQ ID NO:9)

Enrichment Primer: ATCCCAGAATGTCCACTG (SEQ ID NO:10)

Nsp3 (SEQ ID NO:5):

Cloning: GGCCAGCATGATGGACATGGTGTG-GAACCTTTCCAGCAGGTCTAGGCGTA (SEQ ID NO:11)

Enrichment Primer: GGTGCAGCCCAGGATGTC (SEQ ID NO:12)

The three proteins (Nsp1, Nsp2, Nsp3)(SEQ ID NO:s 1, 3 & 5) share an overall identity of between 33% and 47% (FIG. 6B). Nsp3 has an SH2 domain and a potential SH3 interaction domain (PS region). Nsp2 lacks the SH2 domain but does have a potential SH3 interaction domain. The absence of the SH2 domain in Nsp2 raises the possibility that this protein could act as a dominant negative regulator of the other two Nsps. All three proteins lack apparent kinase or phosphatase domains.

cDNA clones Nsp1, Nsp2 and Nsp3 (SEQ ID NO:s 2, 4 & 6) were sequenced in their entirety. The entire nucleotide sequence of DNA30676, DNA40575 and DNA61601 is shown in FIG. 1 (SEQ ID NO: 2), FIG. 2 (SEQ ID NO: 4) and FIG. 3 (SEQ ID NO: 6), respectively. Clones DNA30676-1223, DNA40575-1223 and DNA61601-1223 have been deposited with ATCC and are assigned ATCC deposit numbers 209567, 209565 and 209713. Moreover, related clones DNA40556-1223 and DNA40554-1223 have also been deposited with the ATCC and are assigned ATCC deposit numbers 209566 and 2096564.

Example 2

Northern Blot Analysis

Expression of PRO201, PRO308 and PRO309 mRNA in human tissues was examined by northern blot analysis. Human RNA blots were hybridized to an $^{32}$P-endiabelled DNA probe complementary to the nucleotide encoding amino acids: (a) 90–102 in DNA30676; (b) 270–284 in DNA40575 or (c) 475–491 in DNA61601. Endocrine and fetal II (Clontech) were hybridized in ExpressHybo® hybridization solution (Clontech) in accordance with the manufacturer's instructions. Blots were incubated with the probes in hybridization buffer (5×SSPE; 2×Denhardt's solution; 100 mg/mL denatured sheared salmon sperm DNA; 50% formamide; 2% SDS) for 16 hours at 42° C. The blots were washed several times in 2×SSC; 0.05% SDS for 1 hour at room temperature, followed by a 30 minute wash in 0.1×SSC; 0.1% SDS at 50° C. The blots were developed after overnight exposure by phosphorimager analysis (Fuji).

Figure 9A:
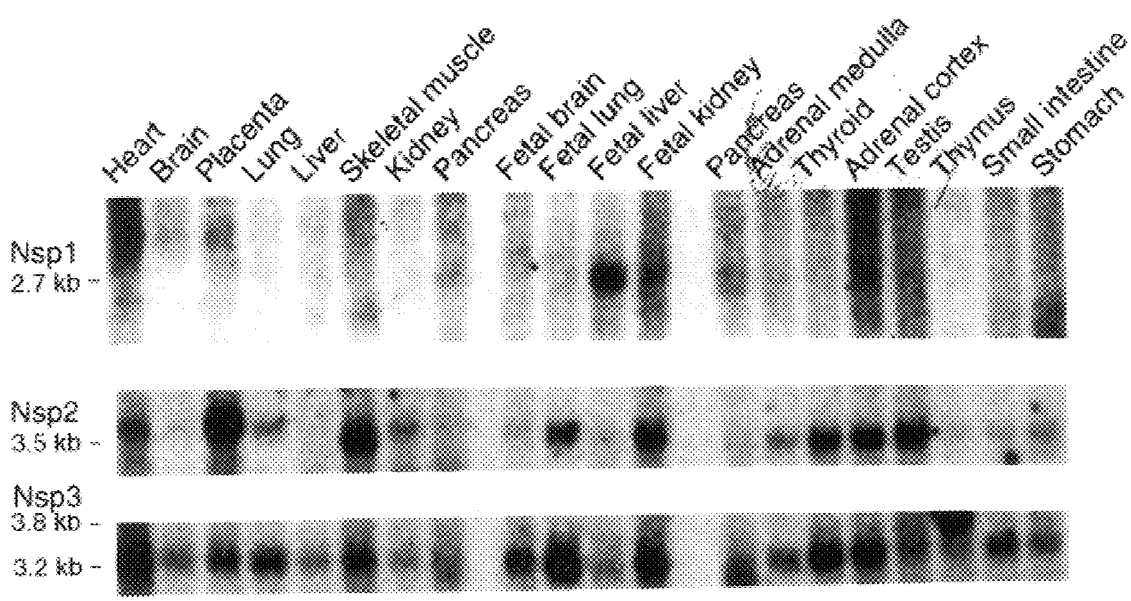
FIG. 9A is a northern blot showing significant expression of Nsp1 (SEQ ID NO:2) in human fetal liver, while Nsp2 (SEQ ID NO:4) and Nsp3 (SEQ ID NO:6) were more widely expressed.
Figure 9B:
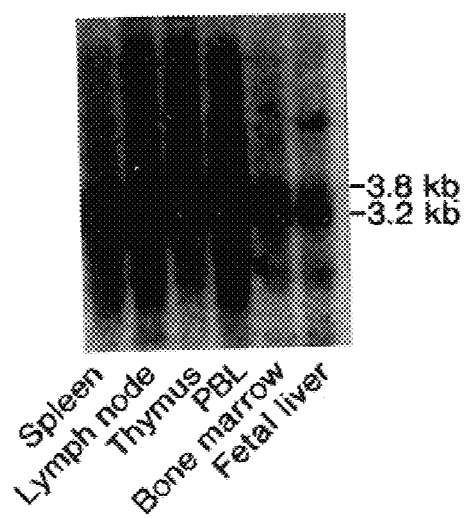
FIG. 9B shows the expression of two Nsp3 transcripts in hematopoietic tissues.

As shown in FIG. 9A, significant expression of Nsp1 (SEQ ID NO:2) was only detected in human fetal liver and may be expressed in other fetal tissues (e.g., fetal kidney). This pattern of expression suggests a role for Nsp1 in coordinating signaling pathways important for fetal development. In contrast, Nsp2 (SEQ ID NO:4) and Nsp3 (SEQ ID NO:6) were more widely expressed in many tissues. In hematopoietic tissues, two Nsp2 transcripts (3.8 Kb and 3.2 Kb) were detected (FIG. 9B).

Example 3

Figure 10A:
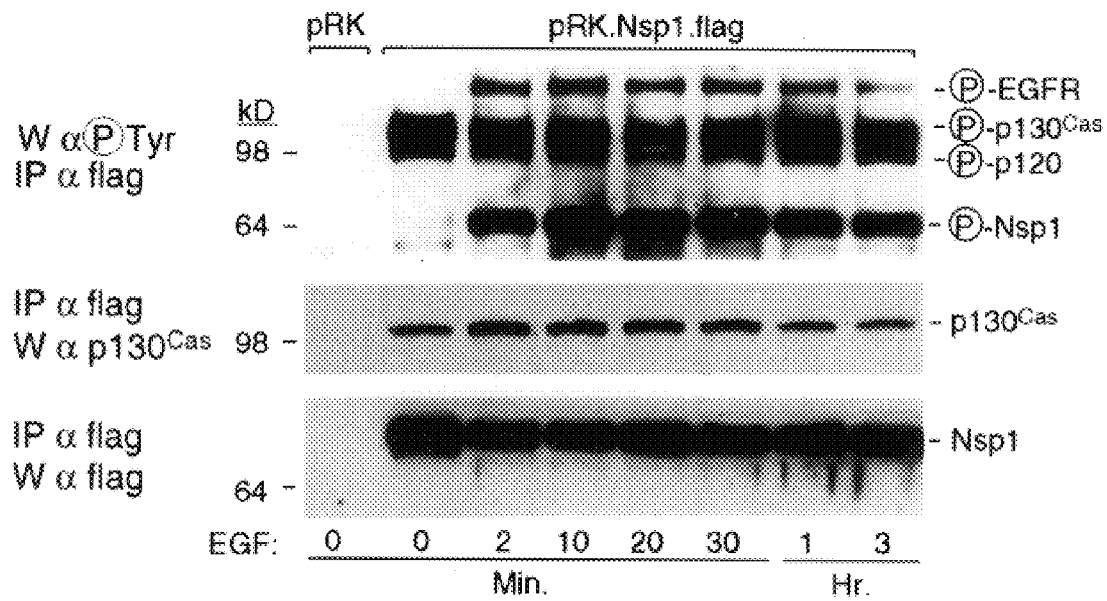
FIGS. 10A and 10C are western blots wherein anti-flag immunoprecipitates were blotted with anti-flag, anti-(P)Tyr or anti-Cas antibodies as indicated.
Figure 10B:
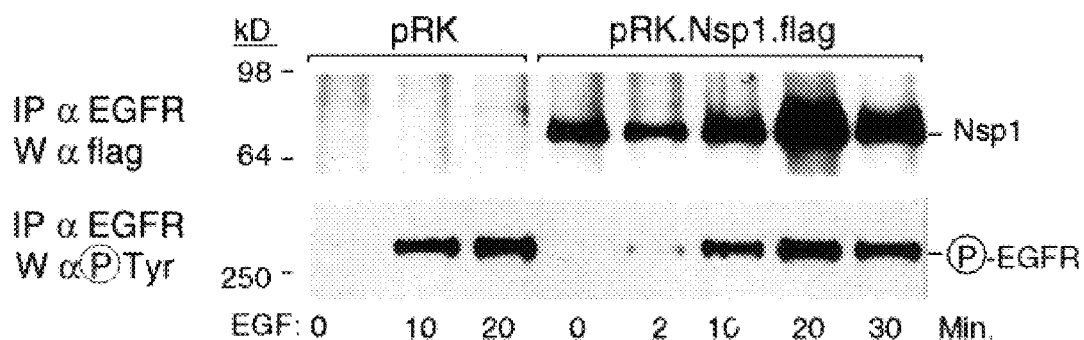
In FIG. 10B, anti-EGF receptor (CalBiochem) immunoprecipitates were blotted with anti-flag or aniti-(P)Tyr antibodies as indicated.
Figure 10C:
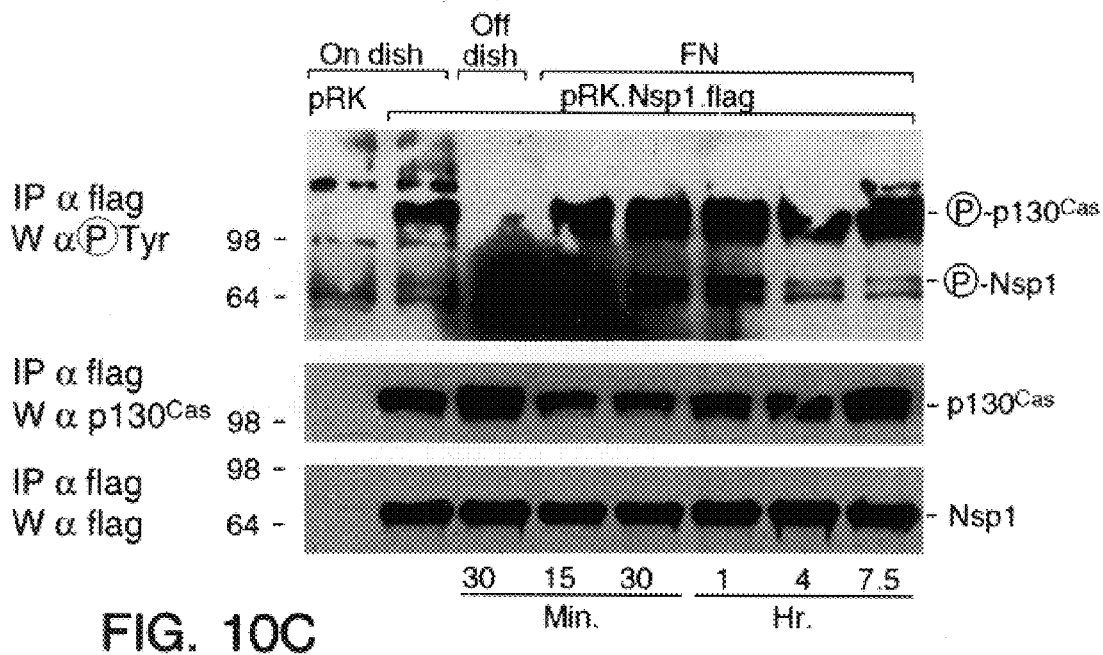

EGF, Insulin and Fibronectin Induced Nsp1 Phosphorylation and Complex Formation with p130$^{Cas}$ As Nsp1 has three potentially phosphoryvlatable tyrosines, a study was undertaken to determine whether Nsp1 could be phosphorylated in response to a variety of extracellular stimuli. Treatment with EGF induced a rapid tyrosine phosphorylation of Nsp1 I (SEQ ID NO:1) which occurred in 2 minutes or less (FIG. 10A). Nsp1 (SEQ ID NO:1) is also phosphorylated in response to insulin, IGF-1 and heregulin (not shown). In contrast, fibronectin (FN) stimulated only weak Nsp1 phosphorylation (FIG. 10C).

In order to trace the pathway(s) impacted by Nsp1 (SEQ ID NO:1). Applicants have identified proteins associated with Nsp1 (SEQ ID NO:1) in vivo by way of co-immunoprecipitation experiments. Treatment with EGF lead to an association between Nsp1 (SEQ ID NO:1) and a tyrosine phosphorylated protein with a molecular mass of approximately 170 kD. This protein is rapidly tyrosine phosphorylated in response to EGF and can be detected with a mAB directed against the EGF receptor. Further, Nsp1 (SEQ ID NO:1) can be detected by western blotting following immunoprecipitation of the EGF receptors (FIG. 10B). There is residual Nsp1 /EGF receptor interaction prior to EGF treatment, but the extent of the interaction significantly increases following exposure to EGF.

The coimmunoprecipitation experiments also revealed that Nsp1 interacts with a 130 kD protein (p130). In serum starved cells p130 was phosphorylated to a moderate level (FIG. 10A), whereas loss of cell attachment lead to a complete p130 dephosphorylation (FIG. 10C). By western blotting analysis this p130 was found to the adaptor protein $p130^{Cas}$. In FIG. 10A, anti-(P)Tyr antibody detected two bands atapproximately 130 kD, while anti-Cas antibody recognizes only the bottom band. We have not yet identified the upper band. Cas was originally found as a hyperphosphorylated protein following induced expression of viral Crk (v-Crk) [Sakai et al., *EMBO J*. 13: 3748–56 (1994)] and is phosphorylated in response to integrin interaction with extracellular matrix as well as a number of other stimuli. Chen et al., *J. Biol. Chem*. 272: 27401–10 (1997); Casamassima & Rozengurt, *J. Biol. Chem*. 272; 9363–70 (1997); Nojima et al., *J. Biol. Chem*. 270: 15398–402 (1995). Cas directly interacts with focal adhesion kinase (FAK)[Polte & Hanks, *Proc. Natl. Acad. Sci. USA* 92: 10678–82 (1995)] and appears to be a critical component by which extracellular events influence cell motility morphology and survival. Daniel & Reynolds, *Mol. Cell. Biol*. 15: 4819–24 (1995); Mo & Reynolds, *Cancer Res*. 56: 2633–40 (1996); Nakamaoto et al., *Mol. Cell. Biol*. 17: 3884–97 (1997).

The phosphorylation status of Nsp1 (SEQ ID NO:1) and Cas and the relative amount of Cas associated with Nsp1 (SEQ ID NO:1) is dependent on the signaling through either the EGF or integrin receptors. EGF increases Nsp1 phosphorylation but dephosphorylation of both total (data not shown) and Nsp1 (SEQ ID No.1) associated Cas (FIG. 10A). There is also an increase in the amount of Cas associated with Nspi after EGF treatment (FIG. 10A). In contrast, fibronectin had only a small effect on Nsp1 (SEQ ID NO:1) phosphorylation but increased the phosphorylation of Cas that is associated with Nsp1 and at the same time lead to a transient decrease in the amount of Cas that is associated with Nsp1 (FIG. 10C). An increase in Cas phosphorylation in response to integrins has been previously reported. Nojima et al., *J. Biol. Chem*. 270: 15398–402 (1995). This decrease in the Nsp1/Cas complex reached a nadir at approximately 30 minutes and then returned toward baseline conditions at around 4 hours.

Figure 11:
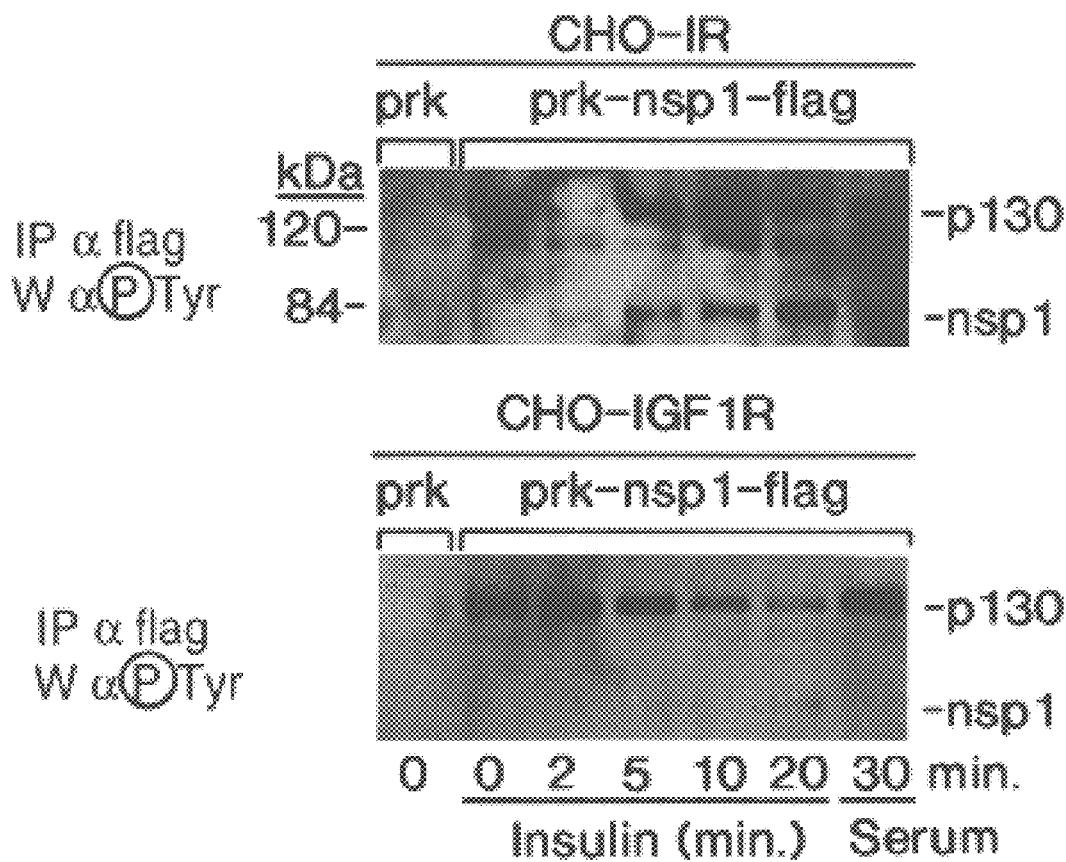
FIG. 11 is a western blot showing immunoprecipitates with anti-Flag or anti-p130$^{Cas}$ and blotting with anti-(P)Tyr Ab PY-20 or anti-p130$^{Cas}$.

In FIG. 11 it is demonstrated that insulin stimulated Nsp1 phosphorylation peaked at 2 hours, and then decreased after 14.5 hours. The same blot was reprobed with anti-FLAG antibody to show the equal loading. In FIG. 11 it is demonstrated that IGF-1 also stimulates the phosphorylation of Nsp1 although the level of phosphorylation in response to IGF-1 is less than that seen in response to insulin.

Figure 12A:
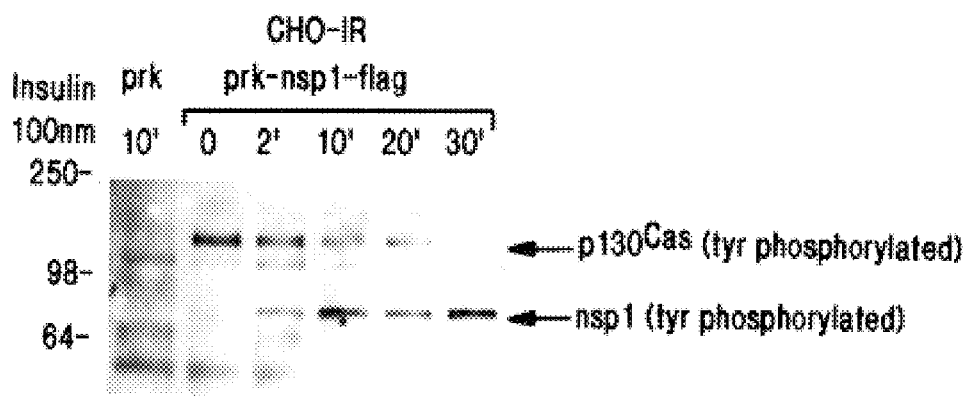
FIG. 12A is a western blot showing reduced phosphorylation of Nsp1 (SEQ ID NO:1) upon treatment with insulin.
Figure 12B:
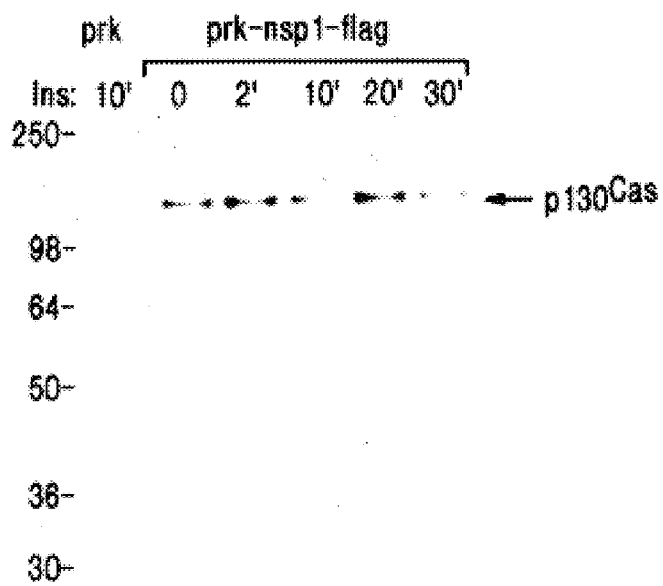
FIG. 12B is western blot created by stripping the blot in FIG. 12A which was reprobed with anti-p130$^{Cas}$ to confirm that the 130 kD protein was in fact p130$^{Cas}$.
Figure 13:
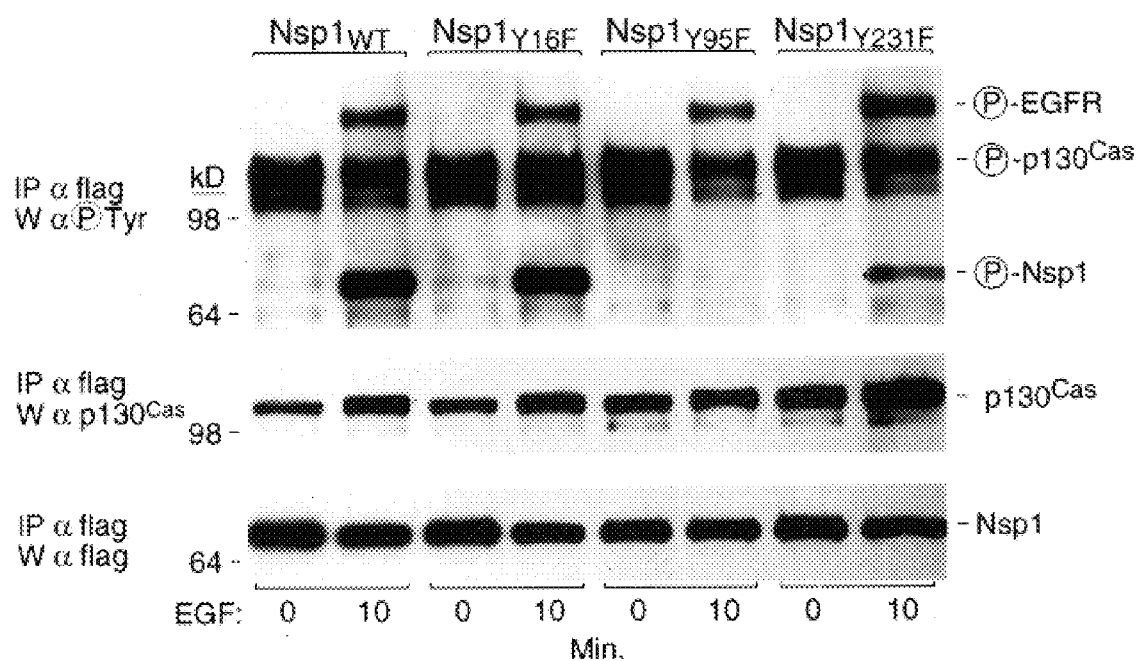
FIG. 13 is a western blot of various Nsp1 mutants which have been transfected into COS cells and treated with EGF, and the cell lysates immunoprecipitated with anti-flag Ab and Western blotted with either anti-(P)Tyr, anti-p130$^{Cas}$ or the anti-flag Ab.

IGF-1 Results:

In the absence of insulin (FIG. 13) or EGF (not shown) Nsp1 is associated with Cas. The phosphorylation of Cas was observed to decrease after insulin treatment. This is indicated both in FIG. 12 and FIG. 13A. The membrane of the tested samples in FIG. 13A was stripped and reprobed with anti-$p130^{Cas}$ antibody to also demonstrate that the amount of Cas associated with Nsp1 decreases following insulin treatment.

Materials and Methods:

EGF/fibronectin:

Transfected and serum starved COS (A,B) were either treated with 25 ng/ml EGF for the times indicated or left untreated. Transfected and serum starved 293 cells were either attached to plastic (on dish), held in suspension (off dish) or replated onto 10 mg/ml FN-coated dishes for the times indicated FIG. 10C(C). In FIGS. 10A and 10C antiflag immunoprecipitates were blotted with anti-flag, anti-(P) Tyr or anti-Cas antibodies as indicated. In FIG. 10B, anti-EGF receptor (CalBiochem) immunoprecipitates were blotted with anti-flag or anti-(P)Tyr antibodies as indicated. Transfected cells were lysed in coimmunoprecipitation assay (CoIPA) buffer (20 mM Tris, pH 7.5, 100 mM NaCl, 1% Triton X-100, 2 mM EDTA, 10 mM sodium pyrophosphate, 10 mM sodium fluoride, 2 mM orthovanadate) containing freshly added protease inhibitors (1 mM AEBSF, 10 mM leupeptin, 2 mg/ml aprotinin, 1 mM pepstatin). Anti-flag (Kodak, IBI immunoprecipitates and the associated proteins were visualized by anti-(P)Tyr antibody PY20 (Transduction Lab). The same blots were striped and reblotted with anti-$p130^{Cas}$ (Transduction Lab) or antiflag antibody and detected with the ECL system (Pierce). The Flap epitope (DYKDDDDK)(SEQ ID NO:19) was added in frame to the N-terminus of the Nsp1 cDNA construct using in vitro mutagenesis to create pRK.Nsp1.FLAG.

Insulin:

The FLAG epitope (DYKDDDDK)(SEQ ID NO:19) was inserted into the N-terminus of the Nsp1 cDNA construct using a standard in vitro mutagenesis to create pRK.Nsp-.FLAG. CHO cells overexpressing insulin receptor (CHO-IR) were cultured in F12-DMEM containing 10% serum, 2 mM L-glutamine, 100 units/ml penicillin, and 100 μg/ml streptomycin. Liposome-mediated transfection methods using DOSPER (Boehringer Mannheim) or superfect (Qiagen) were carried out on CHO cells in accordance with the manufacturers instructions. CHO-IR cells were transiently transfected with either the empty vector pRK or with pRK.Nsp1.FLAG and serum starved for 16 hours. Cells were treated with or without 100 nM insulin for different times and then lysed on ice for one hour in 1 ml of immunoprecipitation assay (IPA) buffer (10 mM Tris, pH7.5, 150 mM CaCl, 0.1% SDS, 1% Triton X-100, 1% deoxycholate, 5 mM EGTA, 10 mM sodium pyrophosphate, 10 mM sodium fluoride orthovanadate) containing fresh added protease inhibitors (1 mM AEBSF, 10 μM leupeptin, 2 μg/ml aprotinm, 1 μM pepstatin). Samples were unmunoprecipitated with an anti-FLAG affinity gel (IBI, Kodak). Following SDS-polyacrylamide gel electrophoresis, proteins were transferred onto nitrocellulose membrane (Novex), western blotted with the anti-phosphotyrosine antibody PY-20 (Transduction Lab) or anti-FLAG antibodies and detected with the ECL system (Pierce).

IGF-1 pRK or pRK.Nsp1.FLAG transfected with CHO-IR or CHO-IGF1R (IGF-1 receptor) cells were serum starved, treated with I100 nM insulin or 100 ng/ml IGF-1 and lysed in coimmunoprecipitation assay (ColPA) buffer (20 mM Tris, pH 7.5, 100 mM NaCl, 1% Triton X-100, 2 mM EDTA, 10 mM sodium pyrophosphate, 10 mM sodium fluoride, 2 mM orthovanadate) containing protease inhibitors. Samples were immunoprecipitated with anti-FLAG or anti-p130$^{Cas}$ and Western blotted with the anti-phosphotyrosine antibody PY-20 or anti-p130$^{Cas}$ (Santa Cruz Biotechnology).

Example 4

Mapping of Phosphorylated Tyrosine Residues in Nsp1

In order to map the phosphorylated residues in Nsp1, Applicants have independently changed each of the three tyrosine in Nsp1 (SEQ ID NO:1) to phenylalanine. Transfected cells were then stimulated with EGF and the Nsp1 (SEQ ID NO:1) immunoprecipitated. In all three cases the non-phosphorylated Nsp1 (SEQ ID NO:1) immunoprecipitated from non-stimulated cells was associated with both Cas and the EGF receptor. These results demonstrate that the amino acid changes were not grossly deleterious to the overall protein structure. While mutant $Nsp1_{Y61F}$ (SEQ ID NO:21) was phosphorylated normally in response to EGF, phosphorylation of $Nsp1_{Y95F}$ (SEQ ID NO:22) was not detected and $Nsp1_{Y231F}$ (SEQ ID NO:23) was weakly phosphorylated. This data suggests that there is first a phosphorylation of Y95 followed by the phosphoryiation of Y231. Y16 may or may not be phosphorylated, but is not required for phosphoryiation of either Y95 or Y231. Further, as the amount of EGF receptor coimmunoprecipitated with Nsp1 (SEQ ID NO:1) is increased by receptor phosphorylation but largely independent of Nsp1 (SEQ ID NO:1) phosphorylation, it would appear that Nsp1 (SEQ ID NO:1) association with Cas is independent of both Nsp1 (SEQ ID NO:1) and Cas phosphorylation status (FIG. 10), this interaction may be mediated through the SH3 domain of Cas and SH3 interaction domain of Nsp1 (SEQ ID NO:1).

Materials and Methods:

All three tyrosine residues in Nsp1 (SEQ ID NO:1) were changed to phenytalanine using a standard in vitro mutagenesis technique. Mutants (Y16F, Y95F and Y231F) (SEQ ID NO:s 21–23, respectively) and wild type Nsp1 (SEQ ID NO:1) DNAs were transfected into COS cells and treated with 25 ng/ml of EGF for 10 min. or left untreated. Cell lysates were immunoprecipitated with the anti-flag antibody and Western blotted with either the anti-P(Tyr) antibody, the anti-p130$^{Cas}$ antibody or the anti-flag antibody.

Example 5

Transformation and Tumorigenicity in Nude Mice

Introduction:

Since Cas has been implicated in c-src mediated events [Sakai et al., *EMBO J.* 13: 3748–56 (1994); Sakai et al., *Oncogene* 14: 1419–26 (1997)], Applicants examined the effect of Nsp1 (SEQ ID NO:1) in an NIH3T3transformation assay.

The NIH3T3 is a cell line which normally grow in monolayer even when the cells are overconfluent. They may be used to determine whether or not a candidate gene has the potential for oncogenicity when the candidate is transfected via retroviral mediated infection in vector MSCV. The transfected cells are allowed to generate into foci, picked and cultured to 10 million cells and injected into nude mice. It the transfected gene is oncogenic, it will grow on uninhibited by the deficient immune system of the nude mouse and form a tumor. See Winograd et al., In Vivo 1 (1): 1–13 (1987).

Figure 14A:
FIG. 14A is a micrograph of an ultrathin section of retroviral-infected vector MSCV NIH3T3 cells, while FIG. 14B show Nsp1 (SEQ ID NO:2) transfected NIH3T3 cells.

Discussion and Results:

More than one hundred foci of morphologically transformed cells were observed on one 100 mm plate of NIH3T3 cells following transfection with a retrovirus expressing Nsp1 and G418 selection, but none appeared in control (neo) vector. The transformed cells (FIG. 14B) were more rounded and compacted in comparison to the normal elongated fibroblast shape of the control transfected NIH3T3 cells (FIG. 14A). To investigate whether the transformed Nsp1 expressing cells were also tumorigenic, three independent foci were picked and expanded to generate NIH3T3-MSCV.Nsp1-.sub1, -.sub2 and -.sub3. Controls consisted of cell lines expressing neo only (NIH3T3-neo) and a pool of transfected cells that expressed lower levels of Nsp1 (SEQ ID NO:2) but was not transformed (NIH3T3-Nsp1.non-trans). The Nsp1 (SEQ ID NO:2) expressing, non-transformed cells were derived by infecting NIH3T3 cells with the Nsp1 (SEQ ID NO:2) expressing retroviral vector. These bulk cultures were selected for neomycin resistance, but were not allowed to proceed through the postconfluent growth that selects for foci formation.

Figure 14B:
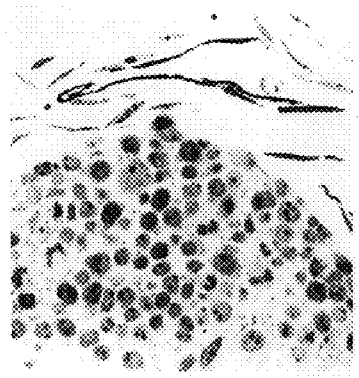
FIG. 14C is a micrograph of an ultrathin section of four week tumors which were fixed, blocked and sections stained with hematoxylin and eosin.
Figure 14C:
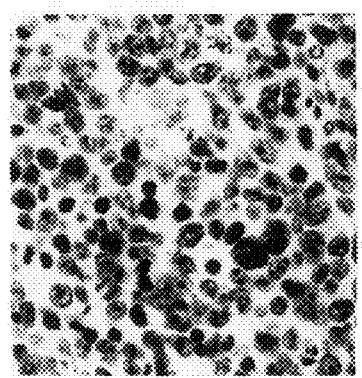

Each cell line was injected into five mice. No tumor growth was observed in any mice injected with neo control cells or NIH3T3-Nsp1.non-trans. cells. All five mice in each group injected with NIH3T3-MSCV.Nsp1-.sub1, -.sub2, -.sub3 grew obvious tumors within three weeks. Histological analysis indicated that the tumors consisted of large, irregular, moderately anaplastic epithelioid cells with a high mitotic index (FIG. 14C). There was no evidence of metastasis.

The tumors which formed were well circumscribed, locally expansile masses composed primarily of larger, irregular, moderately anaplastic epithelioid cells with a high mitotic index, interspersed, peripherally by small areas of spindle-cell proliferation. (FIG. 14C).

Materials and Methods:

pRK.Nsp1.FLAG plasmid was digested with EcoRI and Sal I. The Nsp1 cDNA fragment including the FLAG epitope was purified and subcloned into the EcoRI and Xho I sites of the retrovirat vector MSCVneo resulting in MSCVneo.Nsp1.FLAG. Mouse embryonic fibroblast cells (ATCC) and retroviral producer BOSC 23 cells were maintained in DMEM with 10% fetal bovine serum, 2 mM L-glutamine, 100 units/ml penicillin, and 100 µg/ml streptomycin.

The retroviral vectors MSCVneo and MSCVneo.Nsp1.FLAG were transfected into BOSC 23 cells using calcium phosphate-mediated transfection. The 72-hour supernatant was used to infect NIH3T3 cells plated on a 6-well plate. Infected cells were selected in 400 µg/ml G418 (Gibco) and pooled to generate NIH3T3-MSCV and -MSCV.Nsp1 cell lines. NIH3T3-MSCV and -MSCV.Nsp1 cells were grown until confluent for 4 days with a medium change once, split at a one to five ratio and grown until confluent for another 4 days. More than one hundred foci of morphologically transformed cells were observed on one 100 mm plate of NIH3T3 cells following infection, but none in the control (neo) vector. Foci were subjected to ultrathin section followed by Tutuidine blue staining. FIG. 14A shows ultrathin sections of either control cells (FIG. 14A), while FIG. 14B shows Nsp1 transformed foci.

Three transformed foci of NIH3T3-MSCV.Nsp1 were picked and expanded to generate sublines NIH3T3-MSCV.Nsp1-sc1, -sc2 and -sc3. $10^7$ vector transfected control cells, untransformed NIH3T3.MSCV.Nsp1 and three sublines were injected subcutaneously into the back of each nude mouse. Five mice were injected for each cell line. Tumor mass was measured at two weeks and four weeks. The resultant tumors (four weeks post injection) were fixed, blocked and sections stained with hematoxylin and cosin.

Figure 15:
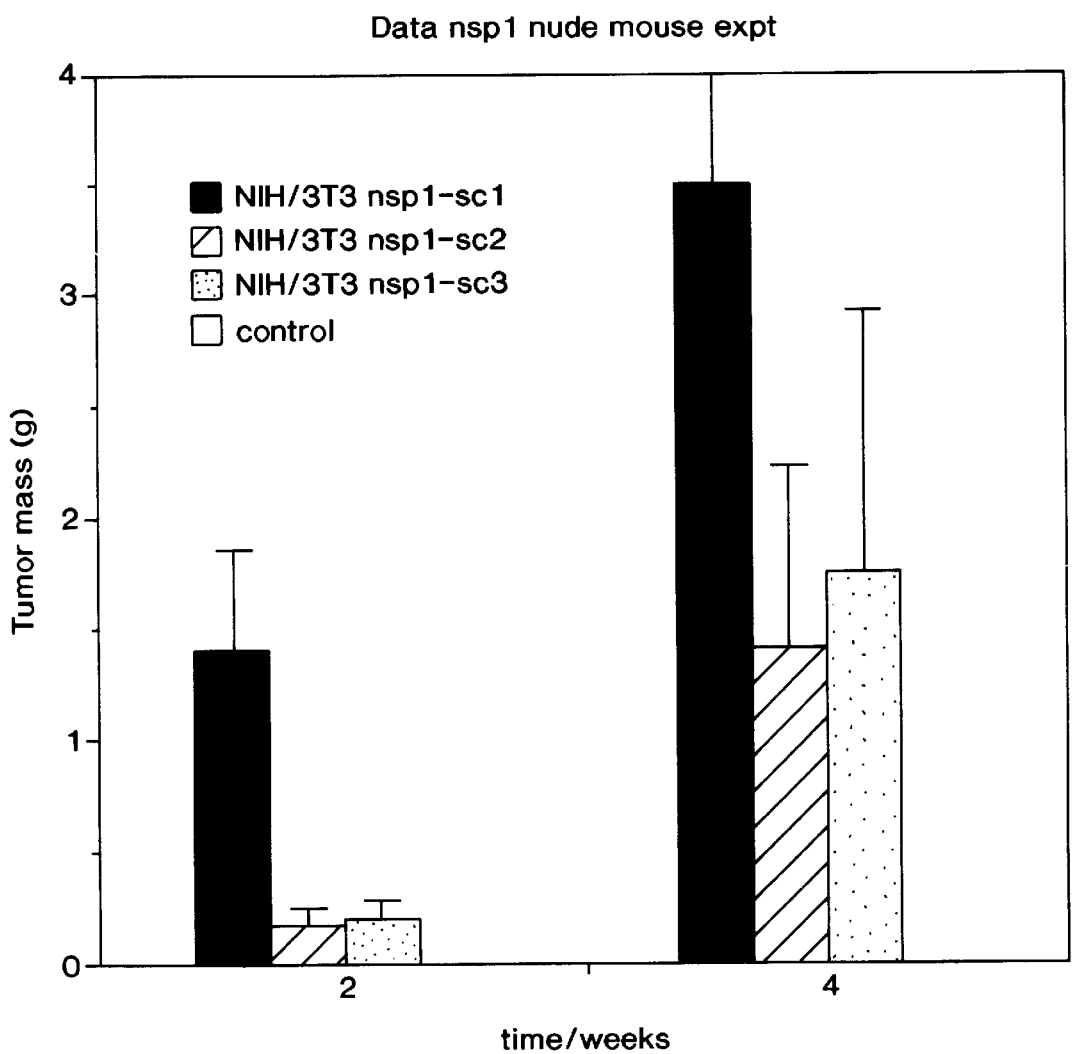
FIG. 15 is a bar graph of tumor size comparing vector control transfection and Nsp1.sc1, .sc2 and .sc3 cells.

(FIG. 14C). No tumor growth was observed in any mouse injected with vector transfected control cells or untransformed NIH3T3-MSCV.Nsp1 cells. Every mouse injected with NIH3T3-MSCV.Nsp1-.sc1, -.sc2 or -.sc3 grew tumors. (FIG. 15).

Example 6

Apoptosis Resistance

Figure 16:
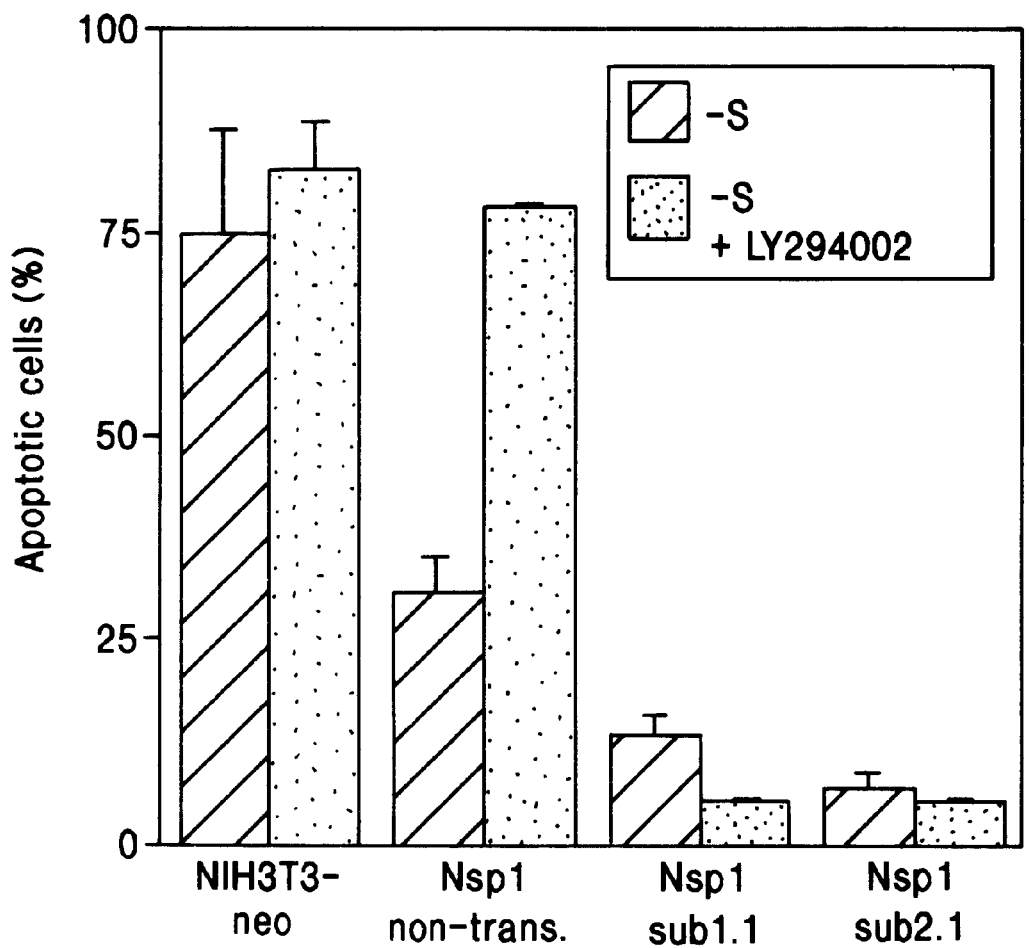
FIG. 16 is a bar graph of showing resistance to apoptosis of growth factor deprived NIH3T3 of transformed subclones Nsp.sub1.1, Nsp.sub.2.1, nontransformed cell culture (NIH3T3-Nsp1.non-trans) and the control cells NIH3T3-neo.
Figure 17:
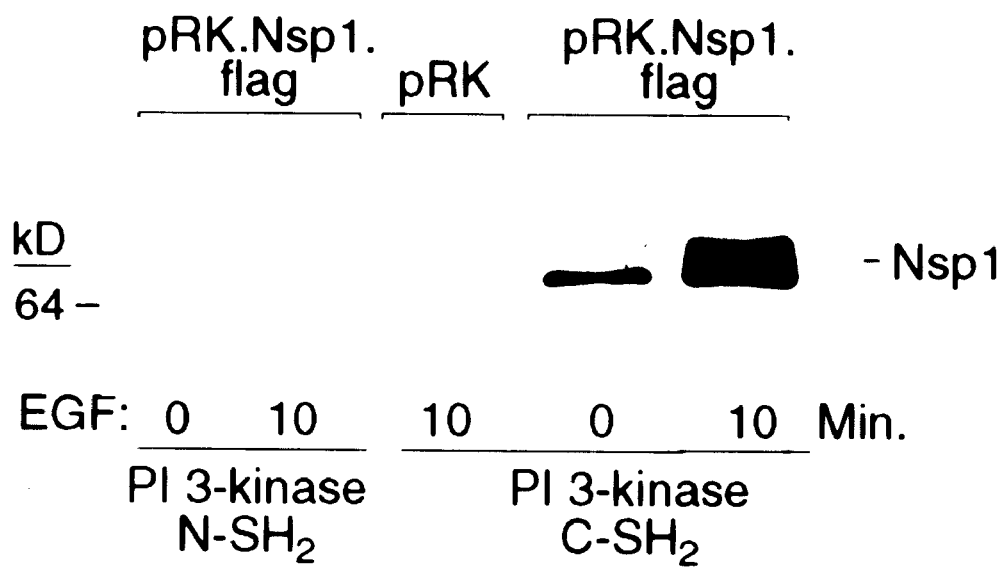
FIG. 17 is a western blot of COS cells transfected with pRK or Nsp1, treated with EDGF or no treatment, which were lysed in CoIP buffer and incubated with PI3-kinase N-terminal or C-terminal SH2 domain-GST beads (UBI). The precipitated Nsp1 was detected with anti-flag antibody.

Since the previous examples indicated that Nsp1 (SEQ ID NO:2) expression leads to NIH3T3 transformation and tumor formation, Applicants have investigated whether Nsp1 expression protects cells from apoptosis induced by removal of growth factors. Subcloned cell lines were derived from the morphologically transformed cells NIH3T3-MSCV.Nsp1-.sub1 and -.sub2 (designated Nsp1.-subl.1 and Nsp1.sub2.1). These transformed clonal lines, the non-transformed cell culture (NIH3T3-Nsp1.non-trans.) and the control cells NIH3T3-neo were serum starved for 48 hours in the presence or absence of the PI 3-kinase inhibitor LY294002 and subjected to ANNEXIN V (Clontech) apoptosis assay (FIG. 16). Although the NIH3T3-Nsp1.non-trans. cells were morphologically normal and did not form tumors in nude mice they were more resistant to apoptosis induced by growth factor withdrawal than were the control NIH3T3-neo cells. This small but significant increase in resistance to apoptosis was abolished by the P13 kinase inhibitor LY294002. In the vector control cells which do not express Nsp1 (SEQ ID NO:2), LY294002 did not by itself induce further apoptosis. In the Nsp1 (SEQ ID NO:2) transformed sublines, there was an almost complete protection from serum starvation induced apoptosis, but this effect was not sensitive to the treatment with the PI 3-kinase inhibitor. This dependent on PI 3-kinase at lower levels of Nsp1 (SEQ ID NO:1) would place PI 3-kinase downstream of Nsp1 (SEQ ID NO:1). in contrast the observation that the growth factor independence at high Nsp1 levels is not inhabitable by LY294002 suggests that Nsp1 (SEQ ID NO:1) impacts an additional pathway that functions independently of PI 3-kinase. That PI 3-kinase is both necessary and sufficient for growth factor mediated resistance to apoptosis had been previously reported. Kualik et al., *Mol. Cell Biol.* 17: 1595–606 (1997); Parrizas et al., *J. Biol. Chem.* 272: 154–61 (1997); Vemuri et al., *Development* 122: 2529–37 (1996).

Material and Methods:

Control cells (NIH3T3-neo), non-transformed Nsp1 (SEQ ID NO:2) expressing cells (NIH3T3-Nsp1.non-trans.) and the transformed subaies (Nsp1.sub.1.1 and Nsp1.sub2.1) were serum starved in the presence of absence of 10 μg/lm LY294002 for 48 hours. The percent of apoptotic cells were assayed using ANNEXIN V-FITC (Clontech) on FACS according to the manufacturers directions. Each cell line was assayed in triplicate and the means and standard deviations are shown. In transformed sublines, Nsp1 (SEQ ID NO:1) protected cells from serum starvation induced apoptosis.

Example 7

PI 3-Kinase Interaction

In order to determine whether Nsp1 (SEQ ID NO:1) does interact with PI 3-kinase, a GST fusion protein containing the PI 3-kinase N-terminal or C-terminal SH2 domains were incubated with EGF treated or untreated COS cell lysate transiently expressing Nsp1 (SEQ ID NO:2) or controls (FIG. 20). The C-terminal SH2 domain GST fusion protein does interact with Nsp1 (SEQ ID NO:1). This interaction appears to be at least partially dependent on the phosphorylation status of Nsp1 (SEQ ID NO:1) as there is an increase in the amount of Nsp1 (SEQ ID NO:1) that interacts with P13 kinase following EGF stimulation. The N-tertninal SH2 domain of PI3 kinase does not measureably interact with Nsp1 (SEQ ID NO:1).

Material and Methods:

COS cells transfected with pRK or with Nsp1 (SEQ ID NO:2) were treated with 25 ng/ml EGF or left untreated. Cells were lysed in ColP buffer (supra) and incubated with PI 3-kinase N-terminal or C-terminal SH2 domain-GST beads (UBI). The precipitated Nsp1 (SEQ ID NO:1) was detected with anti-flag antibody.

Example 8

Use of PRO201, PRO308 or PRO309 as a Hybridization Probe

The following method describes use of a nucleotide sequence encoding a PRO201, PRO308 or PRO309 polypeptide as a hybridization probe.

DNA comprising the coding sequence of a full-length or mature PRO201 (e.g., Nsp1), PRO308 (e.g., Nsp2) or PRO309 (e.g., Nsp3) and/or fragments thereof may be employed as a probe to screen for homologous DNAs (such as those encoding naturally-occurring variants of PRO201, PRO308 or PRO309 in human tissue EDNA libraries or human tissue genomic libraries.

Hybridization and washing of filters containing either library DNAs is performed under the following high stringency conditions. Hybridization of radiolabeted PRO201 (e.g., Nsp1), PRO308 (e.g., Nsp2) or PRO309 (e.g., Nsp3) -derived probe to the filters is performed in a solution of 50% formamide, 5xSSC, 0.1% sodium pyrophosphate, 50 mM sodium phosphate, pH 6.8, 2x Denhardt's solution, and 10% dextran sulfate at 42° C. for 20 hours. Washing of the filters is performed in anaqueous solution of 0.1xSSC and 0.1% SDS at 42° C.

DNAs having a desired sequence identity with the DNA encoding full-length native sequence PRO201, PRO308 or PRO309 can then be identified using standard techniques known in the art.

Example 9

Expression of PRO201, PRO308 or PRO309 in *E. coli*

This example illustrates preparation of an unglycosylated form of PRO201, PRO308 or PRO309 by recombinant expression in *E. coli*.

The DNA sequence encoding PRO201, PRO308 or PRO309 (SEQ ID NO:2, SEQ ID NO:4, SEQ ID NO: 6) is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., *Gene*, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the PRO201, PRO308 or PRO309 coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized PRO201, PRO308 or PRO309 protein can then be purified using a metal chelating column under conditions that allow tight binding of the protein.

Alternatively, expression in *E. coli* may be performed usually the following methology. The DNA sequence encoding PRO201 (e.g., Nsp1), PRO308 (e.g., Nsp2) or PRO309 (e.g., Nsp3) is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., *Gene*, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the PRO201, PRO308 or PRO309 coding region, lambda transcriptional terminator, and an argU gene.

The ligation mixture is then used to transform a selected *E. coli* strain using the methods described in Sambrook et al., suzpra. Transforinants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized PRO201, PRO308 or PRO309 protein can then be purified using a metal chelating column under conditions that allow tight binding of the protein.

Example 10

Expression of PRO201, PRO308 or PRO309 in Mammalian Cells

This example illustrates preparation of a glycosylated form of PRO201, PRO308 or PRO309 by recombinant expression in mammalian cells.

The vector, pRK5 (see EP 307,247, published March 15, 1989), is employed as the expression vector. Optionally, the PRO201, PRO308 or PRO309 DNA is ligated into pRK5 with selected restriction enzymes to allow insertion of the PRO201, PRO308 or PRO309 DNA using ligation methods such as described in Sambrook et al., supra. The resulting vector is called pRK5-PRO201, pRK5-PRO308 or pRK5-PRO309.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 $\mu$g pRK5-PRO201, pPK5-PRO308 or pRK5-PRO309 DNA is mixed with about 1 $\mu$g DNA encoding the VA RNA gene [Thimmappaya et al., *Cell*, 31:543 (1982)] and dissolved in 500 $\mu$l of 1 mM Tris-HCl, 0.1 mM EDTA, 0.227 M $CaCl_2$. To this mixture is added, dropwise, 500 $\mu$l of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 $\mu$Ci/ml $^{35}$S-cysteine and 200 $\mu$Ci/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of PRO201, PRO308 or PRO309 polypeptide. The cultures containing transfected cells may undergo further incubation (in serum free medium) and the medium is tested in selected bioassays.

In an alternative technique, PRO201, PRO308 or PRO309 may be introduced into 293 cells transiently using the dextran sulfate method described by Somparyrac et al., *Proc. Natl. Acad. Sci.*, 12:7575 (1981). 293 cells are grown to maximal density in a spinner flask and 700 $\mu$g pRK5-PRO201, pRK5-PRO308 or pRK5-PRO309 DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and reintroduced into the spinner flask containing tissue culture medium, 5:g/ml bovine insulin and 0.1:g/ml bovine transferrin. After about four days, the conditioned media is centrifuged and filtered to remove cells and debris. The sample containing expressed PRO201, PRO308 or PRO309 can then be concentrated and purified by any selected method, such as dialysis and/or column chromatography.

In another embodiment, PRO201, PRO308 or PRO309 can be expressed in CHO cells. The pRK5-PRO201, PRO308 or PRO309 can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of PRO201, PRO308 or PRO309 polypeptide, the culture medium may be replaced with serum free medium. Preferably, the cultures are incubated for about 6 days, and then the conditioned medium is harvested. The medium containing the expressed PRO201, PRO308 or PRO309 can then be concentrated and purified by any selected method.

Epitope-tagged PRO201, PRO308 or PRO309 may also be expressed in host CHO cells. The PRO201, PRO308 or PRO309 may be subcloned out of the pRK5 vector. The subclone insert can undergo PCR to fuse in frame with a selected epitope tag such as a poly-his tag into a Baculovirus expression vector. The poly-his tagged PRO201, PRO308 or PRO309 insert can then be subcloned into a SV40 driven vector containing a selection marker such as DHFR for selection of stable clones. Finally, the CHOD cells can be transfected (as described above) with the SV40 driven vector. Labeling may be performed, as described above, to verify expression. The culture medium containing the expressed poly-His tagged PRO201, PRO308 or PRO309 can then be concentrated and purified by any selected method, such as by $Ni^{2+}$-cholate affinity chromatography.

Example 11

Expression of PRO201, PRO308 or PRO309 in Yeast

The following method describes recombinant expression of PRO201, PRO308 or PRO309 in yeast.

First, yeast expression vectors are constructed for intracellular production or secretion of PRO201, PRO308 or PRO309 from the ADH2/GAPDH promoter. DNA encoding PRO201, PRO308 or PRO309, a selected signal peptide and the promoter is inserted into suitable restriction enzyme sites in the selected plasmid to direct intracellular expression of PRO201, PRO308 or PRO309. For secretion, DNA encoding PRO201, PRO308 or PRO309 can be cloned into the selected plasmid, together with DNA encoding the ADH2/GAPDH promoter, the yeast alpha-factor secretory signal/leader sequence, and linker sequences (if needed) for expression of PRO201, PRO308 or PRO309.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant PRO201, PRO308 or PRO309 can subsequently be isolated and purified by removing the yeast cells from the fermentation medium by centrifugation and then concentrating the medium using selected artridge filters. The concentrate containing PRO201, PRO308 or PRO309 may further be purified using selected column chromatography resins.

Example 12

Expression of PRO201, PRO308 or PRO309 in Baculovirus-Infected Insect Cells

The following method describes recombinant expression of PRO201, PRO308 or PRO309 in Baculovirus-infected insect cells.

The PRO201, PRO308 or PRO309 is fused upstream of an epitope tag contained with a baculovilus expression vector. Such epitope tags include poly-His tags and immunoglobulin tags (like Fc regions of IgG). A variety of plasmids may be employed, including plasmids derived from commercially available piasmids such as pVL1393 (Novagen). Briefly, the PRO201, PRO308 or PRO309 or the desired portion of the PR0201, PRO308 or PRO309 (such as the sequence encoding the extracellular domain of a transmembrane protein) is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus can be generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4–5 days of incubation at 28° C., the released viruses are harvested and used for further amplifications. Viral infection and protein expression may be performed as described by O'Reilley et al., *Baculovirus expression vectors: A Laboratory Manual*, Oxford: Oxford University Press (1994).

Following PCR amplification, the respective coding sequences are subcloned into a baculovirus expression vector (pb.PH.IgG for IgG fusions and pb.PH.His.c for poly-His tagged proteins), and the vector and Baculogold® baculovirus DNA (Pharmingen) were co-transfected into 105 *Spodloptera frugiperda* ("Sf9") cells (ATCC CRL 1711), using Lipofectin (Gibco BRL). pb.PH.IgG and pb.PH.His are modifications of the commercially available baculovirus expression vector pVL1393 (Pharrmingen), with modified polylinker regions to include the His or Fc tag sequences. The cells are grown in Hink's TNM-FH medium supplemented with 10% FBS (Hyclone). Cells are incubated for 5 days at 28° C. The supernatant is harvested and subsequently used for the first viral amplification by infecting Sf9 cells in Hink's TNM-FH medium supplemented with 10% FBS at an approximate multiplicity of infection (MOI) of 10. Cells are incubated for 3 days at 28° C. The supernatant is harvested and the expression of the constructs in the bacuiovirus expression vector determined by batch binding of 1 ml of supernatant to 25 mL of Ni-NTA beads (QIAGEN) for histidine tagged proteins or Protein-A Sepharose CL-4B beads (Pharmacia) for IgG tagged proteins followed by SDS-PAGE analysis comparing to a known concentration of protein standard by Coomassic blue staining.

The first viral amplification supernatant can be used to infect a spinner culture (500 ml) of Sf9 cells grown in ESF-921 medium (Expression Systems LLC) at an approximate MOI of 0.1. Cells were incubated for 3 days at 28° C. The supernatant was harvested and filtered. Batch binding and SDS-PAGE analysis is repeated, as necessary, until expression of the spinner culture is confirmed.

Expressed poly-his tagged PRO201, PRO308 or PRO309 can then be purified, for example, by $Ni^{2+}$-chelate affinity chromatography as follows. Extracts are prepared from recombinant virus-infected Sf9 cells as described by Rupert et al., *Nature*, 362:175–179 (1993). Briefly, Sf9 cells are washed, resuspended in sonication buffer (25 mL Hepes, pH 7.9; 12.5 mM $MgCl_2$; 0.1 mM EDTA 10% Glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% Glycerol, pH 7.8) and filtered through a 0.45 Fm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. Thre column is washed to baseline $A_{280}$ with loading buffer, at which point fraction collection is started. Next, the column is washed with a secondary wash buffer (50 mM phosphate; 300 mM NaCl, 10% Glycerol, pH 6.0), which elutes non-specifically bound protein. After reaching $A_{280}$ baseline again, the column is developed with a 0 to 500 mM Imidazole gradient in the secondary wash buffer. One mL fractions are collected anid analyzed by SDS-PAGE and silver staining or western blot with $Ni^{2+}$-NTA-conjugated to alkaline phosphatase (Qiagen). Fractions containing the eluted H isirtagged PRO201, PRO308 or PRO309 are pooled and dialyzed against loading buffer.

Alternatively, purification of the IgG tagged (or Fc tagged) PRO201, PRO308 or PRO309 can be performeod using kcnown chromatography techniques, including for instance, Protein A or protein G column chromatography.

Alternatively, a modified baculovinis procedure may be used incorporating high 5 cells. In this procedure, the DNA encoding the desired sequence was amplified with suitable systems, such as. Pfu (Stratagene), or fused upstream (5'-of) of an epitope tag contained with a baculovirus expression vector. Such epitope tags include poly-his tags and immunoglobulin tags (like Fc regions of IgG). A variety of plasmids may be employed, including plasmids derived from commercially available plasmids such as pIe-1 (Novagen). The pIE-1-1 and pIE1-2 vectors are designed for constitutive expression of recombinant proteins from the baculovirus ie 1 promoter in stably-transformed insect cells (1). The plasmids differ only in the orientation of the multiple cloning sites and contain all the hr5 enhancer element. pIE1-1 and pIE1-2 include the ie translation initiation site and can be used to produce fusion proteins. Briefly, the desired sequence or the desired portion of the sequence (such as the sequence encoding the extracellular domain of a transmembrane protein) is amplified by PCR with primers complementary to the 5' and 3' regions. The 5' primer may incorporate flanking (selected) restriction enzyme sites. The product was then digested with those selected restriction enzymes and subcloned into the expression vector. For example, derivatives of pIE1-1 can include the Fc region of human IgG (pb.PH.IgG) or an 8 histidine (pb.PH.His) tag downstream (3'-of) the desired sequence. Preferably, the vector construct is sequenced for confirmation.

Hi5 cells are grown to a confluency of 50% under the conditions of, 27° C., no $CO_2$, NO pen/strep. For each 150 mm plate, 30 µg of pIE based vector containing the sequence was mixed with 1 ml Ex-Cell medium (Media: Ex-Cell 401+1/100 L-Glu JRH Biosciences #14401-78P (note: this media is light sensitive)), and in a separate tube, 100 µl of CeliFectin (CeliFECTIN (GibcoBRL #10362-010) (vortexed to mix)) was mixed with 1 ml of Ex-Cell medium. The two solutions were combined and allowed to incubate at room temperature for 15 minutes. 8 ml of Ex-Cell media was added to the 2 ml of DNA/CellFECTIN mix and this is layered on Hi5 cells that have been washed once with Ex-Cell media. The plate is then incubated in darkness for 1 hour at room temperature. The DNA/CellFECTIN mix is then aspirated, and the cells arc washed once with Ex-Cell to remove excess CellFECTIN. 30 ml of fresh Ex-Cell media was added and the cells are incubated for 3 days at 28° C. The supernatant was harvested and the expression of the sequence in the baculovirus expression vector was determined by batch binding of 1 ml of supernatant to 25 mL of Ni-NTA beads (QIAGEN) for histidine tagged proteins or Protein-A Sepharose CL-4B beads (Pharmacia) for IgG tagged proteins followed by SDS-PAGE analysis comparing to a known concentration of protein standard by Coomassie blue staining.

The conditioned media from the transfected cells (0.5 to 3L) was harvested by centrifugation to remove the cells and filtered through 0.22 micron filters. For the poly-Hlis tagged constructs, the protein comprising the sequence is purified using a NI-NTA column (Qiagen). Before purification, imidazole is added to the conditioned media to a concentration of 5 mM. The conditioned media was pumped onto a 6 ml NI-NTA column equilibrated in 20 mM Hepes, pH 7.4, buffer containing 0.3M NaCl and 5 mM imidazoie at a flow rate of 4–5 ml/min. at 48° C. After loading, the column was washed with additional equilibration buffer and the protein fluted with equilibration buffer containing 0.25M imidazole. The highly purified protein was then subsequently desalted into a storage buffer containing 10 mM Hepes, 0.14M NaCl and 4% mannitol, pH 6.8, with a 25 ml G25 Superfine (Pharmacia) column and stored at −80° C.

Immunoadhesin (Fc containing) constructs of proteins are purified from the conditioned media as follows. The conditioned media is pumped onto a 5 ml Protein A column (Pharmacia) which has been previously equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 mL of 1M Tris buffer, pH 9. The highly purified protein is subsequently desalted into storage buffer as described above for the poly-His tagged proteins. The homogeneity of the sequence is assessed by SDS poiyacryiamide gels and by N-tertninal amino acid sequencing by Edman degradation and other analytical procedures as desired or necessary.

Example 13

Preparation of Antibodies that Bind PRO201, PRO308 or PRO309

This example illustrates preparation of monoclonal antibodies that can specifically bind PRO201, PRO308 or PRO309.

Techniques for producing the monoclonal antibodies are known in the art and are described, for instance, in Goding, supra. Immunogens that may be employed include purified PRO201, PRO308 or PRO309, fusion proteins containing PRO201, PRO308 or PRO309, and cells expressing recombinant PRO201, PRO308 or PRO309 on the cell surface. Selection of the immunoen can be made by the skilled artisan without undue experimentation.

Mice, such as Balb/c, are immunized with the PRO201, PRO308 or PRO309 immunogen emulsified in complete Freund's adjuvant and injected subcutaneously or intraperitoneally in an amount from 1–100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbitat bleeding for testing in ELISA assays to detect PRO201, PRO308 or PRO309 antibodies.

After a suitable antibody titer has been detected, the animals "positive" for antibodies can be injected with a final intravenous in jection of PRO201, PRO308 or PRO309. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against PRO201, PRO308 or PRO309. Determination of "positive" hybridoma cells secreting the desired monoclonal antibodies against PRO201, PRO308 or PRO309 is within the skill in the art.

The positive hybridoma cells can be injected intraperitoneally into syngeneic Balb/c mice to produce ascites containing the anti-PRO201, anti-PRO308 or anti-PRO309 nonoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 14

Gene Amplification

This example shows that the PRO201, PRO308 or PRO309-encoding genes are amplified in the genome of certain human lung, colon and/or breast cancers and/or cell lines. Amplification is associated with overexpression of the gene product, indicating that the binding specificities for at least two different antigens. In the present case, one of the binding specificities is for the PRO201, PRO308 or PRO309 proteins are useful targets for therapeutic intervention in certain cancers such as colon, lung, breast and other cancers. Therapeutic agent may take the form of antagonists of binding specificities for at least two different antigens. In the present case, one of the binding specificities is for the PRO201-, PRO308- or PRO309-encoding genes, for example, murine-human chimeric, humanized or human antibodies against a binding specificities for at least two different antigens. In the present case, one of the binding specificities is for the PRO201, PRO308 or PRO309 polypeptide.

The starting material for the screen was genomic DNA isolated from a variety cancers. The DNA is quantitated precisely, e.g. fluorometrically. As a negative control, DNA was isolated from the cells of ten normal healthy individuals which was pooled and used as assay controls for the gene copy in healthy individuals (not shown). The 5' nuclease assay (for example, TaqMan™) and real-time quantitative PCR (for example, ABI Prizm 7700 Sequence Detection System™ (Perkin Elmer, Applied Biosystems Division, Foster City, Calif.)), were used to find genes potentially amplified in certain cancers. The results were used to determine whether the DNA encoding binding specificities for at least two different antigens. In the present case, one of the binding specificities is for the PRO201, PRO308 or PRO309 is overrepresented in any of the primary lung or colon cancers or cancer cell lines or breast cancer cell lines that were screened. The primary lung cancers were obtained from individuals with tumors of the type and stage as indicated in Table 1. An explanation of the abbreviations used for the designation of the primary tumors listed in Table 1 and the primary tumors and cell lines referred to throughout this example has been given hereinbefore.

The results of the Taqman™ are reported in delta (Δ) CT units. One unit corresponds 1 PCR cycle or approximately a 2-fold amplification relative to nomal, two units corresponds to 4-fold, 3 units to 8-fold amplification and so on. Quantitation was obtained using primers and a Taqman™ fluorescent prove derived from the binding specificities for at least two different antigens. In the present case, one of the binding specificities is for the PRO201-, PRO308- and PRO309-encodingl gene. Regions of binding specificities for at least two different antigens. In the present case, one of the binding specificities is for the PRO201, PRO308 or PRO309 which are most likely to contain unique nucleic acid sequences and which are least likely to have spliced out introns are preferred for the primer and probe derivation, e.g. 3-untranslated region. The sequences for the primers and probes (forward, reverse and probe) used for the PRO201, PRO308 or PRO309 gene amplification were as follows:

PRO0201 (DNA30676):

30676.tm.f

5'-CGAGACACCCITCTTCACA-3' (SEQ ID NO:24)

30676.tm.r

5'-CGACTCCMTGGTCTCTTCTGG-3' (SEQ ID NO:25)

30676.tm.p

5'-CCGGGACCCCCAGGTTTTTGC-3' (SEQ ID NO:26)

DNA40556:

40556.tm.f:

5'-AGGGTCCTGCGTGGACTCT-3' (SEQ ID NO:27)

40556.tm.r:

5'-TCCTGTTCTTCCTCAATGGAGAC-3' (SEQ ID NO:28)

40556.tm.p:

5'-CCATCCCACCTG CTACATGCTCACC-3' (SEQ ID NO:29)

The 5' nuclease assay reaction is a fluorescent PCR-based technique which makes use of the 5' exonuclease activity of Taq DNA polymerase enzyme to monitor amplification in real time. Two oligonucteotide primers are used to generate an amplicon typical of a PCR reaction. A third oligonucieotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the TAQ DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

The 5' nuclease procedure is run on a real-time quantitative PCR device such as the ABI Prism 770TM Sequence Detection. The system consists of a thermocycler, laser, charge-coupled device (CCD) camera and computer. The system amplifies samples in a 96-well format on a thermocycler. During ampliflcation, laser-induced fluorescent signal is collected in real-time through fiber optics cables for all 96 wells, and detected at the CCD. The system includes software for running the instrument and for analyzing the data.

5' Nuclease assay data are initially expressed as Ct. or the threshold cycle. This is defined as the cycle at which the reporter signal accumulates above the background level of fluorescence. The ΔCt values are used as quantitative measurement of the relative number of starting copies of a particular target sequence in a nucleic acid sample when comparing cancer DNA results to normal human DNA results.

Table 1 describes the stage, T stage and N stage of various primary tumors which were used to screen the PR0201, PR0308 or PR0309 compounds of the invention.

second 4° C. centrifugation at 2500 rpm for 15 minutes. The nuclei were then resuspended into the residual buffer using 200 μl per tip. G2 buffer (10 ml) was added to the suspended nuclei while gentle vortexing was applied. Upon completion of buffer addition, vigorous vortexing was applied for 30 seconds. Quiagen protease (200 μl, prepared as indicated

TABLE 1

Primary Lung and Colon Tumor Profiles

| Primary Tumor | Stage | Other Stage | Dukes Stage | T Stage | N Stage |
|---|---|---|---|---|---|
| Human lung tumor SqCCA (SRCC724) [LT1] | IB | — | — | T1 | N1 |
| Human lung tumor NSCCa (SRCC725) [LT1a] | IA | — | — | T3 | N0 |
| Human lung tumor AdenoCa (SRCC726) [LT2] | IB | — | — | T2 | N0 |
| Human lung tumor AdenoCa (SRCC727) [LT3] | IB | — | — | T1 | N2 |
| Human lung tumor SqCCq (SRCC728) [LT4] | IIB | — | — | T2 | N0 |
| Human lung tumor AdenoCa (SRCC729) [LT6] | IV | — | — | T1 | N0 |
| Human lung tumor Adeno/SeCCa (SRCC730) [LT7] | IB | — | — | T1 | N0 |
| Human lung tumor AdenoCa (SRCC731) [LT9] | IIB | — | — | T2 | N0 |
| Human lung tumor SqCCa (SRCC732) [LT10] | IA | — | — | T3 | N1 |
| Human lung tumor AdenoCa (SRCC733) [LT11] | IB | — | — | T2 | N1 |
| Human lung tumor AdenoCa (SRCC734) [LT12] | IIA | — | — | T1 | N0 |
| Human lung tumor BAC (SRCC735) [LT13] | IB | — | — | T3 | N0 |
| Human lung tumor SqCCa (SRCC736) [LT15] | IB | — | — | T2 | N0 |
| Human lung tumor AdenoCa (SRCC737) [LT16] | IIB | — | — | T1 | N1 |
| Human lung tumor SqCCa (SRCC738) [LT17] | IIB | — | — | T2 | N1 |
| Human lung tumor SqCCa (SRCC739) [LT18] | IB | — | — | T2 | N0 |
| Human lung tumor SqCCa (SRCC740) [LT19] | IIB | — | — | T2 | N0 |
| Human lung tumor LCCa (SRCC741) [LT21] | IIB | — | — | T3 | N1 |
| Human colon AdenoCa (SRCC742) [CT2] | — | M1 | D | pT4 | N0 |
| Human colon AdenoCa (SRCC743) [CT3] | | — | B | pT4 | N0 |
| Human colon AdenoCa (SRCC744) [CT8] | | | B | T3 | N1 |
| Human colon AdenoCa (SRCC745) [CT10] | | | A | pT2 | N0 |
| Human colon AdenoCa (SRCC746) [CT12] | | M0, R1 | B | T3 | N0 |
| Human colon AdenoCa (SRCC747) [CT14] | | PM0, R0 | B | pT3 | pN0 |
| Human colon AdenoCa (SRCC748) [CT15] | | M1, R2 | D | T4 | N2 |
| Human colon AdenoCa (SRCC749) [CT16] | | PM0 | B | pT3 | pN1 |
| Human colon AdenoCa (SRCC750) [CT17] | | | Cl | pT3 | pN0 |
| Human colon AdenoCa (SRCC751) [CT1] | | M0, R1 | B | pT3 | N0 |
| Human colon AdenoCa (SRCC752) [CT4] | | | B | pT3 | M0 |
| Human colon AdenoCa (SRCC753) [CT5] | | G2 | Cl | pT3 | pN0 |
| Human colon AdenoCa (SRCC754) [CT6] | | | B | pT3 | pN0 |
| Human colon AdenoCa (SRCC755) [CT7] | | G1 | A | pT2 | pN0 |
| Human colon AdenoCa (SRCC756) [CT9] | | G3 | D | pT4 | pN0 |
| Human colon AdenoCa (SRCC757) [CT11] | | | B | T3 | pN0 |
| Human colon AdenoCa (SRCC758) [CT18] | | M0, R0 | B | pT3 | pN0 |

DNA Preparation:

DNA was prepared from cultured cell lines, primary tumors, normal human blood. The isolation was performed using purification kit, buffer set and proteae and all from Quiagen, according to the manufacturer's instructions and the description below.

Cell Culture Lysis:

Cells were washed and trypsinized at a concentration of 7.5×10⁸ per tip and pelleted by centrifuging at 1000 rpm for 5 minutes at 4° C., followed by washing again with ½ volume of PBS recentrifugation. The pellets were washed a third time, the suspended cells collected and washed 2× with PBS. The cells were then suspended into 10 mL PBS. Buffer C1 was equilibrated at 4° C. Quiagen protease #19155 was diluted into 6.25 ml cold ddH$_2$O to a final concentration of 20 mg/ml and equilibrated at 4° C. 10 mL of G2 Buffer was prepared by diiuting Quiagen RNAse A stock (100 mg/ml) to a final concentration of 200 μg/ml.

Buffer C1 (10 mL, 4° C.) and ddH2O (40 mL, 4° C.) were then added to the 10 mL of cell suspension, by inverting and incubated on ice for 10 minutes. The cell nuclei were pelleted by centrifuging in a Beckman swinging bucket rotor at 2500 rpm at 4° C. for 15 minutes. The supernatant was discarded and the nuclei were suspended with a vortex into 2 mL Buffer C1 (at 4° C.) and 6 mL ddH$_2$O, followed by a above) was added and incubated at 50° C. for 60 minutes. The incubation and centrifugation was repeated until the lysates were clear (e.g., incubating additional 30–60 minutes, pelleting at 3000×g for 10 min., 4° C.).

Solid Human Tumor Sample Preparation and Lysis:

Tumor samples were weighed and placed into 50 ml conical tubes and held on ice. Processing was limited to no more than 250 mg tissue per preparation (1 tip/preparation). The protease solution was freshly prepared by diluting into 6.25 ml cold ddH$_2$O to a final concentration of 20 mg/ml and stored at 4° C. G2 buffer (20 ml) was prepared by diluting DNAse A to a final concentration of 200 mg/ml (from 100 mg/ml stock). The tumor tissue was homogenated in 19 ml G2 buffer for 60 seconds using the large tip of the polytron in a laminar-flow TC hood to order to avoid inhalation of aerosols, and held at room temperature. Between samples, the poiytron was cleaned by spinning at 2×30 seconds each in 2L ddH$_2$O, followed by G2 buffer (50 ml). If tissue was still present on the generator tip, the apparatus was disassembled and cleaned.

Quiagen protease (prepared as indicated above, 1.0 ml) was added, followed by vortexing and incubation at 50° C. for 3 hours. The incubation and centrifugation was repeated until the lysates were clear (e.g., incubating additional 30–60 minutes, pelleting at 3000×g for 10 min., 4° C.).

Human Blood Preparation and Lysis:

Blood was drawn from healthy volunteers using standard infectious agent protocols and citrated into 10 ml samples per tip. Quiagen protease was freshly prepared by dilution into 6.25 ml cold ddH$_2$O to a final concentration of 20 mg/ml and stored at 4° C. G2 buffer was prepared by diluting RNAse A to a final concentratio of 200 μg/ml from 100 mg/ml stock. The blood (10 ml) was placed into a 50 ml conical tube and 10 ml C1 buffer and 30 ml ddH$_2$O (both previously equilibrated to 4° C.) were added, and the components mixed by inverting and held on ice for 10 minutes. The nuclei were pelleted with a Beckman swinging bucket rotor at 2500 rpm, 40° C. for 15 minutes and the supernatant discarded. With a vortex, the nuclei were suspended into 2 ml C1 buffer (4° C.) and 6 ml ddH$_2$O (4° C.). Vortexing was repeated until the pellet was white. The nuclei were then suspended into the residual buffer using a 200 μl tip. G2 buffer (10 ml) were added to the suspended nuclei while gently vortexing, followed by vigorous vortexing for 30 seconds. Quiagen protease was added (200 μl) and incubated at 50° C. for 60 minutes. The incubation and centrifugation was repeated until the lysates were clear (e.g., incubating additional 30–60 minutes, pelleting at 3000×g for 10 min., 4° C.).

Purification of Cleared Lysates:

(I) Isolation of Genomic DNA:

Genomic DNA was equilibrated (1 sample per maxi tip preparation) with 10 ml QBT buffer. QF elution buffer was equilibrated at 50° C. The samples were vortexed for 30 seconds, then loaded onto equilibrated tips and drained by gravity. The tips were washed with 2×15 ml QC buffer. The DNA was eluted into 30 ml silanized, autoclaved 30 ml Corex tubes with 15 ml QF buffer (50° C.). Isopropanol (10.5 ml) was added to each sample, the tubes covered with parafin and mixed by repeated inversion until the DNA precipitated. Samples were pelleted by centriftigation in the SS-34 rotor at 15,000 rpm for 10 minutes at 4° C. The pellet location was marked, the supernatant discarded, and 10 ml 70% ethanol (4° C.) was added. Samples were pelleted again by centrifugation on the SS-34 rotor at 10,000 rpm for 10 minutes at 4° C. The pellet location was marked and the supernatant discarded. The tubes were then placed on their side in a drying rack and dried 10 minutes at 37° C., taking care not to overdry the samples.

After drying, the pellets were dissolved into 1.0 ml TE (pH 8.5) and placed at 50° C. for 1–2 hours. Samples were held overnight at 4° C. as dissolution continued. The DNA solution was then transferred to 1.5 ml tubes with a 26 gauge needle on a tuberculin syringe. The transfer was repeated 5× in order to shear the DNA. Samples were then placed at 50° C. for 1–2 hours.

(2) Quantitation of Genomic DNA and Preparation for Gene Amplification Assay:

The DNA levels in each tube were quantified by standard A260, A280 spectrophotometr on a 1:20 dilution (5 μl DNA+95 μl ddH$_2$O) using the 0.1 ml quartz cuvetts in the Beckman DU640 spectrophotometer. A260/A280 ratios were in the range of 1.8–1.9. Each DNA samples was then diluted further to approximately 200 ng/ml in TE (pH 8.5). If the original material was highly concentrated (about 700 ng/μl), the material was placed at 50° C. for several hours until resuspended.

Fluorometric DNA quantitation was then performed on the diluted material (20–600 ng/ml) using the manufacturer's guidelines as modified below. This was accomplished by allowing a Hoeffer DYNA Quant 200 fluorometer to warm-up for about 15 minutes. The Hoechst dye working solution (#H33258, 10 μl, prepared within 12 hours of use) was diluted into 100 ml 1×TNE buffer. A 2 ml cuvette was filled with the fluorometer solution, placed into the machine, and the machine was zeroed. PGEM 3Zf(+) (2 μl, lot #360851026) was added to 2 ml of fluorometer solution and calibrated at 200 units. An additional 2 μl of PGEM 3Zf(+) DNA was then tested and the reading confirmed at 400+/−10 units. Each sample was then read at least in triplicate. When 3 samples were found to be within 10% of each other, their average was taken and this value was used as the quantification value.

The fluorometricly determined concentration was then used to dilute each sample to 10 ng/μl in ddH$_2$O This was done simultaneously on all template samples for a single TaqMan plate assay, and with enough material to run 500–1000 assays. The samples were tested in triplicate with Taqman™ primers and probe both B-actin and GAPDH on a single plate with normal human DNA and no-template controls. The diluted samples were used provided that the CT value of normal human DNA subtracted from test DNA was +/−1 CT. The diluted, lot-qualified genomic DNA was stored in 1.0 ml aliquots at −80° C. Aliquots which were subsequently to be used in the gene amplification assay were stored at 4° C. Each 1 ml aliquot is enough for 8–9 plates or 64 tests.

Gene Amplification Assay:

The PRO201, PRO308 or PRO309 compounds of the invention were screened in the following primary tumors and the resulting ΔCt values are reported in Table 2.

TABLE 2

ΔCt values of DNA30676 (SEQ ID NO:2)
and DNA40556 (SEQ ID NO:20)
in selected primary lung and colon tumors and cell lines

| Primary Tumor or Cell Line | DNA30676 | DNA40556 |
| --- | --- | --- |
| LT1 | 0.27, 0.05, 0.41, −0.27 | 0.31, −0.14, 0.54 |
| LT1a | 1.15, 0.99, 1.37, 0.9 | 1.44, 0.6, 1.06 |
| LT2 | 0.22, 0.24, −0.1, 0.04 | 0.65, 0.33 |
| LT3 | 2.16, 1.89, 2.52, 1.63 | 1.21, 0.35, 0.26 |
| LT4 | 0.22, 0.03, 0.41, 0.16 | 1.38, 0.79 |
| LT6 | 1.66, 0.76, 0.82, −0.02 | 0.75, −0.02, 0.27 |
| LT7 | 1.01, 0.54, 0.69, −0.33 | 1.03, −0.08, 0.88 |
| LT8 | — | 1.14 |
| LT9 | 1.16, 0.74, 0.82, −0.02 | 1.32, 0.16, 0.40 |
| LT10 | 1.78, 0.72, 1.22, 0.6 | 1.0, 0.12, 0.40 |
| LT11 | 1.86, 1.42, 1.29 | 1.985, 0.67 |
| LT12 | 0.81, 0.69, 0.21 | 1.725, −0.49, 0.27 |
| LT13 | 2.71, 2.24, 1.45 | 1.485, 0.51, 1.035 |
| LT15 | 2.89, 2.79, 2.07 | 1.965, 0.58, 0.975 |
| LT16 | 1.13, 0.4, 1.78 | 0.775, 0.33, 0.595 |
| LT17 | 2.11, 1.55, 1.23 | 1.965, 0.04 |
| LT18 | 0.22, −0.08, 1.72 | 0.345, −0.07 |
| LT19 | 3.51, 3.23 | 1.425 |
| LT21 | 1.9, 0.7 | 1.085 |
| LT22 | −0.13 | −2.65 |
| CT2 | 3.81 | 0.385, 0.865 |
| CT3 | 2.3 | 0.545, 0.315 |
| CT8 | 1.97 | 0.695, 0.305 |
| CT10 | 3.01 | 1.135, 0.845 |
| CT12 | 2.76 | 0.925, 0.675 |
| CT14 | 3.34 | 1.245, 0.995 |
| CT15 | 2.58 | 0.895 |
| CT16 | 2.46 | 0.755, 0.635 |
| CT17 | 2.64 | 0.565, 0.425 |
| CT1 | 1.57 | 0.875, 0.865 |
| CT4 | 3.39 | 0.585, 0.585 |
| CT5 | 2.95 | 1.005 |
| CT6 | 2.81 | 0.995 |
| CT7 | 2.77 | 0.795 |
| CT9 | 2.63 | 0.575, 0.805 |
| CT11 | 3 | 1.135 |

TABLE 2-continued

ΔCt values of DNA30676 (SEQ ID NO:2)
and DNA40556 (SEQ ID NO:20)
in selected primary lung and colon tumors and cell lines

| Primary Tumor or Cell Line | DNA30676 | DNA40556 |
|---|---|---|
| CT18 | 2.23 | 0.755 |
| A549 | — | 1.255 |
| Calu-1 | 2.37 | — |
| Calu-6 | 2.61 | — |
| H157 | 2.39 | — |
| H441 | 2.07 | — |
| H460 | 0.28 | — |
| SKMES1 | 3.01 | — |
| H522 | 2.91 | — |
| H810 | 2.07 | — |
| SW620 | 0.69 | — |
| Colo320 | 1.95 | 0.685 |
| HT29 | 0.37 | — |
| SKCO1 | 0.3 | — |
| SW403 | 0.59 | — |
| LS174T | 0.38 | — |
| Colo-205 | 1.26 | — |
| HCT15 | 0.61 | — |
| HCT116 | — | 0.935 |
| HCC2998 | 0.27 | — |
| KM12 | 0.82 | — |

Figure 18:
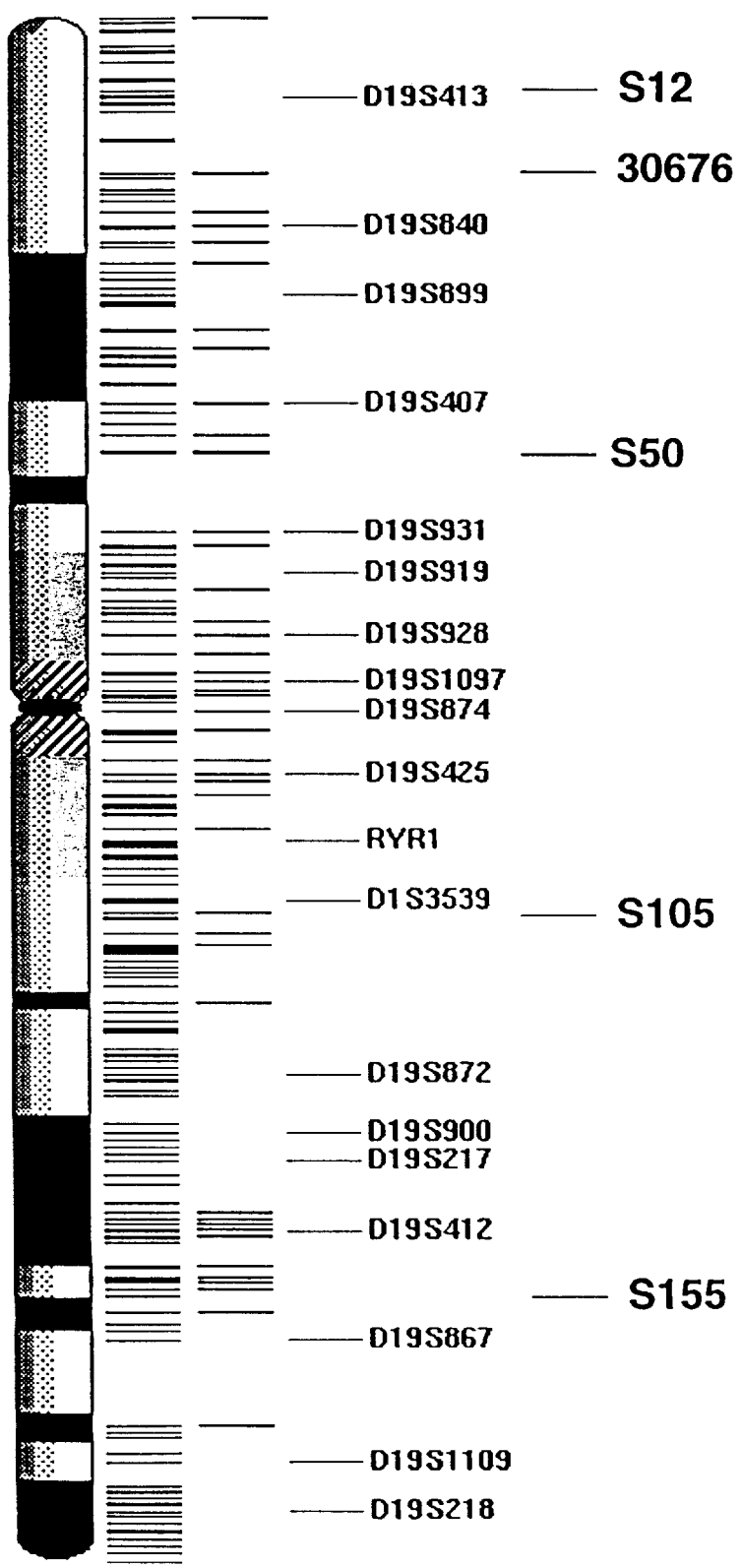
FIG. 18 is a pictoral representation of chromosome 19 depicting the rough approximation of the mapping of DNA30676 (SEQ ID NO:2) in the human genome.

DNA30676 (SEQ ID NO:2) was also reexamined along with selected tumors from the above initial screen with framework mapping,. FIG. 18 and Table 3 indicate the chromosomal mapping of the framework markers that were used in the present example. The framework markers are located approximately every 20 megabases and were used to control aneuploidy.

DNA30676 (SEQ ID NO:2) was also reexamined with epicenter mapping. The markers indicated in Tables 4 are located in close proximity (in the genome) to DNA30676 (SEQ ID NO:2) and are used to assess the relative amplification in the immediate vicinity of Chromosome 19 wherein the respective molecule is located. The distance between individual markers is measured in centirays (cR), which is a radiation breakage unit approximately equal to a 1% chance of a breakage between two markers. One cR is very roughly equivalent to 20 kilobases. The marker SHGC-35441 is the marker found to be the closest to the location on chromosome 19 where DNA30676 maps.

TABLE 3

Framework Markers Along Chromosome 19

| Map Position on Chromosome 19 | Stanford Human Genome Center Marker Name |
|---|---|
| S12 | AFMa107xc9 |
| S50 | SHGC-31335 |
| S105 | SHGC-34102 |
| S155 | SHGC-16175 |

TABLE 4

Epicenter Markers Along Chromosome 19 used for DNA30676

| Map Position on Chromosome 19 | Stanford Human Genome Center Marker Name | Distance to next Marker (cR) |
|---|---|---|
| S12 | AFMa107xc9 | 22 |
| S16 | SHGC-1261 | 53 |
| S17 | SHGC-2897 | 7 |
| S18 | SHGC-35441 | 59 |
| S19 | SHGC-6150 | 33 |
| S21 | AFM224ye9 | 21 |
| S23 | SHGC-31478 | 25 |
| S24 | SHGC-3921 | — | the ΔCt values of the above described framework markers along Chromosome 19 relative to PRO201 is indicated for selected tumors in Table 5.

TABLE 5

Amplification of framework markers relative to DNA30676 (ΔCt)

| | Framework Markers | | | | |
|---|---|---|---|---|---|
| Tumor | S12 | DNA30676 | S50 | S105 | S155 |
| LT1 | 0.16 | −0.18 | 0.06 | −0.42 | 0.11 |
| LT1a | 0.05 | 0.79 | −0.27 | 0.17 | 0.40 |
| LT2 | 0.48 | −0.09 | 0.41 | 0.52 | 0.13 |
| LT3 | 0.27 | 1.04 | 0.83 | 0.11 | 0.50 |
| LT4 | 0.48 | −0.18 | 0.67 | 0.20 | 0.56 |
| LT6 | 0.72 | −0.23 | 0.74 | 0.32 | 0.35 |
| LT7 | 0.82 | −0.36 | 0.85 | 0.95 | 0.95 |
| LT9 | 0.72 | −0.75 | 0.61 | 0.19 | 0.64 |
| LT10 | 0.82 | 0.05 | 0.98 | 0.62 | 0.53 |
| LT11 | 0.13 | 0.64 | 0.25 | 0.55 | −0.34 |
| LT12 | 0.04 | −0.60 | 0.60 | 0.21 | −0.17 |
| LT13 | −0.06 | 0.67 | 0.57 | −0.30 | −0.05 |
| LT15 | −0.03 | 1.43 | −0.77 | 0.12 | −0.04 |
| LT16 | 0.46 | 1.35 | 1.37 | 0.51 | 0.23 |
| LT17 | 0.37 | 1.51 | 0.74 | 0.21 | 0.22 |
| LT18 | 0.39 | 1.22 | 0.57 | 0.11 | 0.16 |
| LT22 | 0.79 | 0.13 | 0.76 | −0.05 | 0.16 |
| CT2 | 0.25 | 2.81 | 0.29 | 0.37 | −0.02 |
| CT3 | −0.17 | 2.03 | −0.10 | 0.34 | −0.28 |
| CT8 | 0.13 | 1.39 | 0.57 | 0.18 | −0.16 |
| CT10 | 0.15 | 2.21 | 0.51 | −0.01 | −0.81 |
| CT12 | 0.13 | 1.93 | 0.57 | 0.41 | 0.20 |
| CT14 | 0.40 | 2.37 | 0.39 | 0.45 | 0.36 |
| CT15 | −0.23 | 1.27 | −0.30 | −0.06 | 0.56 |
| CT16 | 0.38 | 1.76 | 0.31 | 0.24 | 0.04 |
| CT17 | 0.25 | 1.65 | 0.71 | 0.32 | 0.22 |

Table 6 indicate the ΔCt values for results of epicenter mapping relative to DNA30676 (SEQ ID NO:2), indicating the relative amplification in the region more immediate to the actual location of DNA30676 (SEQ ID NO:2) along chromosome 19.

TABLE 6

Amplification of epicenter markers relative to DNA30676 (ΔCt)

| Tumor | S12 | S16 | S17 | S18 | DNA30676 | S21 | S23 | S24 |
|---|---|---|---|---|---|---|---|---|
| LT1 | — | 0.22 | −0.16 | 0.02 | −0.29 | 0.40 | −0.02 | 0.14 |
| LT1a | — | 0.11 | −0.52 | 0.32 | 0.58 | 0.55 | 0.04 | −0.15 |
| LT2 | — | 0.07 | −0.07 | 0.34 | −0.04 | 0.07 | 0.13 | 0.12 |
| LT3 | — | 0.01 | −0.46 | 0.47 | 1.87 | 0.16 | 0.24 | 0.02 |
| LT4 | — | 0.36 | −0.96 | 0.93 | −1.18 | −0.54 | −0.07 | −0.23 |
| LT6 | — | 0.35 | −0.70 | −0.04 | 0.28 | −0.24 | −0.12 | −0.01 |
| LT7 | — | −0.32 | −0.34 | −0.27 | 0.29 | −0.74 | −0.07 | 0.02 |
| LT9 | — | −0.42 | −0.66 | −0.36 | 0.07 | −1.42 | −0.26 | −0.70 |
| LT10 | — | −0.26 | −0.14 | −0.07 | 0.55 | −0.32 | −0.04 | −0.08 |
| LT11 | — | −0.22 | −0.77 | 0.05 | 0.68 | −0.85 | −0.13 | 0.09 |
| LT12 | — | −0.94 | −1.52 | −1.26 | 0.13 | 0.08 | −0.09 | 0.24 |
| LT13 | — | 0.24 | 0.02 | 0.35 | 1.44 | −0.08 | 0.50 | 0.49 |

TABLE 6-continued

Amplification of epicenter markers relative to DNA30676 (ΔCt)

| Tumor | S12 | S16 | S17 | S18 | DNA30676 | S21 | S23 | S24 |
|---|---|---|---|---|---|---|---|---|
| LT15 | — | −0.09 | −0.64 | 0.26 | 1.99 | 0.03 | 0.09 | −0.06 |
| LT16 | — | 0.06 | −0.16 | 0.20 | 1.72 | 0.75 | 0.54 | 0.64 |
| LT17 | — | −0.91 | −1.71 | −0.78 | −0.15 | −2.89 | −0.82 | −0.42 |
| LT18 | — | 0.30 | −0.20 | 0.71 | 1.09 | −0.29 | 0.82 | 0.42 |
| LT22 | — | 0.37 | −0.82 | 0.47 | 0.07 | 0.46 | 0.38 | 0.65 |
| CT1 | 0.18 | 0.02 | 0.32 | 0.57 | 1.61 | 0.75 | 0.56 | 0.05 |
| CT2 | 0.46 | 0.19 | 0.35 | 0.59 | 3.51 | −0.15 | 0.53 | 0.14 |
| CT3 | −0.02 | −0.24 | 0.05 | 0.13 | 2.19 | −0.31 | 0.13 | −0.34 |
| CT4 | 0.29 | 0.20 | 0.42 | 0.64 | 3.22 | 0.47 | 0.27 | 0.33 |
| CT5 | −0.15 | −0.16 | 0.12 | 0.21 | 2.83 | 0.09 | −0.08 | −0.17 |
| CT6 | 0.13 | 0.17 | 0.87 | 0.26 | 2.93 | 0.44 | 0.04 | 0.39 |
| CT7 | 0.13 | −0.03 | 0.78 | −0.04 | 2.43 | −0.68 | −0.26 | 0.20 |
| CT8 | 0.45 | −0.03 | 0.58 | 0.22 | 1.95 | 0.25 | 0.57 | 0.07 |
| CT9 | 0.50 | 0.41 | 0.98 | 0.64 | 2.72 | 0.24 | 0.06 | 0.66 |
| CT10 | 0.11 | −0.40 | 0.32 | 0.13 | 3.12 | −0.16 | 0.28 | −0.16 |
| CT11 | 0.18 | 0.01 | 0.45 | 0.82 | 3.26 | 0.34 | 0.00 | 0.27 |
| CT12 | 0.53 | 0.08 | 0.72 | 0.40 | 2.77 | 0.36 | 0.67 | 0.09 |
| CT14 | 0.57 | −0.13 | 0.87 | 0.63 | 2.88 | 0.59 | 0.74 | 0.09 |
| CT15 | −0.09 | −0.57 | 0.05 | 0.11 | 2.60 | −0.07 | 0.20 | −0.34 |
| CT16 | 0.57 | −0.21 | 0.80 | 0.36 | 2.61 | 0.38 | 0.49 | 0.16 |
| CT17 | 0.25 | −0.26 | 0.38 | 0.29 | 2.24 | −0.05 | 0.67 | 0.05 |
| CT18 | 0.38 | 0.18 | 0.53 | 0.49 | 2.48 | 0.41 | −0.29 | 0.12 |

DISCUSSION and CONCLUSION

The ΔCt values for DNA30676 (SEQ ID NO:2) and DNA40556 (SEQ ID NO:20) in a variety of lung and colon tumors are reported in Table 2. A ΔCt of >1 was typically used as the threshold value for amplification scoring, as this represents a doubling of gene copy. Table 2 indicates that significant amplification of DNA30676 occurred in: primary lung tumors: LT1a, LT3, LT11, LT13, LT15, LT17, LT19; primary colon tumors, CT2, CT3, CT8, CT10, CT12, CT14, CT15, CT16, CT17, CT1, CT4, CT5, CT6, CT7, CT9, CT11,CT18; lung tumor cell lines Calu-1, Calu-6, H157, H441, SKMES1, H522 and H810; and colon tumor cell lines Colo-320 and Colo-205. Table 2 further indicates significant amplification of DNA40556 in: primary lung tumors LT1a, LT8, LT11, LT15, LT17, LT19; primary colon tumors CT14, CT5, CT11 and lung tumor cell line A549.

The ΔCt and average ΔCt values of DNA30676 (SEQ ID NO:2) for the primary lung tumor hits are: 1.10, 2.05, 1.52, 2.13, 2.58, 1.63, 3.42; primary colon tumor hits 3.81, 2.3, 1.97, 3.01, 2.76, 3.34, 2.58, 2.46, 2.64, 1.57, 3.39, 2.95, 2.81, 2.77, 2.63, 3.0, 2.23; lung tumor cell line hits: 2.37, 2.61, 2.39, 2.07, 3.01, 2.91 and 2.07; colon tumor cell lines: 1.95 and 1.26. The ΔCt and average ΔCt values of DNA40556 for the primary lung hits are 1.03, 1.14, 1.33, 1.18, 1.00 and 1.42; colon tumor hits: 1.12, 1.00 and 1.135; lung tumor cell line 1.26.

The ΔCt and average ΔCt values of DNA30676 (SEQ ID NO:2) enumerated in the previous paragraph represent an increase in gene copy, relative to normal tissue, of 2.14, 4.14, 2.87, 4.38, 5.98, 3.09, 10.70 for the primary lung tumor hits: 14.03, 4.92, 3.92, 8.06, 6.77, 10.13, 5.98, 5.50, 6.23, 2.97, 10.48, 7.73, 7.01, 6.82, 6.19, 8.0, 4.69 for the primary colon tumor hits; 5.17, 6.10, 5.24, 4.20, 8.06, 7.51, 4.20 for the lung tumor cell line hits; 3.86, 2.40 for the colon tumor cell lines. For DNA40556, these values represent an increase in gene copy, relative to normal tissue of: 2.04, 2.20, 2.51, 2.27, 2.0, 2.68 for the lung, tumor hits, 2.17, 2.0, 2.20 for the colon tumor hits; 2.39.

Amplification has been confirmed by framework mapping for DNA30676 (SEQ ID NO:2): in primary lung tumors LT3, LT15, LT16, LT17, LT18; and in primary colon tumors CT2, CT3, CT8, CT9, CT10, CT12, CT14, CT15, CT16, CT17. The reported ΔCt values for the primary lung tumors are 1.04, 1.43, 1.35, 1.51 and 1.22, while the primary colon tumors report 2.81, 2.03, 1.39, 2.21, 1.93, 2.37, 1.27, 1.76 and 1.65. Relative to normal tissue, this represents approximately a 2.06, 2.69, 2.55, 2.85, and 2.32 fold increase for the lung tumors, and a 7.01, 4.08, 2.62, 4.63, 3.81, 5.17, 2.41, 3.39, 3.14 fold increase for the colon tumors. Epicenter mapping for DNA30676 resulted in confirmation of significant amplification: in primary lung tumors LT3, LT13, LT15, LT16, LT18; and in primary colon tumors CT1, CT2, CT3, CT4, CT5, CT6, CT7, CT8, CT9, CT10, CT11, CT12, CT14, CT15, CT6, CT17 and CT18. The reported ΔCt values for the primary lung tumors were 1.87, 1.44, 1.99, 1.72 and 1.09, while the primary colon tumors indicated ACt and average ACt values of 2.56, 3.51, 2.19, 3.22, 2.83, 2.93, 2.43, 1.95, 2.72, 3.12, 3.26, 2.77, 2.88, 2.60, 2.61, 2.24 and 2.48. Relative to normal tissue, this represents a 3.66, 2.71, 3.97, 3.29, 2.13-fold increase in gene copy for the lung tumors and a 5.90, 11.39, 4.56, 9.32, 7.11, 7.62, 5.39, 3.86, 6.59, 8.69, 9.58, 6.82, 7.36, 6.06, 6.11, 4.72, 5.58-fold increase increase in gene copy for the colon tumors.

In contrast, the amplification of the closest known framework markers (with one exception, i.e. S50)(Table 5) or epicenter markers (Table 6) does not occur to a greater extent than that of DNA30676 (SEQ ID NO:2). This strongly suggests that DNA30676 (SEQ ID NO:2) is the gene responsible for the amplification of the particular region on Chromosome 19. Because amplification of DNA30676 (SFQ ID NO:2) occurs in various lung and colon tumors and cell lines (especially colon), it is highly probable to play a significant role in tumor formation or growth. As a result, antagonists (e.g., antibodies) directed against the protein encoded by DNA30676 (SEQ ID NO:2) (i.e., Nsp1 (SEQ ID NO:1), DNA40575 (SEQ ID NO:4) and DNA61601 (SEQ ID NO:6) would be expected to have utility in cancer therapy.

Example 15

In situ Hybridization

In situ hybridization is a powerful and versatile technique for the detection and localization of nucleic acid sequences within cell or tissue preparations. It may be useful, for example, to identify sites of gene expression, analyze the tissue distribution of transcription, identify and localize viral infection, follow changes in specific mRNA synthesis and aid in chromosome mapping.

In situ hybridization was performed following an optimized version of the protocol by Lu and Gillett, Cell vision 1: 169–176 (1994), using PCR-generated $^{33}$P-labeled riboprobes. Briefly, formalin-fixed, paraffin-embedded human tissues were sectioned, deparaffinized, deproteinated in proteinase K (20 g/ml) for 15 minutes at 37° C., and further processed for in situ hybridization as described by Lu and Gillett, supra. A[$^{33}$-P] UTP-labeled antisense niboprobe was generated from a PCR product and hybridized at 55° C. overnight. The slides were dipped in Kodak NTB2 nuclear track emulsion and exposed for 4 weeks.

$^{33}$P-Riboprobe synthesis 6.0 μl (125 mCi) of $^{33}$P-UTP (Amersharn BF 1002, SA<2000 Ci/mmol) were speed vac dried. To each tube containing dried $^{33}$P-UTP, the following ingredients were added:

2.0 μl 5×transcription buffer
1.0 μl DTT (100 mM)
2.0 μl NTP mix (2.5 mM : 10 μl; each of 10 mM GTP, CTP & ATP+10 μl H$_2$O)
1.0 μl UTP (50)μM)
1.0 μl Rnasin
1.0 μl DNA template (1 μg)
1.0 μl H$_2$O
1.0 μl RNA polymerase (for PCR products T3=AS, T7= S. usually)

The tubes were incubated at 37° C. for one hour. 1.0 μl RQ1 DNase were added, followed by incubation at 37° C. for 15 minutes. 90 μl TE (10 mM Tris pH 7.6/1 mM EDTA pH 8.0) were added, and the mixture was pipetted onto DE81 paper. The remaining solution was loaded in a Microcon-50 ultrafiltration unit, and spun using program 10 (6 minutes). The filtration unit was inverted over a second tube and spun using program 2 (3 minutes). After the final recovery spin, 100 μl TE were added. 1 μl of the final product was pipetted on DE81 paper and counted in 6 ml of Biofluor II.

The probe was run on a TBE/urea gel. 1–3 μl of the probe or 5 μl of RNA Mrk III were added to 3 μl of loading buffer. After heating on a 95° C. heat block for three minutes, the gel was immediately placed on ice. The wells of gel were flushed, the sample loaded, and run at 180–250 volts for 45 minutes. The gel was wrapped in saran wrap and exposed to XAR film with an intensifying screen in −70° C. freezer one hour to overnight.

$^{33}$P-Hybridization

Pretreatment of frozen sections The slides were removed from the freezer, placed on aluminium trays and thawed at room temperature for 5 minutes. The trays were placed in 55° C. incubator for five minutes to reduce condensation. The slides were fixed for 10 minutes in 4% paraformaldehyde on ice in the fume hood, and washed in 0.5×SSC for 5 minutes, at room temperature (25 ml 20×SSC+975 ml SQ H$_2$O). After deproteination in 0.5 μg/ml proteinase K for 10 minutes at 37° C. (12.5 μl of 10 mg/ml stock in 250 ml prewarmed RNase-free RNAse buffer), the sections were washed in 0.5×SSC for 10 minutes at room temperature. The sections were dehydrated in 70%, 95%, 100% ethanol, 2 minutes each.

Pretreatment of paraffin-embeddedsections The slides were deparaffinized, placed in SQ H$_2$O, and rinsed twice in 2×SSC at room temperature, for 5 minutes each time. The sections were deproteinated in 20 μg/ml proteinase K (500 μl of 10 mg/ml in 250 ml RNase-free RNase buffer; 37° C., 15 minutes )human embryo, or 8×proteinase K (100 μl in 250 ml Rnase buffer, 37° C., 30 minutes)—formalin tissues. Subsequent rinsing in 0.5×SSC and dehydration were performed as described above.

Prehybridization The slides were laid out in plastic box lined with Box buffer (4×SSC, 50% formamide)-saturated filter paper. The tissue was covered with 50 μl of hybridization buffer (3.75g Dextran Sulfate+6 ml SQ H$_2$O), vortexed and heated in the microwave for 2 minutes with the cap loosened. After cooling on ice, 18.75 ml formamide, 3.75 ml 20×SSC and 9 ml SQ H$_2$O were added, the tissue was vortexed well, and incubated at 42° C. for 1–4 hours.

If hybridization 1.0×10$^6$ cpm probe and 1.0 μl tRNA (50 mg/ml stock) per slide were heated at 95° C. for 3 minutes. The slides were cooled on ice, and 48 μl hybridization buffer were added per slide. After vortexing, 50 μl $^{33}$P mix were added to 50 μl prehybridization on slide. The slides were incubated overnight at 55° C.

Washes Washing was done 2×10 minutes with 2×SSC, EDTA at room temperature (400 ml 20×SSC+16 ml 0.25M EDTA, V$_f$=4L), followed by RNaseA treatment at 37° C. for 30 minutes (500 μl of 10 mg/ml in 250 ml Rnase buffer=20 μg/ml). The slides were washed 2×10 minutes with 2×SSC, EDTA at room temperature. The stringency wash conditions were as follows: 2 hours at 55° C., 0.1×SSC, EDTA (20 ml 20×SSC+16 ml EDTA, V$_f$=4L).

Expression of DNA 30676 Panc.shc (nsp-1) in Human Tissues III

Comparable background signal observed with sense and antisense probes in many tissues. The only sites where expression appeared to be specific were fetal thymic medulla, fetal spleen, epithelium of fetal small intestine and in osteocytes at regions of new bone formation. No specific signal was observed in either fetal or normal adult pancreas. Fetal tissues were approximately 12–16 weeks gestation. Oligos used were B-191D and B-191E.

Expression of DNA 30676 (SHC hlog/nsp1) in Colon Tumors, Fetal Liver, and Transfected Cell Lines The purpose of this study was to determine the expression of DNA 30676 in colonic carcinomas. This DNA has been shown to be amplified in colon cancer. Expression was analyzed in control cell pellets and in 10 colon cancers. Control cell pellets included SHC transfected 293 cells and SW480 cells, which express SHC (cells were submitted as H98-717).

Examination of cell pellets showed the SHC transfected cells were positive with both sense and antisense probes making interpretation of this study problematic. The SW480 cells were negative with both probes. For the colon cancers only AS probes were run. A number of the colon cancers showed slight expression, and this was strongest in specimen 9727198. However, in light of the cell pellet data this signal is difficult to interpret and overall, it is felt that the signal is insufficient to be called as positive.

The oligonucleotide probes indicated below were used in the in situ hybridizations described in this example:

B166A-: GGATTCTAATACGACTCACTAT-AGGGCGCGGAGGCTGCTCTGGGGTsAG (SEQ ID NO:30)

B-166B-CTATGAAATTAACCCTCACTAAAGGGAT-GTTGCCCTGGCTGGTCTTGA (SEQ ID NO:31)

B-191D-GGATTCTAATACGACTCACTAT-AGGGCATCTGCCTTGCCCCGAACGAG (SEQ ID NO:32)

B-191E-CTATGMAAATAACCCTCACTAAAGGGAT-CATCCAGAGCCCGCATCAGC (SEQ ID NO:33)

A-3231-GGATTCTAATACGACTCACTATAGGGCA-GATGTGGAAGACTGAGGCCT (SEQ ID NO:34)

A-323J-CTATGAAATTAACCCTCACTAAAGG-GAATATGTGCCAAATCTGCAGGCT (SEQ ID NO:35)

Deposit of Material

The following materials have been deposited with the American Type Culture Collection, (ATCC): 10801 University Blvd., Manassas, Va. USA

| Material | ATCC Dep. No. | Deposit Date |
|---|---|---|
| DNA30676-1223 | 209567 | 12/23/97 |
| DNA40575-1223 | 209565 | 12/23/97 |
| DNA40556-1223 | 209566 | 12/23/97 |
| DNA40554-1223 | 209564 | 12/23/97 |
| DNA61601-1223 | 209713 | 3/31/98 |

DNA40556 & DNA40554 may be combined to cover a full length coding sequence of a Nsp3 variant.

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient. to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. An isolated nucleic acid molecule having at least about 80% sequence identity to:
   (a) a nucleotide sequence encoding amino acid residues 1 to 576 of SEQ ID NO:1,
   (b) a nucleotide sequence of SEQ ID NO:2,
   (c) nucleotides 152 to 1882 of SEQ ID NO:2, or
   (d) the full-length coding sequence of the cDNA deposited under ATCC accession number 209567, wherein said isolated nucleic acid molecule encodes a polypeptide capable of binding to an epidermal growth factor receptor, an insulin receptor or a p130$^{cas}$ polypeptide.

2. A vector comprising the isolated nucleic acid molecule of claim 1.

3. A host cell comprising the vector of claim 2.

4. The host cell of claim 3 which is a CHO cell, an *Escherichia coil* cell, a yeast cell or a Baculovirus-infected insect cell.

5. A process for producing a PRO201 polypeptide comprising culturing the host cell of claim 3 under conditions suitable for expression of said polypeptide and recovering said polypeptide from the cell culture.

6. An isolated nucleic acid molecule that hybridizes under stringent hybridization and washing conditions to:
   (a) a nucleotide sequence encoding amino acid residues 1 to 576 of SEQ ID NO:1,
   (b) the complement of (a),
   (c) a nucleotide sequence shown as SEQ ID NO:2,
   (d) nucleotides 152 to 1882 of SEQ ID NO:2, or
   (e) the full-length coding sequence of the cDNA deposited under ATCC accession number 209567.

7. A vector comprising the nucleic acid molecule of claim 6.

8. A host cell comprising the vector of claim 7.

9. The host cell of claim 8 which is a CHO cell, an *Escherichia coli* cell, a yeast cell or a Baculovirus-infected insect cell.

10. A process for producing a PRO201 polypeptide comprising culturing the host cell of claim 8 under conditions suitable for expression of said polypeptide and recovering said polypeptide from the cell culture.

11. An isolated polypeptide having at least 80% sequence identity to SEQ ID NO: 1, wherein said isolated nucleic acid molecule encodes a polypeptide capable of binding to an epidermal growth factor receptor, an insulin receptor or a p130$^{cas}$ polypeptide.

12. An antibody which specifically binds to a PRO201 polypeptide comprising amino acid residues 1 to 576 of SEQ ID NO:1.

13. The antibody of claim 12, wherein said antibody is a monoclonal antibody.

14. The antibody of claim 12 which is labeled.

15. The antibody of claim 12 which is immobilized on a solid support.

16. A composition comprising an antibody of claim 12 in admixture with a pharmaceutically acceptable carrier.

17. The antibody of claim 12 which is bispecific.

18. The antibody of claim 12 which is heteroconjugated.

19. The antibody of claim 12 which is formulated as an immunoliposome.

20. The antibody of claim 12 which is an antigen binding fragment or a single-chain antibody.

21. The antibody of claim 20, wherein the antigen binding fragment is selected from the group consisting of: Fab, Fab', F(ab')$_2$ and Fv.

* * * * *